United States Patent
Trick et al.

(10) Patent No.: US 10,557,144 B2
(45) Date of Patent: Feb. 11, 2020

(54) EXPRESSION OF THERMOSTABLE STARCH SYNTHASE GENES IMPROVES THE YIELD IN HEAT STRESS

(71) Applicant: Kansas State University Research Foundation, Manhattan, KS (US)

(72) Inventors: Harold N. Trick, Olsburg, KS (US); Allan Fritz, Wamego, KS (US); Shyamal Talukder, Ardmore, OK (US)

(73) Assignee: Kansas State University Research Foundation, Manhattan, KS (US)

( * ) Notice: Subject to any disclaimer, the term of this patent is extended or adjusted under 35 U.S.C. 154(b) by 0 days.

(21) Appl. No.: 15/957,639

(22) Filed: Apr. 19, 2018

(65) Prior Publication Data

US 2018/0237795 A1   Aug. 23, 2018

Related U.S. Application Data

(63) Continuation of application No. 14/911,990, filed as application No. PCT/US2014/050932 on Aug. 13, 2014, now abandoned.

(60) Provisional application No. 61/865,767, filed on Aug. 14, 2013.

(51) Int. Cl.
  *C12N 15/82* (2006.01)
(52) U.S. Cl.
  CPC ..... *C12N 15/8271* (2013.01); *C12N 15/8261* (2013.01); *C12Y 204/01021* (2013.01)
(58) Field of Classification Search
  None
  See application file for complete search history.

(56) References Cited

U.S. PATENT DOCUMENTS

| 6,013,861 | A  | * | 1/2000  | Bird ................... C12N 15/8245 800/263 |
| 6,130,367 | A  |   | 10/2000 | Kossmann et al. |
| 7,563,944 | B2 |   | 7/2009  | Heim et al. |
| 2007/0118916 | A1 |   | 5/2007 | Puzio et al. |
| 2008/0109921 | A1 |   | 5/2008 | Hannah et al. |

FOREIGN PATENT DOCUMENTS

WO   2013096993   7/2013

OTHER PUBLICATIONS

Xin et al, 2013, PLoS ONE, 8:1-14.*
Yang et al, 2018, Scientific Reports, 8:1-9.*
The International Search Report and Written Opinion dated Jun. 8, 2015, in PCT/US14/50932 filed Aug. 13, 2014.
Sumesh, K.V. "Starch synthase activity and heat shock protein in relation to thermal tolerance of developing wheat grains," Biologia Plantarum 52 (4) pp. 749-753, 2008.
Office Action dated Feb. 7, 2017, in U.S. Appl. No. 14/911,990, filed Feb. 12, 2016.
The Office Action dated Jul. 3, 2017, in U.S. Appl. No. 14/911,990, filed Feb. 12, 2016.
The Office Action dated Dec. 19, 2017, in U.S. Appl. No. 14/911,990, filed Feb. 12, 2016.

* cited by examiner

*Primary Examiner* — Jason Deveau Rosen
(74) *Attorney, Agent, or Firm* — Hovey Williams LLP

(57) ABSTRACT

Genetically-modified plants having increased tolerance to heat stress are described. Methods of producing such genetically-modified plants are also disclosed. The genetically-modified plants comprise exogenous nucleic acid encoding a thermostable protein having starch synthase activity. Genetically-modified plants have increased yield when grown under elevated conditions as compared to control plants.

16 Claims, 5 Drawing Sheets

Specification includes a Sequence Listing.

SEQUENCE LISTING

```
<160> NUMBER OF SEQ ID NOS: 41

<210> SEQ ID NO 1
<211> LENGTH: 1926
<212> TYPE: DNA
<213> ORGANISM: Oryza sativa
<220> FEATURE:
<221> NAME/KEY: misc_feature
<222> LOCATION: (1)..(1926)
<223> OTHER INFORMATION: Codon optimized cDNA sequence

<400> SEQUENCE: 1
atggcgacgg cggcggggat ggggatcggg gcggcgtgcc tggtggcgcc gcaggtgagg      60
ccggggagga ggttgcggct ccagcgggtg cggaggcggt gcgtggcgga gctgagcagg     120
gacggtgggt cggcgcagcg cccgctggca ccggcgccgc tggtgaagca gccggtcctg     180
ccgaccttcc tcgtgccgac gtcgacgcca cccgcgccca cgcagtcgcc ggcgccggcg     240
ccgacccccg cgccgttgcc ggactccggc gtgggggaga tcgagcccga tctagaaggt     300
ctcacagaag attccatcga caaaacaatt tttgtggcta gtgagcagga gtctgagatc     360
atggatgtga aggagcaagc tcaagctaaa gtaacacgca gcgttgtctt tgtaaccggt     420
gaagcttctc cttatgcaaa gtcaggtgga ctaggagatg tttgtggttc actgccaatt     480
gctcttgctc ttcgtggtca tcgtgtgatg gttgtaatgc cgagatacat gaacggggcc     540
ttgaacaaaa attttgcaaa cgcattttac actgagaagc acattaagat tccatgcttt     600
ggcggagaac atgaagttac ttttttttcac gagtataggg attctgttga ttgggtgttt     660
gttgatcatc cctcatatca tagacctgga aatttgtatg gagataattt tggtgctttt     720
ggcgataatc agttcagata cacactcctg tgctatgcgg cgtgtgaagc cccattaatt     780
cttgaactgg gaggatatat ctatggacag aaatgcatgt ttgttgtgaa tgattggcat     840
gccagtcttg tgccagtcct tcttgctgca aaatatagac catatggtgt ttacagggat     900
gcccgcagtg ttcttgtcat acataatcta gcacatcagg gtgtggagcc tgccagtaca     960
tatcctgacc tgggattgcc acctgaatgg tatggagcat agaatgggt gtttccagag    1020 tgggcaaggc ggcatgccct tgacaagggt gaggcagtca atttttaaa aggcgcagtt    1080 gtgacagcag atcgaattgt gactgtcagc caggggtatt catgggaggt cacaactgct    1140
gaaggtgggc aaggcctcaa tgagctctta agctcccgga gagtgtatt gaatggaatt    1200 gtaaatggaa ttgacattaa tgattggaac ccatccacag acaagtttct cccttatcat    1260
tattctgttg atgacctgtc cggaaaggcc aagtgtaaag ctgaattgca gaaggagctg    1320
ggtttaccta taaggcccga tgtgcctctg attggcttta ttggaagatt ggactatcaa    1380
aaaggcattg atctaattaa acttgccatt ccagatctca tgcgggacaa tattcaattc    1440
gtcatgcttg gatctggtga cccaggtttt gaaggatgga tgagatccac agaatcaggg    1500
tacagggata aatttcgtgg atgggttgga tttagtgttc cagtttccca ccgaataact    1560
gcaggttgcg atatattgtt gatgccatcc agattcgaac cttgtggcct caatcagcta    1620
tatgctatgc aatatggtac agtgcctgtt gttcatggaa ctggaggcct cagagataca    1680
gtggagaatt ttaacccgtt tgctgagaaa ggagagcagg gtacagggtg ggcattctcg    1740
ccactaacca ttgaaaaaat gctgtgggca ttgcggatgg caatttcgac atacagggaa    1800
```

-continued

```
cacaagtcct cttgggaggg tctaatgaag cgaggcatgt caagcgactt tacatgggac   1860
catgccgcct cacagtatga acagatcttc gaatgggcct tcatggatca accatatgtc   1920
atgtaa                                                              1926
```

<210> SEQ ID NO 2
<211> LENGTH: 641
<212> TYPE: PRT
<213> ORGANISM: Oryza sativa

<400> SEQUENCE: 2

```
Met Ala Thr Ala Ala Gly Met Gly Ile Gly Ala Ala Cys Leu Val Ala
 1               5                  10                  15

Pro Gln Val Arg Pro Gly Arg Arg Leu Arg Leu Gln Arg Val Arg Arg
            20                  25                  30

Arg Cys Val Ala Glu Leu Ser Arg Asp Gly Gly Ser Ala Gln Arg Pro
        35                  40                  45

Leu Ala Pro Ala Pro Leu Val Lys Gln Pro Val Leu Pro Thr Phe Leu
    50                  55                  60

Val Pro Thr Ser Thr Pro Pro Ala Pro Thr Gln Ser Pro Ala Pro Ala
65                  70                  75                  80

Pro Thr Pro Pro Pro Leu Pro Asp Ser Gly Val Gly Glu Ile Glu Pro
                85                  90                  95

Asp Leu Glu Gly Leu Thr Glu Asp Ser Ile Asp Lys Thr Ile Phe Val
            100                 105                 110

Ala Ser Glu Gln Glu Ser Glu Ile Met Asp Val Lys Glu Gln Ala Gln
        115                 120                 125

Ala Lys Val Thr Arg Ser Val Val Phe Val Thr Gly Glu Ala Ser Pro
    130                 135                 140

Tyr Ala Lys Ser Gly Gly Leu Gly Asp Val Cys Gly Ser Leu Pro Ile
145                 150                 155                 160

Ala Leu Ala Leu Arg Gly His Arg Val Met Val Met Pro Arg Tyr
                165                 170                 175

Met Asn Gly Ala Leu Asn Lys Asn Phe Ala Asn Ala Phe Tyr Thr Glu
            180                 185                 190

Lys His Ile Lys Ile Pro Cys Phe Gly Gly Glu His Glu Val Thr Phe
        195                 200                 205

Phe His Glu Tyr Arg Asp Ser Val Asp Trp Val Phe Val Asp His Pro
    210                 215                 220

Ser Tyr His Arg Pro Gly Asn Leu Tyr Gly Asp Asn Phe Gly Ala Phe
225                 230                 235                 240

Gly Asp Asn Gln Phe Arg Tyr Thr Leu Leu Cys Tyr Ala Ala Cys Glu
                245                 250                 255

Ala Pro Leu Ile Leu Glu Leu Gly Gly Tyr Ile Tyr Gly Gln Lys Cys
            260                 265                 270

Met Phe Val Val Asn Asp Trp His Ala Ser Leu Val Pro Val Leu Leu
        275                 280                 285

Ala Ala Lys Tyr Arg Pro Tyr Gly Val Tyr Arg Asp Ala Arg Ser Val
    290                 295                 300

Leu Val Ile His Asn Leu Ala His Gln Gly Val Glu Pro Ala Ser Thr
305                 310                 315                 320

Tyr Pro Asp Leu Gly Leu Pro Pro Glu Trp Tyr Gly Ala Leu Glu Trp
                325                 330                 335

Val Phe Pro Glu Trp Ala Arg Arg His Ala Leu Asp Lys Gly Glu Ala
```

```
           340                 345                 350
Val Asn Phe Leu Lys Gly Ala Val Thr Ala Asp Arg Ile Val Thr
            355                 360                 365
Val Ser Gln Gly Tyr Ser Trp Glu Val Thr Ala Glu Gly Gly Gln
            370                 375                 380
Gly Leu Asn Glu Leu Leu Ser Ser Arg Lys Ser Val Leu Asn Gly Ile
385                 390                 395                 400
Val Asn Gly Ile Asp Ile Asn Asp Trp Asn Pro Ser Thr Asp Lys Phe
                405                 410                 415
Leu Pro Tyr His Tyr Ser Val Asp Asp Leu Ser Gly Lys Ala Lys Cys
                420                 425                 430
Lys Ala Glu Leu Gln Lys Glu Leu Gly Leu Pro Ile Arg Pro Asp Val
            435                 440                 445
Pro Leu Ile Gly Phe Ile Gly Arg Leu Asp Tyr Gln Lys Gly Ile Asp
            450                 455                 460
Leu Ile Lys Leu Ala Ile Pro Asp Leu Met Arg Asp Asn Ile Gln Phe
465                 470                 475                 480
Val Met Leu Gly Ser Gly Asp Pro Gly Phe Glu Gly Trp Met Arg Ser
                485                 490                 495
Thr Glu Ser Gly Tyr Arg Asp Lys Phe Arg Gly Trp Val Gly Phe Ser
                500                 505                 510
Val Pro Val Ser His Arg Ile Thr Ala Gly Cys Asp Ile Leu Leu Met
            515                 520                 525
Pro Ser Arg Phe Glu Pro Cys Gly Leu Asn Gln Leu Tyr Ala Met Gln
            530                 535                 540
Tyr Gly Thr Val Pro Val Val His Gly Thr Gly Gly Leu Arg Asp Thr
545                 550                 555                 560
Val Glu Asn Phe Asn Pro Phe Ala Glu Lys Gly Glu Gln Gly Thr Gly
                565                 570                 575
Trp Ala Phe Ser Pro Leu Thr Ile Glu Lys Met Leu Trp Ala Leu Arg
                580                 585                 590
Met Ala Ile Ser Thr Tyr Arg Glu His Lys Ser Ser Trp Glu Gly Leu
            595                 600                 605
Met Lys Arg Gly Met Ser Ser Asp Phe Thr Trp Asp His Ala Ala Ser
            610                 615                 620
Gln Tyr Glu Gln Ile Phe Glu Trp Ala Phe Met Asp Gln Pro Tyr Val
625                 630                 635                 640
Met
```

<210> SEQ ID NO 3
<211> LENGTH: 1902
<212> TYPE: DNA
<213> ORGANISM: Vitis vinifera
<220> FEATURE:
<221> NAME/KEY: misc_feature
<222> LOCATION: (1)..(1902)
<223> OTHER INFORMATION: Codon optimized cDNA sequence

<400> SEQUENCE: 3

| | | | | | |
|---|---|---|---|---|---|
| atggagagcc | tgcaatcgcc | cctggtgctg | tcgtctaagc | tgctgcctaa | ctcgctgaag | 60 |
| aagcccgtcc | tggaggttgg | gttcgcttgc | ttcttcaagc | aaaggcgcgt | catccagtct | 120 |
| gtttccatca | agaggtctgt | ggtctgctgc | tccagaaagg | gcgggggcgg | gggctcgcaa | 180 |
| gacggctcca | gcgcgatgct | ggtgaacacc | gacaagaagg | atgctagcga | ctcggtcggc | 240 |
| ttccacctcg | ttccacctcc | tagcggcgat | aacggggtca | tcgacccgca | tgagaagctc | 300 |

```
tcgacccaga aggaggccga gacgggcaac tcagaggggg aggaggagag gaagaccaag    360
gtgacgtaca acatcgtgtt cgtcacctca gagtctgctc catactctaa gacgggggc    420
ctgggcgacg tgtgcgggtc cctgccgatc gccctcgccg cgcacggcca tcgggtcatg    480
gttgtgtccc ccagatacca aaacggcacc tgcagcgatg agatcttctc cggggctagc    540
gacctcgagc acccgatcaa ggtgcattgc ttcggggggcg tccaggaggt ttccttcttc    600
cacgagtacc gggcgggcgt cgattgggtt ttcgtggacc acccccagcta ccataggcct    660
ggcaacccct tacggcgatgg gtacggcgct ttcggcgaca accaattccg cttcacccctc    720
ctgtgccacg ctgcttgcga ggctcctctc gttctgcctc tcgggggctt cacctacggc    780
gagaagtgcc tgttcctcgt caacgactgg cacgcttccc tcgtccctgt tctcctggct    840
gctaagtaca ggcctcatgg cgtgtacaag gatgcgcgca ccgtgctggt catccacaac    900
ctcgcccatc aaggcgtgga gcctgcggtc acgtacgaca acctgggcct ccctccagag    960
tggtacgggg ccgtggagtg ggtcttccca acctgggcta gaacgcacgc tctcgacacc   1020
ggccaggctg tcaacctcct gaagggggcc atcgttaccg tggatcgcat cctcacggtg   1080
tccaagggct acgcttggga ggtcaccacg cctgaggggg gctacggcct ccacgagctc   1140
ctgacctcaa ggaaggcggt tatcaacggc atcacgaacg ggatcgacgt gtctgagtgg   1200
gatcaatcgt cagacgagca catcccattc cattacagcg ccgaggatct gtcgggcaag   1260
gtgcaatgca agatcgcgct ccagaaggag ctgagcctcc ctatccggcc agactgcccg   1320
ctgatcggct tcatcgggag actcgattac caaaagggca tcgacgtgat caggctggct   1380
accctgagc tcatgggcga ggatgttcag ctcgtgatgc tcgggagcgg caaccctgag   1440
gacgaggagt ggatgcgcgt catggagtcg acctacaggg ataagttccg cggctgggtt   1500
gggttcaacg tgccaatctc acaccgcatc accgcctctt gcgacatcct cctgatgcca   1560
tccagattcg agccttgcgg cctgaaccag ctctacgcga tgagatacgg cgctgtccct   1620
gtcgttcatg ggaccggggg cctgagggac acggttgaga acttcaaccc ttacgctggg   1680
gggggggtccg ggagggcac cgggtggacg ttctcgccac tctcaaagga caccatgctg   1740
gctgctctca gagtggctat ccggacgtac agagagcaca agccatcatg ggagcggctg   1800
atgaagagag gcatggagaa ggattacacc tgggacaagg ccgcgctgga gtacgagcaa   1860
gtgttcaagt gggctttcat cgaccccccc tacgtgtcct ga                     1902
```

<210> SEQ ID NO 4
<211> LENGTH: 633
<212> TYPE: PRT
<213> ORGANISM: Vitis vinifera

<400> SEQUENCE: 4

Met Glu Ser Leu Gln Ser Pro Leu Val Leu Ser Ser Lys Leu Leu Pro
1               5                   10                  15

Asn Ser Leu Lys Lys Pro Val Leu Glu Val Gly Phe Ala Cys Phe Phe
            20                  25                  30

Lys Gln Arg Arg Val Ile Gln Ser Val Ser Ile Lys Arg Ser Val Val
        35                  40                  45

Cys Cys Ser Arg Lys Gly Gly Gly Gly Ser Gln Asp Gly Ser Ser
    50                  55                  60

Ala Met Leu Val Asn Thr Asp Lys Lys Asp Ala Ser Asp Ser Val Gly
65                  70                  75                  80

Phe His Leu Val Pro Pro Pro Ser Gly Asp Asn Gly Val Ile Asp Pro

```
                     85                  90                  95
His Glu Lys Leu Ser Thr Gln Lys Glu Ala Glu Thr Gly Asn Ser Glu
                100                 105                 110

Gly Glu Glu Glu Arg Lys Thr Lys Val Thr Tyr Asn Ile Val Phe Val
                115                 120                 125

Thr Ser Glu Ser Ala Pro Tyr Ser Lys Thr Gly Gly Leu Gly Asp Val
                130                 135                 140

Cys Gly Ser Leu Pro Ile Ala Leu Ala Ala His Gly His Arg Val Met
145                 150                 155                 160

Val Val Ser Pro Arg Tyr Gln Asn Gly Thr Cys Ser Asp Glu Ile Phe
                165                 170                 175

Ser Gly Ala Ser Asp Leu Glu His Pro Ile Lys Val His Cys Phe Gly
                180                 185                 190

Gly Val Gln Glu Val Ser Phe Phe His Glu Tyr Arg Ala Gly Val Asp
                195                 200                 205

Trp Val Phe Val Asp His Pro Ser Tyr His Arg Pro Gly Asn Pro Tyr
                210                 215                 220

Gly Asp Gly Tyr Gly Ala Phe Gly Asp Asn Gln Phe Arg Phe Thr Leu
225                 230                 235                 240

Leu Cys His Ala Ala Cys Glu Ala Pro Leu Val Pro Leu Gly Gly
                245                 250                 255

Phe Thr Tyr Gly Glu Lys Cys Leu Phe Leu Val Asn Asp Trp His Ala
                260                 265                 270

Ser Leu Val Pro Val Leu Leu Ala Ala Lys Tyr Arg Pro His Gly Val
                275                 280                 285

Tyr Lys Asp Ala Arg Thr Val Leu Val Ile His Asn Leu Ala His Gln
                290                 295                 300

Gly Val Glu Pro Ala Val Thr Tyr Asp Asn Leu Gly Leu Pro Pro Glu
305                 310                 315                 320

Trp Tyr Gly Ala Val Glu Trp Val Phe Pro Thr Trp Ala Arg Thr His
                325                 330                 335

Ala Leu Asp Thr Gly Gln Ala Val Asn Leu Leu Lys Gly Ala Ile Val
                340                 345                 350

Thr Val Asp Arg Ile Leu Thr Val Ser Lys Gly Tyr Ala Trp Glu Val
                355                 360                 365

Thr Thr Pro Glu Gly Gly Tyr Gly Leu His Glu Leu Leu Thr Ser Arg
                370                 375                 380

Lys Ala Val Ile Asn Gly Ile Thr Asn Gly Ile Asp Val Ser Glu Trp
385                 390                 395                 400

Asp Pro Ser Ser Asp Glu His Ile Pro Phe His Tyr Ser Ala Glu Asp
                405                 410                 415

Leu Ser Gly Lys Val Gln Cys Lys Ile Ala Leu Gln Lys Glu Leu Ser
                420                 425                 430

Leu Pro Ile Arg Pro Asp Cys Pro Leu Ile Gly Phe Ile Gly Arg Leu
                435                 440                 445

Asp Tyr Gln Lys Gly Ile Asp Val Ile Arg Leu Ala Thr Pro Glu Leu
                450                 455                 460

Met Gly Glu Asp Val Gln Leu Val Met Leu Gly Ser Gly Asn Pro Glu
465                 470                 475                 480

Asp Glu Glu Trp Met Arg Val Met Glu Ser Thr Tyr Arg Asp Lys Phe
                485                 490                 495

Arg Gly Trp Val Gly Phe Asn Val Pro Ile Ser His Arg Ile Thr Ala
                500                 505                 510
```

Ser Cys Asp Ile Leu Leu Met Pro Ser Arg Phe Glu Pro Cys Gly Leu
    515                 520                 525

Asn Gln Leu Tyr Ala Met Arg Tyr Gly Ala Val Pro Val Val His Gly
    530                 535                 540

Thr Gly Gly Leu Arg Asp Thr Val Glu Asn Phe Asn Pro Tyr Ala Gly
545                 550                 555                 560

Gly Gly Ser Gly Glu Gly Thr Gly Trp Thr Phe Ser Pro Leu Ser Lys
                565                 570                 575

Asp Thr Met Leu Ala Ala Leu Arg Val Ala Ile Arg Thr Tyr Arg Glu
            580                 585                 590

His Lys Pro Ser Trp Glu Arg Leu Met Lys Arg Gly Met Glu Lys Asp
        595                 600                 605

Tyr Thr Trp Asp Lys Ala Ala Leu Glu Tyr Glu Gln Val Phe Lys Trp
    610                 615                 620

Ala Phe Ile Asp Pro Pro Tyr Val Ser
625                 630

<210> SEQ ID NO 5
<211> LENGTH: 1950
<212> TYPE: DNA
<213> ORGANISM: Poplar triocarpa
<220> FEATURE:
<221> NAME/KEY: misc_feature
<222> LOCATION: (1)..(1950)
<223> OTHER INFORMATION: Codon optimized cDNA sequence

<400> SEQUENCE: 5

```
atggagtctc tctgcatcgt tgggaacggg ggggttagca cctgccaggc tttcacgagg     60
ctggacacca cgagggtcgg cttcaggcct agagctcaac tgggcttcgg gtgcttcgtc    120
cgggagagat acaagtacgg caacctcgtt atcgcccgct cagggcgctc tgaagtgggc    180
aacagcaagg acgggaactt cgcggtggag aacgagaaga aggagaagag aggcgggctc    240
atcctgggcc ctgagagaga ctccagcggg tcgatcatcg gcttcaacct gatcccaccg    300
tccggcatgg acatcagctt caccgtcctc gagtcacacg aggatgctac cacgggcggg    360
acggaggagg ctgaggacat cgagggcgtg agaaggtcc agaccagggt gacgtacaac    420
atcgtcttcg ttacctcgga ggctgctcct tactcaaaga cgggcgggct cggggacgtc    480
tgcggcagcc tgcctatcgt tctcgctgct agaggccaca gagtcatggt ggtctctcct    540
cgctacctgc atggctcccc agcggacaag aacttcgcgg gggcttcgga gctcgattgc    600
cacatcaagg tctactgctt cggcggggag caagaggttg ccttcttcca tgagtaccgg    660
gagggcgtgg actgggtgtt cgtcgatcac ccaagctacc ataggcctgg aaacccttac    720
ggcgactcga gagggctttc ggcgataaca cagttccggt cgctctcct gtgccacgct    780 gcttgcgagg ctcctctcgt cctgccactc ggcgggtaca cctacggcga aagtgcctg    840 ttcctcgtta cgactggca tgctggcctg gttcctgtgc tcctggctag caagtacaga    900
ccctacggcg tgtacaagga cgcgaggacc atcctggtca tccacaacct cgctcatcaa    960
ggcgttgagc tgccgcgac ctacacgaac ctgggcctcc catccgagtg gtacggggct   1020
ctgggctggg tcttccctac ctgggctaga acgcacgctc tcgataccgg cgaggctgtg   1080
aacctcctga aggggctat cgtcaccgtt gaccgcatcc tcacggtgtc taagggctac   1140
gcttgggaga tcaccacggt cgagggcggc tacggcctgc acgagctcct gtcgtcaagg   1200
cgctccgtgc tcaacgggat caccaacggc atcgacatct acgagtggaa cccatcttcc   1260
```

```
gataagcata tcgcttccaa ctacagcgtg gacgatctgt ccggcaaggt ccaatgcaag    1320
atcgccctcc agaaggagct gggcctccca atcaagccgg actgccctct gatcgggttc    1380
atcggcagac tcgactacca aaagggcatc gatctcatca gatgggctac ccctgagctc    1440
ctggaggacg atgttcagtt cgtgatgctg ggctcagggg acccctcta cgaggattgg    1500 atgagagcca ccgagtctac gtacaaggat aagttcaggg ggtgggtggg cttcaacatc    1560
cctatctccc acaagatcac cgctggcgct gacatcctcc tgatgcctag cagattcgag    1620
ccttgcggcc tgaaccaact ctacgcgatg cggtacggca ccgttccagt tgtgcatggg    1680
accggcgggc tcagagacac ggtgcaggcc ttcgatcctt actcaaaggg cgggctgggc    1740
gaggggaccg gctggatctt ctcgccactc tcaaaggagt ctatgctggc tgccctcagg    1800
gtcgcgatca tgacctaccg cgatcacaag agctcgtggg agggcatcat gaagaggggg    1860
atggtgaagg actccacgtg ggagaacgcc gctgtccatt acgagcaggt gttcgagtgg    1920
gctttcatcg acccgccata catcaactga                                     1950

<210> SEQ ID NO 6
<211> LENGTH: 649
<212> TYPE: PRT
<213> ORGANISM: Poplar triocarpa

<400> SEQUENCE: 6

Met Glu Ser Leu Cys Ile Val Gly Asn Gly Val Ser Thr Cys Gln
1               5                   10                  15

Ala Phe Thr Arg Leu Asp Thr Thr Arg Val Gly Phe Arg Pro Arg Ala
            20                  25                  30

Gln Leu Gly Phe Gly Cys Phe Val Arg Glu Arg Tyr Lys Tyr Gly Asn
        35                  40                  45

Leu Val Ile Ala Arg Ser Gly Arg Ser Glu Val Gly Asn Ser Lys Asp
    50                  55                  60

Gly Asn Phe Ala Val Glu Asn Glu Lys Lys Glu Lys Arg Gly Gly Leu
65                  70                  75                  80

Ile Leu Gly Pro Glu Arg Asp Ser Ser Gly Ser Ile Ile Gly Phe Asn
                85                  90                  95

Leu Ile Pro Pro Ser Gly Met Asp Ile Ser Phe Thr Val Leu Glu Ser
            100                 105                 110

His Glu Asp Ala Thr Thr Gly Gly Thr Glu Glu Ala Glu Asp Ile Glu
        115                 120                 125

Gly Val Glu Lys Val Gln Thr Arg Val Thr Tyr Asn Ile Val Phe Val
    130                 135                 140

Thr Ser Glu Ala Ala Pro Tyr Ser Lys Thr Gly Gly Leu Gly Asp Val
145                 150                 155                 160

Cys Gly Ser Leu Pro Ile Val Leu Ala Ala Arg Gly His Arg Val Met
                165                 170                 175

Val Val Ser Pro Arg Tyr Leu His Gly Ser Pro Ala Asp Lys Asn Phe
            180                 185                 190

Ala Gly Ala Ser Glu Leu Asp Cys His Ile Lys Val Tyr Cys Phe Gly
        195                 200                 205

Gly Glu Gln Glu Val Ala Phe Phe His Glu Tyr Arg Glu Gly Val Asp
    210                 215                 220

Trp Val Phe Val Asp His Pro Ser Tyr His Arg Pro Gly Asn Pro Tyr
225                 230                 235                 240

Gly Asp Ser Arg Gly Ala Phe Gly Asp Asn Gln Phe Arg Phe Ala Leu
                245                 250                 255
```

-continued

Leu Cys His Ala Ala Cys Glu Ala Pro Leu Val Leu Pro Leu Gly Gly
             260                 265                 270

Tyr Thr Tyr Gly Glu Lys Cys Leu Phe Leu Val Asn Asp Trp His Ala
         275                 280                 285

Gly Leu Val Pro Val Leu Leu Ala Ser Lys Tyr Arg Pro Tyr Gly Val
         290                 295                 300

Tyr Lys Asp Ala Arg Thr Ile Leu Val Ile His Asn Leu Ala His Gln
305                 310                 315                 320

Gly Val Glu Pro Ala Ala Thr Tyr Thr Asn Leu Gly Leu Pro Ser Glu
                 325                 330                 335

Trp Tyr Gly Ala Leu Gly Trp Val Phe Pro Thr Trp Ala Arg Thr His
             340                 345                 350

Ala Leu Asp Thr Gly Glu Ala Val Asn Leu Leu Lys Gly Ala Ile Val
         355                 360                 365

Thr Val Asp Arg Ile Leu Thr Val Ser Lys Gly Tyr Ala Trp Glu Ile
370                 375                 380

Thr Thr Val Glu Gly Gly Tyr Gly Leu His Glu Leu Leu Ser Ser Arg
385                 390                 395                 400

Arg Ser Val Leu Asn Gly Ile Thr Asn Gly Ile Asp Ile Tyr Glu Trp
                 405                 410                 415

Asn Pro Ser Ser Asp Lys His Ile Ala Ser Asn Tyr Ser Val Asp Asp
             420                 425                 430

Leu Ser Gly Lys Val Gln Cys Lys Ile Ala Leu Gln Lys Glu Leu Gly
         435                 440                 445

Leu Pro Ile Lys Pro Asp Cys Pro Leu Ile Gly Phe Ile Gly Arg Leu
450                 455                 460

Asp Tyr Gln Lys Gly Ile Asp Leu Ile Arg Trp Ala Thr Pro Glu Leu
465                 470                 475                 480

Leu Glu Asp Asp Val Gln Phe Val Met Leu Gly Ser Gly Asp Pro Leu
                 485                 490                 495

Tyr Glu Asp Trp Met Arg Ala Thr Glu Ser Thr Tyr Lys Asp Lys Phe
             500                 505                 510

Arg Gly Trp Val Gly Phe Asn Ile Pro Ile Ser His Lys Ile Thr Ala
         515                 520                 525

Gly Ala Asp Ile Leu Leu Met Pro Ser Arg Phe Glu Pro Cys Gly Leu
530                 535                 540

Asn Gln Leu Tyr Ala Met Arg Tyr Gly Thr Val Pro Val Val His Gly
545                 550                 555                 560

Thr Gly Gly Leu Arg Asp Thr Val Gln Ala Phe Asp Pro Tyr Ser Lys
                 565                 570                 575

Gly Gly Leu Gly Glu Gly Thr Gly Trp Ile Phe Ser Pro Leu Ser Lys
             580                 585                 590

Glu Ser Met Leu Ala Ala Leu Arg Val Ala Ile Met Thr Tyr Arg Asp
         595                 600                 605

His Lys Ser Ser Trp Glu Gly Ile Met Lys Arg Gly Met Val Lys Asp
610                 615                 620

Ser Thr Trp Glu Asn Ala Ala Val His Tyr Glu Gln Val Phe Glu Trp
625                 630                 635                 640

Ala Phe Ile Asp Pro Pro Tyr Ile Asn
                 645

<210> SEQ ID NO 7
<211> LENGTH: 1890

<210> SEQ ID NO 7
<211> LENGTH: 1890
<212> TYPE: DNA
<213> ORGANISM: Sorghum bicolor
<220> FEATURE:
<221> NAME/KEY: misc_feature
<222> LOCATION: (1)..(1890)
<223> OTHER INFORMATION: Codon optimized cDNA sequence

<400> SEQUENCE: 7

```
atggctacgc cttccgctgt cggggctgct tgcctggttc tggctcgggc tgctgctggg      60
ctggggctcg ggccggggag ggggggcgac agagctaggc ctaggagatt ccaaagagtg     120
gtccggagac gctgcgtggc tgagctgagc agagagggcc ctgctccaac cccgaggcct     180
ctcccacctg ctctcctggc tcctcctctg gtcccagctt cctcgctcc acctagcgag      240
cctgagggcg agcctgcgtc gacccccct ccactgcctg acgctggcct cggggatctc      300
ggcctgcaac ctgagggcat cgctgagggg tccatcgacg agacggttgt ggtcgcgagc     360
gagcaggatt cggagatcgt tgtgggcaag gagcaagcca gggcgaaggt gacccagtcc     420
atcgtgttcg tcacgggcga ggcgtcgcca tacgctaagt caggcgggct gggcgacgtt     480
tgcgggagcc tgcctgtggc tctcgctgct agaggccacc gggtcatggt cgttatgccc     540
agatacctca cgggacctc cgacaagaac tacgctaacg ccttctacac ggagaagcat      600
atccgcatcc catgcttcgg cggggagcac gaggtcacct tcttccatga gtaccgcgac     660
tcagttgatt gggttttcgt ggaccaccca tcttaccatc ggccgggcaa cctctacggg     720
gacaagttcg gcgccttcgg ggataaccaa ttccgctaca ccctcctgtg ctacgctgct     780
tgcgaggctc cactcgtgct ggagctcggc gggtacatct acggccagaa ctgcatgttc     840
gtggtcaacg actggcacgc ttcgctcgtc ccagttctcc tggctgctaa gtaccgcccg     900
tacgcgtct acaaggattc gcggtcaatc tggttatcc acaacctcgc tcatcaaggc      960
gtggagcctg cttaaccta ccctgacctg ggcctcctc ctgagtggta cggggccctc      1020
gagtgggtgt tcccagagtg ggctagaaga cacgctctgg acaagggcga ggcggtcaac    1080
ttcctcaagg gggctgttgt gaccgccgat cgcatcgtga cggtctcaaa gggctactct    1140
tgggaggtga ccacggctga gggcgggcag gggctgaacg agctcctgtc cagccggaag    1200
tccgtgctca acggcatcgt caacgggatc gacatcaacg attggaaccc cgccaccgac    1260
aagtgcatcc cttgccacta ctctgtggac gatctgtccg gcaaggcgaa gtgcaagagc    1320
gctctccaaa aggagctggg cctccctatc agaccagagg tcccgctgat cggcttcatc    1380
gggaggctcg actaccaaaa gggcatcgat ctgatccagc tcatcatccc gcatctcatg    1440
cgcgacgatg tccagttcgt tatgctgggc tcggggacc ccgagctcga ggattggatg    1500
cgctctaccg agtccgactt caaggataag ttccgggct gggtgggtt ctccgttcca      1560
gtgagccaca gaatcacggc cggctgcgac atcctcctga tgccatccag gttcgagccg    1620
tgcggcctga ccaactcta cgccatgcag tacgggaccg tgcctgtcgt tcatgctacc    1680
ggcgggctga gggacacggt cgagaacttc aacccttttcg gcgagaacgg ggagcagggc    1740
accgggtggg ctttcgctcc actcaccacg gagaacatgt tcgtcgacat cgccaactgc    1800
aacttcgata tccaaggcgc gcagatcttc ctgggcaggg cgcacgagga ggggcatgtg    1860
aagcggctcc acgtcgggcc ttgcaggtga                                     1890
```

<210> SEQ ID NO 8
<211> LENGTH: 629
<212> TYPE: PRT
<213> ORGANISM: Sorghum bicolor

<400> SEQUENCE: 8

```
Met Ala Thr Pro Ser Ala Val Gly Ala Ala Cys Leu Val Leu Ala Arg
1               5                   10                  15

Ala Ala Ala Gly Leu Gly Leu Gly Pro Gly Arg Gly Gly Asp Arg Ala
            20                  25                  30

Arg Pro Arg Arg Phe Gln Arg Val Arg Arg Cys Val Ala Glu
        35                  40                  45

Leu Ser Arg Glu Gly Pro Ala Pro Thr Pro Arg Pro Leu Pro Pro Ala
    50                  55                  60

Leu Leu Ala Pro Pro Leu Val Pro Ala Phe Leu Ala Pro Pro Ser Glu
65                  70                  75                  80

Pro Glu Gly Glu Pro Ala Ser Thr Pro Pro Leu Pro Asp Ala Gly
                85                  90                  95

Leu Gly Asp Leu Gly Leu Gln Pro Glu Gly Ile Ala Glu Gly Ser Ile
            100                 105                 110

Asp Glu Thr Val Val Val Ala Ser Glu Gln Asp Ser Glu Ile Val Val
            115                 120                 125

Gly Lys Glu Gln Ala Arg Ala Lys Val Thr Gln Ser Ile Val Phe Val
130                 135                 140

Thr Gly Glu Ala Ser Pro Tyr Ala Lys Ser Gly Gly Leu Gly Asp Val
145                 150                 155                 160

Cys Gly Ser Leu Pro Val Ala Leu Ala Ala Arg Gly His Arg Val Met
                165                 170                 175

Val Val Met Pro Arg Tyr Leu Asn Gly Thr Ser Asp Lys Asn Tyr Ala
            180                 185                 190

Asn Ala Phe Tyr Thr Glu Lys His Ile Arg Ile Pro Cys Phe Gly Gly
        195                 200                 205

Glu His Glu Val Thr Phe Phe His Glu Tyr Arg Asp Ser Val Asp Trp
    210                 215                 220

Val Phe Val Asp His Pro Ser Tyr His Arg Pro Gly Asn Leu Tyr Gly
225                 230                 235                 240

Asp Lys Phe Gly Ala Phe Gly Asp Asn Gln Phe Arg Tyr Thr Leu Leu
                245                 250                 255

Cys Tyr Ala Ala Cys Glu Ala Pro Leu Val Leu Glu Leu Gly Gly Tyr
            260                 265                 270

Ile Tyr Gly Gln Asn Cys Met Phe Val Val Asn Asp Trp His Ala Ser
        275                 280                 285

Leu Val Pro Val Leu Leu Ala Ala Lys Tyr Arg Pro Tyr Gly Val Tyr
    290                 295                 300

Lys Asp Ser Arg Ser Ile Leu Val Ile His Asn Leu Ala His Gln Gly
305                 310                 315                 320

Val Glu Pro Ala Ser Thr Tyr Pro Asp Leu Gly Leu Pro Pro Glu Trp
                325                 330                 335

Tyr Gly Ala Leu Glu Trp Val Phe Pro Glu Trp Ala Arg Arg His Ala
            340                 345                 350

Leu Asp Lys Gly Glu Ala Val Asn Phe Leu Lys Gly Ala Val Val Thr
        355                 360                 365

Ala Asp Arg Ile Val Thr Val Ser Lys Gly Tyr Ser Trp Glu Val Thr
    370                 375                 380

Thr Ala Glu Gly Gly Gln Gly Leu Asn Glu Leu Leu Ser Ser Arg Lys
385                 390                 395                 400

Ser Val Leu Asn Gly Ile Val Asn Gly Ile Asp Ile Asn Asp Trp Asn
                405                 410                 415
```

```
Pro Ala Thr Asp Lys Cys Ile Pro Cys His Tyr Ser Val Asp Asp Leu
            420                 425                 430

Ser Gly Lys Ala Lys Cys Lys Ser Ala Leu Gln Lys Glu Leu Gly Leu
            435                 440                 445

Pro Ile Arg Pro Glu Val Pro Leu Ile Gly Phe Ile Gly Arg Leu Asp
            450                 455                 460

Tyr Gln Lys Gly Ile Asp Leu Ile Gln Leu Ile Ile Pro His Leu Met
465                 470                 475                 480

Arg Asp Asp Val Gln Phe Val Met Leu Gly Ser Gly Asp Pro Glu Leu
                    485                 490                 495

Glu Asp Trp Met Arg Ser Thr Glu Ser Asp Phe Lys Asp Lys Phe Arg
            500                 505                 510

Gly Trp Val Gly Phe Ser Val Pro Val Ser His Arg Ile Thr Ala Gly
            515                 520                 525

Cys Asp Ile Leu Leu Met Pro Ser Arg Phe Glu Pro Cys Gly Leu Asn
            530                 535                 540

Gln Leu Tyr Ala Met Gln Tyr Gly Thr Val Pro Val Val His Ala Thr
545                 550                 555                 560

Gly Gly Leu Arg Asp Thr Val Glu Asn Phe Asn Pro Phe Gly Glu Asn
                    565                 570                 575

Gly Glu Gln Gly Thr Gly Trp Ala Phe Ala Pro Leu Thr Thr Glu Asn
            580                 585                 590

Met Phe Val Asp Ile Ala Asn Cys Asn Phe Asp Ile Gln Gly Ala Gln
            595                 600                 605

Ile Phe Leu Gly Arg Ala His Glu Glu Gly His Val Lys Arg Leu His
            610                 615                 620

Val Gly Pro Cys Arg
625

<210> SEQ ID NO 9
<211> LENGTH: 649
<212> TYPE: PRT
<213> ORGANISM: Amaranthus cruentus

<400> SEQUENCE: 9

Met Glu Ser Leu Phe Leu Gln Ser Phe His Met Lys Gly Leu Cys Arg
1               5                   10                  15

Ser Lys Leu Asn Phe Gly Ser Ser Pro Leu Gln Ile Arg Gly Asn Asn
            20                  25                  30

Gln Val Gly Ile Ser Cys Leu Trp Lys Gln Arg Ser Arg Thr Trp Ser
            35                  40                  45

Asn Phe Ser Ile Lys Cys Gln Thr Phe Ser Asp Gly Asn Glu Gly Arg
50                  55                  60

Val Ser Ser Thr Asp Gly Ser Leu Val Ile Glu Ser Gln Arg Gly
65                  70                  75                  80

Gly Asp Glu Glu Lys Lys Gly Ser Leu Leu Gly Pro Val Lys Asp Ala
                    85                  90                  95

Ser Gly Ser Ile Val Gly Phe Glu Leu Phe Ser Gln Ser Val Gly Asn
            100                 105                 110

Gly Asn Asp Val Asp Glu Glu Leu Glu Glu Glu Thr Val Tyr Glu Gly
            115                 120                 125

Gln Asp Lys Leu Leu Thr Lys Lys Met Ser Ile Ile Phe Val Thr
            130                 135                 140

Ser Glu Ala Ala Pro Tyr Ser Lys Thr Gly Gly Leu Gly Asp Val Cys
```

```
            145                 150                 155                 160
Gly Ser Leu Pro Ile Ser Leu Ala Glu Arg Gly His Arg Val Met Val
                165                 170                 175
Val Ser Pro Arg Tyr Ile His Gly Thr Ala Asp Lys Val Tyr Ala
            180                 185                 190
Gly Ala Phe Asp Ala Asn Cys Arg Ile Lys Val Asn Cys Phe Gly Gly
        195                 200                 205
Pro Gln Glu Val Ala Phe Phe His Glu Tyr Lys Asn Gly Val Asp Trp
    210                 215                 220
Val Phe Val Asp His Leu Ser Tyr His Arg Pro Gly Asn Pro Tyr Gly
225                 230                 235                 240
Asp Ser Tyr Gly Ala Phe Gly Asp Asn Gln Phe Arg Phe Thr Leu Leu
                245                 250                 255
Cys His Ala Ala Cys Glu Ala Pro Leu Val Leu Pro Leu Gly Gly Tyr
            260                 265                 270
Thr Tyr Gly Asp Lys Cys Met Phe Val Val Asn Asp Trp His Ala Gly
        275                 280                 285
Leu Val Pro Val Leu Leu Ala Ala Asn Tyr Arg Pro Tyr Gly Val Tyr
    290                 295                 300
Lys Asp Ala Arg Ser Val Leu Val Ile His Asn Leu Ser His Gln Gly
305                 310                 315                 320
Val Glu Ala Ala Leu Thr Tyr Glu Asn Leu Gly Leu Pro Pro Gln Trp
                325                 330                 335
Tyr Gly Ala Leu Glu Trp Val Phe Pro Glu Trp Ala Arg Ala His Ala
            340                 345                 350
Leu Asp Lys Gly Glu Ala Val Asn Ile Leu Lys Gly Ala Ile Val Thr
        355                 360                 365
Ser Asp Arg Ile Leu Thr Val Ser Gln Gly Tyr Ser Trp Glu Ile Thr
    370                 375                 380
Thr Val Glu Gly Gly Tyr Gly Leu His Asp Leu Leu Thr Ser Arg Lys
385                 390                 395                 400
Phe Val Leu Asn Gly Ile Ile Asn Gly Ile Asn Val Asn Glu Trp Asp
                405                 410                 415
Pro Ser Asn Asp Pro Leu Ile Ala Ala Pro Tyr Ser Val Asp Asp Leu
            420                 425                 430
Ser Gly Lys Ala Glu Cys Lys Ala Ala Leu Gln Lys Glu Leu Gly Leu
        435                 440                 445
Pro Ile Lys Pro Asp Cys Pro Leu Ile Gly Phe Ile Gly Arg Leu Asp
    450                 455                 460
Tyr Gln Lys Gly Ile Asp Val Ile Gln Glu Ala Phe Pro Gln Leu Met
465                 470                 475                 480
Glu Asp Asp Val Gln Phe Val Met Leu Gly Ser Gly Asp Ser Arg Tyr
                485                 490                 495
Glu Ser Trp Met Arg Ala Ala Glu Gly Ala Cys Lys Asp Lys Phe Arg
            500                 505                 510
Gly Trp Val Gly Phe Ser Val Pro Ile Ser His Arg Ile Thr Ala Gly
        515                 520                 525
Cys Asp Ile Leu Leu Met Pro Ser Arg Phe Glu Pro Cys Gly Leu Asn
    530                 535                 540
Gln Leu Tyr Ala Met Arg Tyr Gly Thr Ile Pro Ile Val His Asn Thr
545                 550                 555                 560
Gly Gly Leu Arg Asp Thr Val Glu Thr Tyr Asn Pro Phe Ala Val Gly
                565                 570                 575
```

```
Pro Asp Gly Thr Gly Thr Gly Thr Gly Trp Ala Phe Ser Pro Leu Thr
            580                 585                 590

Lys Glu Ser Met Leu Ser Ala Leu Ser Asn Ala Val Arg Thr Tyr Arg
        595                 600                 605

Asp Tyr Lys Glu Ser Trp Ala Gly Leu Met Lys Arg Gly Met Gln Gln
        610                 615                 620

Asp Phe Thr Trp Asp Thr Ala Ala Gln Tyr Glu Gln Val Phe Glu
625                 630                 635                 640

Trp Ala Leu Ile Asp Pro Pro Tyr Cys
                645

<210> SEQ ID NO 10
<211> LENGTH: 645
<212> TYPE: PRT
<213> ORGANISM: Phaseolus vulgaris

<400> SEQUENCE: 10

Met Asp Ser Leu Gln Leu His Ala Leu Leu Pro His Leu Cys Ala
1               5                   10                  15

Ser Ser Ser Ser Pro Ser Leu Arg Gln Leu Arg Phe Pro Leu Pro Leu
                20                  25                  30

Ile Arg Asn Ser Arg Asn Arg Asn Phe Arg Leu Phe Ser Ala His Asn
            35                  40                  45

Gly Gly Ala Ala Ser Gln Asp Gly Pro Phe Ala Phe Glu Glu Lys Val
        50                  55                  60

Val Ser Ser Pro Lys Asp Asp Arg Gly Leu Val Leu Ala Arg Glu Thr
65                  70                  75                  80

Asp Asp Phe Gly Tyr Leu Val Gly Phe Arg Leu Ile Pro Glu Ser Gly
                85                  90                  95

Leu Glu Glu Leu Met Ser Val Gln His Ala Ile Ala Glu Glu Asp Ser
            100                 105                 110

Ser Ser Asp Leu Ala Lys Lys Pro Gly Ile Lys Asp Thr Gly Glu Glu
        115                 120                 125

Glu Ala Glu Thr Arg Val Ser His Asn Ile Ile Phe Val Thr Ala Glu
130                 135                 140

Ala Ala Pro Tyr Ser Lys Thr Gly Gly Leu Ala Asp Val Cys Gly Ser
145                 150                 155                 160

Leu Pro Ile Ala Leu Ala Ala Arg Gly His Arg Val Met Val Val Thr
                165                 170                 175

Pro Arg Tyr Ile His Gly Thr Ser Glu Asp Ala Lys Phe Ala Gly Ala
            180                 185                 190

Val Asp Leu Glu Gln Arg Thr Lys Val Ser Cys Phe Gly Gly Ala Gln
        195                 200                 205

Glu Val Gly Phe Phe His Glu Tyr Arg Glu Gly Val Asp Trp Val Phe
210                 215                 220

Val Asp His Pro Ser Phe His Arg Pro Gly Asn Pro Tyr Gly Asp Lys
225                 230                 235                 240

Phe Gly Thr Phe Gly Asp Asn Gln Phe Arg Phe Thr Leu Leu Ser His
                245                 250                 255

Ala Ala Cys Glu Ala Pro Leu Val Leu Pro Leu Gly Phe Thr Tyr
            260                 265                 270

Gly Glu Lys Cys Leu Phe Leu Ala Asn Asp Trp His Ala Ser Leu Val
        275                 280                 285

Pro Val Leu Leu Ala Ala Lys Tyr Arg Pro His Gly Val Tyr Arg Asp
```

```
                290                 295                 300
Ala Arg Ser Ile Leu Val Ile His Asn Ile Ala His Gln Gly Val Glu
305                 310                 315                 320

Pro Ala Ile Thr Tyr Ser Ser Leu Gly Leu Pro Thr Glu Trp Tyr Gly
                325                 330                 335

Ala Leu Glu Trp Val Phe Pro Thr Trp Ala Arg Thr His Ala Leu Asp
                340                 345                 350

Thr Gly Glu Ala Val Asn Phe Leu Lys Gly Ala Val Val Thr Ala Asp
                355                 360                 365

Arg Ile Val Thr Val Ser Lys Gly Tyr Ser Trp Glu Ile Thr Thr Ser
                370                 375                 380

Glu Gly Gly Asn Gly Leu His Glu Leu Leu Asn Gly Arg Lys Ser Ile
385                 390                 395                 400

Leu Ser Gly Ile Thr Asn Gly Ile Asp Val Thr Glu Trp Asp Pro Ser
                405                 410                 415

Cys Asp Lys His Ile Ala Phe Asn Tyr Ser Ala Asp Asp Leu Ser Gly
                420                 425                 430

Lys Ala Lys Cys Lys Tyr Ala Leu Gln Lys Glu Leu Gly Leu Pro Val
                435                 440                 445

Arg Ser Asp Cys Pro Leu Ile Gly Phe Ile Gly Arg Leu Asp Tyr Gln
                450                 455                 460

Lys Gly Ile Asp Leu Ile Arg Leu Ala Met Pro Glu Leu Met Glu Ala
465                 470                 475                 480

Asp Val Gln Phe Val Met Leu Gly Ser Gly Asn Pro Ile Tyr Glu Asp
                485                 490                 495

Trp Met Arg Ala Thr Glu Ser Val Tyr Arg Asp Lys Phe Arg Gly Trp
                500                 505                 510

Val Gly Phe Asn Val Pro Ile Ser His Lys Ile Thr Ala Gly Cys Asp
                515                 520                 525

Ile Leu Leu Met Pro Ser Ala Phe Glu Pro Cys Gly Leu Asn Gln Leu
530                 535                 540

Tyr Ala Met Arg Tyr Gly Thr Ile Pro Val Val His Glu Thr Gly Gly
545                 550                 555                 560

Leu Arg Asp Thr Val His Asn Phe Ser Pro Tyr Thr Glu Asp Ser Lys
                565                 570                 575

Ala Glu Ser Thr Gly Trp Thr Phe Ser Pro Leu Thr Lys Glu Ser Met
                580                 585                 590

Leu Thr Ala Leu Arg Tyr Ala Ile Gln Thr Tyr Asn Glu His Lys Ser
                595                 600                 605

Ser Trp Glu Gly Leu Met Leu Arg Gly Met Thr Lys Asp Tyr Thr Trp
                610                 615                 620

Val Asn Ala Ala Thr Gln Tyr Glu Gln Ile Ile Glu Trp Ala Phe Ile
625                 630                 635                 640

Gly Pro Pro Tyr Cys
                645

<210> SEQ ID NO 11
<211> LENGTH: 525
<212> TYPE: PRT
<213> ORGANISM: Ostreococcus tauri

<400> SEQUENCE: 11

Met Asn Ile Val Phe Val Ser Ser Glu Val Ala Pro Trp Ser Lys Thr
1               5                   10                  15
```

-continued

```
Gly Gly Leu Gly Asp Val Cys Gly Ala Leu Pro Gln Ala Leu Val Ala
            20                  25                  30

Arg Gly His Arg Val Met Val Ile Ser Pro Lys Tyr Gln Asn Gly Ser
        35                  40                  45

Lys Ala Asp Ala Leu Tyr Asn Gly Ala Leu Asp Thr Cys Thr Arg Ala
 50                  55                  60

Lys Ile Gly Cys Phe Gly Ala Glu His Glu Val Gly Phe Phe His Gln
 65                  70                  75                  80

Ile Lys Asn Gly Val Asp Tyr Val Phe Val Asp His Ala Ser Phe His
                85                  90                  95

Arg Lys Gly Ser Leu Tyr Gly Asp Ser Phe Gly Val Tyr Gly Asp Asn
            100                 105                 110

Gln Phe Arg Phe Thr Leu Leu Ala His Ala Ala Cys Glu Ala Pro Leu
        115                 120                 125

Gln Leu Ala Phe Glu Gly Cys Gly Asp Arg Tyr Gly Lys Asp Ile Val
130                 135                 140

Phe Val Ala Asn Asp Trp His Ala Gly Leu Val Pro Thr Leu Val Ala
145                 150                 155                 160

Ser Lys Tyr Arg Pro His Gly Val Tyr Arg Asp Ala Arg Thr Ile Cys
                165                 170                 175

Ala Ile His Asn Ile Phe His Gln Gly Val Glu Pro Ser Thr Thr Phe
            180                 185                 190

Pro Cys Leu Gly Val Pro Thr Glu Trp Tyr Gly Ala Leu Glu Tyr Gln
        195                 200                 205

Tyr Pro His His Met Arg Ala His Glu Leu Asp Glu Gly Arg Val Val
210                 215                 220

Asn Ile Leu Lys Gly Ala Ile Ala Thr Ser Asp Arg Val Leu Thr Val
225                 230                 235                 240

Ser Gln Gly Tyr Ala Tyr Glu Ile Thr Thr Pro Glu Gly Gly Lys Gly
                245                 250                 255

Met Glu Gly Leu Leu Leu Ser Arg Ala Asn Lys Leu Asp Gly Ile Ala
            260                 265                 270

Asn Gly Ile Asp Met Asp Glu Trp Asn Pro Glu Ala Asp Pro Asp Cys
        275                 280                 285

Ala Ala Pro Tyr Ser Val Ile Asp Leu Ala Gly Lys Leu Glu Cys Lys
290                 295                 300

Arg Ala Leu Gln Lys Glu Leu Gly Leu Pro Glu Arg Asp Val Pro
305                 310                 315                 320

Leu Met Gly Phe Ile Gly Arg Leu Asp Trp Gln Lys Gly Pro Asp Leu
                325                 330                 335

Leu Gln Gln Ala Leu His Asp Met Met Arg Glu Asp Ile Gln Val Val
            340                 345                 350

Met Leu Gly Ser Gly Leu Pro Glu Leu Glu Asp Phe Met Arg Trp Ala
        355                 360                 365

Glu Gly Glu Tyr Lys Asp Lys Phe Arg Gly Trp Val Gly Phe Ser Val
370                 375                 380

Pro Met Ala His Arg Ile Thr Ala Gly Cys Asp Leu Leu Met Pro
385                 390                 395                 400

Ser Arg Phe Glu Pro Cys Gly Leu Asn Gln Leu Tyr Ala Met Arg Tyr
                405                 410                 415

Gly Thr Leu Pro Ile Ala His Ala Thr Gly Gly Leu Lys Asp Thr Ile
            420                 425                 430

Thr Pro His Asn Ala Phe Gly Asp Ala Asp Lys Val Leu Ala Gly Thr
```

```
                435                 440                 445
Ala Asp Val Asn Gln Gly Glu Gly Val Gly Thr Gly Trp Leu Phe Asn
450                 455                 460

Asp Met Asn Ala Asp Ala Leu Met Trp Ala Ile Arg Ser Ala Cys Asp
465                 470                 475                 480

Val Tyr Arg Ser Asp Lys Lys Phe Trp Arg Ala Met Gln Thr Gln Ala
                485                 490                 495

Met Thr Gln Asp Leu Ser Trp Asn Asn Ala Ala Arg Lys Trp Glu Gln
                500                 505                 510

Val Phe Glu Trp Ala Lys Met Asp Pro Pro His Cys Gly
                515                 520                 525

<210> SEQ ID NO 12
<211> LENGTH: 651
<212> TYPE: PRT
<213> ORGANISM: Glycine max

<400> SEQUENCE: 12

Met Glu Ser Leu Glu Leu Val Pro Leu Leu Leu Leu His Pro Pro
1               5                   10                  15

Pro Ser Gln Ser Phe Asn Asn Ser Arg Ser Ile Arg Gln Leu Arg Phe
                20                  25                  30

Pro Ser Leu Leu Asn Ser Lys Thr Arg Asn Ala Asn Leu Arg Ser Phe
            35                  40                  45

Ser Gly Asn Leu Gln Gly Gly Gly Ala Thr Ser Gln Asp Gly Pro
    50                  55                  60

Phe Ala Phe Glu Asp Gln Val Ser His His Lys Asp Asp Arg Ala Leu
65                  70                  75                  80

Val Leu Ala Arg Glu Thr Asp Asp Phe Gly Tyr Leu Val Gly Phe Arg
                85                  90                  95

Leu Leu Pro Asn Ser Gly Leu Glu Glu Phe Met Asn Val Ser His Ser
            100                 105                 110

Ile Thr Glu Glu Asp Ser Ser Ser Asp Glu Val Glu Lys Pro Lys Val
        115                 120                 125

Glu Asp Thr Glu Glu Glu Ala Lys Thr Arg Val Ser His Asn Ile
    130                 135                 140

Val Val Val Thr Ser Glu Ala Ala Pro Tyr Ser Lys Thr Gly Leu
145                 150                 155                 160

Ala Asp Val Cys Gly Ser Leu Pro Ile Ala Leu Ala Ser Arg Gly His
                165                 170                 175

Arg Val Met Val Val Thr Pro Arg Tyr Ile His Gly Thr Ser Glu Asp
                180                 185                 190

Leu Lys Phe Ala Gly Ala Val Asp Leu Asp Gln Ser Thr Lys Val Phe
            195                 200                 205

Cys Phe Gly Gly Ala Gln Glu Ile Gly Phe Tyr His Glu Tyr Arg Glu
        210                 215                 220

Gly Val Asp Trp Val Phe Val Asp His Pro Ser Phe His Arg Pro Gly
225                 230                 235                 240

Asn Pro Tyr Gly Asp Lys Phe Gly Thr Phe Gly Asp Asn Gln Phe Arg
                245                 250                 255

Phe Thr Leu Leu Cys His Ala Ala Cys Glu Ala Pro Leu Val Leu Pro
            260                 265                 270

Leu Gly Gly Phe Ser Tyr Gly Glu Lys Cys Leu Phe Leu Ala Asn Asp
        275                 280                 285
```

```
Trp His Ala Ser Leu Val Pro Ile Leu Ala Ala Lys Tyr Arg Pro
    290                 295                 300

His Gly Val Tyr Lys Asp Ala Arg Ser Ile Leu Val Ile His Asn Ile
305                 310                 315                 320

Ala His Gln Gly Val Glu Pro Ala Ile Thr Tyr Arg Asn Leu Gly Leu
                325                 330                 335

Pro Ser Glu Trp Tyr Gly Ala Leu Glu Trp Val Phe Pro Thr Trp Ala
            340                 345                 350

Arg Thr His Ala Leu Asp Thr Gly Glu Ala Val Asn Phe Leu Lys Gly
355                 360                 365

Ala Val Val Thr Ala Asp Arg Ile Val Thr Val Ser Lys Gly Tyr Ser
370                 375                 380

Trp Glu Ile Thr Thr Ser Glu Gly Gly Cys Gly Leu His Asp Leu Leu
385                 390                 395                 400

Ser Ser Arg Lys Ser Ile Leu Ser Gly Ile Thr Asn Gly Ile Asp Val
                405                 410                 415

Thr Glu Trp Asp Pro Ser Cys Asp Lys His Ile Ala Cys Asn Tyr Ser
            420                 425                 430

Ala Asp Asp Leu Ser Gly Lys Ala Glu Cys Lys Ile Ser Leu Gln Lys
        435                 440                 445

Glu Leu Gly Leu Pro Met Arg Pro Asp Cys Pro Met Ile Gly Phe Ile
450                 455                 460

Gly Arg Leu Asp Tyr Gln Lys Gly Ile Asp Leu Ile Arg Leu Ala Met
465                 470                 475                 480

Pro Glu Leu Met Glu Ala Asp Val Gln Phe Val Met Leu Gly Ser Gly
                485                 490                 495

Asn Pro Ile Tyr Glu Asp Trp Met Arg Ala Thr Glu Ser Ile Tyr Lys
            500                 505                 510

Asp Lys Phe Arg Gly Trp Val Gly Phe Asn Val Pro Ile Ser His Lys
        515                 520                 525

Ile Thr Ala Gly Cys Asp Ile Leu Leu Met Pro Ser Ala Phe Glu Pro
530                 535                 540

Cys Gly Leu Asn Gln Leu Tyr Ala Met Arg Tyr Gly Thr Ile Pro Val
545                 550                 555                 560

Val His Glu Thr Gly Gly Leu Arg Asp Thr Val His Asn Phe Asn Pro
                565                 570                 575

Tyr Ala Glu Glu Ser Arg Ala Glu Ser Thr Gly Trp Thr Phe Ser Pro
            580                 585                 590

Leu Thr Lys Glu Ser Met Leu Ala Ala Leu Arg Tyr Ala Ile Gln Thr
        595                 600                 605

Tyr Asn Glu Tyr Lys Ser Ser Trp Glu Gly Leu Met Ile Arg Gly Met
610                 615                 620

Thr Arg Asp Tyr Thr Trp Val Asn Ala Ala Thr Gln Tyr Glu Gln Val
625                 630                 635                 640

Ile Glu Trp Ala Phe Thr Asp Pro Pro Tyr Cys
                645                 650

<210> SEQ ID NO 13
<211> LENGTH: 655
<212> TYPE: PRT
<213> ORGANISM: Medicago truncatula

<400> SEQUENCE: 13

Met Glu Ser Leu Glu Leu Pro Arg Leu Phe Leu His His Pro Arg Ala
1               5                   10                  15
```

-continued

Ser Ser Ala Pro Thr Arg Pro His Pro His Ser Thr Asn Ser Ser
        20              25              30

Arg Phe Leu Pro Gln Phe Gly Phe Pro Ser Lys Leu Lys Asn Ala Thr
        35              40              45

Leu Arg Ser Ile Ser Val Ser Ser Gln Asp Gly Pro Ile Ser Phe Glu
50              55              60

Asp Glu Thr Gln Gln Leu Arg His Gln Asp Gln Glu Asp Glu Gly Arg
65              70              75              80

Leu Leu Ser Arg Glu Ile Asp Asp Phe Gly Ser Leu Val Ser Phe Arg
                85              90              95

Leu Thr Pro His Ser Ala Ser Ala Ser Ala Ser Gly Lys Thr Ala Glu
                100             105             110

Thr Gln Gly Asn Leu Arg Ser Asp Glu Val Glu Lys Pro Glu Ile Gly
        115             120             125

Asn Ala Glu Asp Glu Lys Ala Gln Thr Ile Val Thr Arg Asn Ile Val
130             135             140

Phe Val Thr Ser Glu Ala Ala Pro Tyr Ser Lys Thr Gly Gly Leu Ala
145             150             155             160

Asp Val Cys Gly Ser Leu Pro Ile Ala Leu Ala Gly Arg Gly His Arg
                165             170             175

Val Met Val Ile Ser Pro Arg Tyr Ile His Gly Thr Ala Ala Asp Ser
                180             185             190

Lys Phe Ser Gly Ala Val Asp Leu Gly Ser Pro Ile Asn Val Phe Cys
        195             200             205

Phe Gly Gly Ala Gln Glu Val Gly Phe Phe His Glu Tyr Arg Glu Gly
        210             215             220

Val Asp Trp Val Phe Val Asp His Pro Ser Phe His Arg Pro Gly Asn
225             230             235             240

Pro Tyr Gly Asp Lys His Gly Thr Phe Lys Asp Asn Gln Phe Arg Phe
                245             250             255

Thr Leu Leu Ser His Ala Ala Cys Glu Ala Pro Leu Val Leu Pro Leu
                260             265             270

Gly Gly Phe Thr Tyr Gly Glu Lys Cys Leu Phe Leu Val Asn Asp Trp
        275             280             285

His Ala Ser Leu Val Ser Val Leu Leu Ala Ser Lys Tyr Arg Pro Tyr
        290             295             300

Gly Val Tyr Lys Asp Ala Arg Ser Ile Leu Val Ile His Asn Ile Ala
305             310             315             320

His Gln Gly Val Glu Pro Ala Ile Thr Tyr Ser Asn Leu Gly Leu Pro
                325             330             335

Gln Glu Trp Tyr Gly Ala Leu Gly Trp Val Phe Pro Thr Trp Ala Arg
        340             345             350

Thr His Ala Leu Asp Thr Gly Glu Ala Val Asn Phe Leu Lys Gly Ala
        355             360             365

Ile Val Thr Ala Asp Arg Ile Val Thr Val Ser Lys Gly Tyr Ser Trp
        370             375             380

Glu Ile Thr Thr Thr Glu Gly Gly Phe Gly Leu Gln Glu Ile Leu Arg
385             390             395             400

Asp Arg Lys Ser Ile Leu Ser Gly Ile Thr Asn Gly Ile Asp Val Thr
                405             410             415

Glu Trp Asp Pro Ser Ser Asp Glu His Ile Ala Ser Ser Tyr Ser Ala
        420             425             430

```
Asp Asp Leu Ser Gly Lys Val Lys Cys Lys Ile Ala Leu Gln Lys Glu
            435                 440                 445

Leu Gly Leu Pro Val Arg Pro Asp Cys Pro Val Ile Gly Phe Val Gly
        450                 455                 460

Arg Leu Asp Tyr Gln Lys Gly Ile Asp Leu Ile Arg Gln Ala Ile Pro
465                 470                 475                 480

Glu Leu Met Gln Asp Asp Val Gln Phe Val Met Leu Gly Ser Gly Asn
                485                 490                 495

Pro Ile Tyr Glu Asp Trp Met Arg Ala Thr Glu Ser Leu Tyr Lys Asp
            500                 505                 510

Lys Phe Arg Gly Trp Val Gly Phe Asn Val Pro Val Ser His Arg Ile
        515                 520                 525

Thr Ala Gly Cys Asp Ile Leu Leu Met Pro Ser Thr Phe Glu Pro Cys
            530                 535                 540

Gly Leu Asn Gln Leu Tyr Ala Met Arg Tyr Gly Thr Ile Pro Val Val
545                 550                 555                 560

His Glu Thr Gly Gly Leu Arg Asp Thr Val Gln Asn Phe Asn Pro Phe
                565                 570                 575

Ala Gly Gly Ser Gly Ala Glu Gly Cys Asn Ala Glu Gly Thr Gly Trp
            580                 585                 590

Thr Phe Ser Pro Leu Thr Lys Glu Ser Met Leu Val Ala Leu Arg Tyr
        595                 600                 605

Ala Ile Gln Thr Tyr Asn Glu His Lys Ser Ser Trp Glu Gly Leu Met
            610                 615                 620

Lys Arg Gly Met Thr Arg Asp Tyr Thr Trp Glu Lys Ala Ala Ala Gln
625                 630                 635                 640

Tyr Glu Gln Ile Ile Glu Trp Ala Phe Met Asp Pro Pro Tyr Cys
                645                 650                 655

<210> SEQ ID NO 14
<211> LENGTH: 640
<212> TYPE: PRT
<213> ORGANISM: Zea mays

<400> SEQUENCE: 14

Met Ala Thr Pro Ser Ala Val Gly Ala Ala Cys Leu Leu Leu Ala Arg
1               5                   10                  15

Ala Ala Trp Pro Ala Ala Val Gly Asp Arg Ala Arg Pro Arg Arg Leu
            20                  25                  30

Gln Arg Val Leu Arg Arg Cys Val Ala Glu Leu Ser Arg Glu Gly
        35                  40                  45

Pro Ala Pro Arg Pro Leu Pro Pro Ala Leu Leu Ala Pro Pro Leu Val
    50                  55                  60

Pro Gly Phe Leu Ala Pro Ala Glu Pro Thr Gly Glu Pro Ala Ser
65                  70                  75                  80

Thr Pro Pro Pro Val Pro Asp Ala Gly Leu Gly Asp Leu Gly Leu Glu
                85                  90                  95

Pro Glu Gly Ile Ala Glu Gly Ser Ile Asp Asn Thr Val Val Ala
            100                 105                 110

Ser Glu Gln Asp Ser Glu Ile Val Val Gly Lys Glu Gln Ala Arg Ala
        115                 120                 125

Lys Val Thr Gln Ser Ile Val Phe Val Thr Gly Glu Ala Ser Pro Tyr
130                 135                 140

Ala Lys Ser Gly Gly Leu Gly Asp Val Cys Gly Ser Leu Pro Val Ala
145                 150                 155                 160
```

```
Leu Ala Ala Arg Gly His Arg Val Met Val Met Pro Arg Tyr Leu
            165                 170                 175

Asn Gly Thr Ser Asp Lys Asn Tyr Ala Asn Ala Phe Tyr Thr Glu Lys
            180                 185                 190

His Ile Arg Ile Pro Cys Phe Gly Gly Glu His Glu Val Thr Phe Phe
            195                 200                 205

His Glu Tyr Arg Asp Ser Val Asp Trp Val Phe Val Asp His Pro Ser
            210                 215                 220

Tyr His Arg Pro Gly Asn Leu Tyr Gly Asp Lys Phe Gly Ala Phe Gly
225                 230                 235                 240

Asp Asn Gln Phe Arg Tyr Thr Leu Leu Cys Tyr Ala Ala Cys Glu Ala
            245                 250                 255

Pro Leu Ile Leu Glu Leu Gly Tyr Ile Tyr Gly Gln Asn Cys Met
            260                 265                 270

Phe Val Val Asn Asp Trp His Ala Ser Leu Val Pro Val Leu Leu Ala
            275                 280                 285

Ala Lys Tyr Arg Pro Tyr Gly Val Tyr Lys Asp Ser Arg Ser Ile Leu
            290                 295                 300

Val Ile His Asn Leu Ala His Gln Gly Val Glu Pro Ala Ser Thr Tyr
305                 310                 315                 320

Pro Asp Leu Gly Leu Pro Pro Glu Trp Tyr Gly Ala Leu Glu Trp Val
            325                 330                 335

Phe Pro Glu Trp Ala Arg Arg His Ala Leu Asp Lys Gly Glu Ala Val
            340                 345                 350

Asn Phe Leu Lys Gly Ala Val Val Thr Ala Asp Arg Ile Val Thr Val
            355                 360                 365

Ser Lys Gly Tyr Ser Trp Glu Val Thr Thr Ala Glu Gly Gly Gln Gly
            370                 375                 380

Leu Asn Glu Leu Leu Ser Ser Arg Lys Ser Val Leu Asn Gly Ile Val
385                 390                 395                 400

Asn Gly Ile Asp Ile Asn Asp Trp Asn Pro Ala Thr Asp Lys Cys Ile
            405                 410                 415

Pro Cys His Tyr Ser Val Asp Asp Leu Ser Gly Lys Ala Lys Cys Lys
            420                 425                 430

Gly Ala Leu Gln Lys Glu Leu Gly Leu Pro Ile Arg Pro Asp Val Pro
            435                 440                 445

Leu Ile Gly Phe Ile Gly Arg Leu Asp Tyr Gln Lys Gly Ile Asp Leu
450                 455                 460

Ile Gln Leu Ile Ile Pro Asp Leu Met Arg Glu Asp Val Gln Phe Val
465                 470                 475                 480

Met Leu Gly Ser Gly Asp Pro Glu Leu Glu Asp Trp Met Arg Ser Thr
            485                 490                 495

Glu Ser Ile Phe Lys Asp Lys Phe Arg Gly Trp Val Gly Phe Ser Val
            500                 505                 510

Pro Val Ser His Arg Ile Thr Ala Gly Cys Asp Ile Leu Leu Met Pro
            515                 520                 525

Ser Arg Phe Glu Pro Cys Gly Leu Asn Gln Leu Tyr Ala Met Gln Tyr
            530                 535                 540

Gly Thr Val Pro Val Val His Ala Thr Gly Gly Leu Arg Asp Thr Val
545                 550                 555                 560

Glu Asn Phe Asn Pro Phe Gly Glu Asn Gly Glu Gln Gly Thr Gly Trp
            565                 570                 575
```

```
Ala Phe Ala Pro Leu Thr Thr Glu Asn Met Leu Trp Thr Leu Arg Thr
                580                 585                 590

Ala Ile Ser Thr Tyr Arg Glu His Lys Ser Ser Trp Glu Gly Leu Met
            595                 600                 605

Lys Arg Gly Met Ser Lys Asp Phe Thr Trp Asp His Ala Ala Glu Gln
        610                 615                 620

Tyr Glu Gln Ile Phe Gln Trp Ala Phe Ile Asp Arg Pro Tyr Val Met
625                 630                 635                 640

<210> SEQ ID NO 15
<211> LENGTH: 575
<212> TYPE: PRT
<213> ORGANISM: Arabidopsis thaliana

<400> SEQUENCE: 15

Met Asn Ser Ile Phe Pro Cys Thr Gly Asp Gln Glu Thr Val Ser Thr
1               5                   10                  15

Ser Thr Gly Glu Ile Thr His His Glu Glu Lys Lys Glu Ala Ile Asp
            20                  25                  30

Gln Ile Val Met Ala Asp Phe Gly Val Pro Gly Asn Arg Ala Val Glu
        35                  40                  45

Glu Gly Ala Ala Glu Val Gly Ile Pro Ser Gly Lys Ala Glu Val Val
    50                  55                  60

Asn Asn Leu Val Phe Val Thr Ser Glu Ala Ala Pro Tyr Ser Lys Thr
65                  70                  75                  80

Gly Gly Leu Gly Asp Val Cys Gly Ser Leu Pro Ile Ala Leu Ala Gly
                85                  90                  95

Arg Gly His Arg Val Met Val Ile Ser Pro Arg Tyr Leu Asn Gly Thr
            100                 105                 110

Ala Ala Asp Lys Asn Tyr Ala Arg Ala Lys Asp Leu Gly Ile Arg Val
        115                 120                 125

Thr Val Asn Cys Phe Gly Gly Ser Gln Glu Val Ser Phe Tyr His Glu
    130                 135                 140

His Arg Asp Gly Val Asp Trp Val Phe Val Asp His Lys Ser Tyr His
145                 150                 155                 160

Arg Pro Gly Asn Pro Tyr Gly Asp Ser Lys Gly Ala Phe Gly Asp Asn
                165                 170                 175

Gln Phe Arg Phe Thr Leu Leu Cys His Ala Ala Cys Glu Ala Pro Leu
            180                 185                 190

Val Leu Pro Leu Gly Gly Phe Thr Tyr Gly Glu Lys Ser Leu Phe Leu
        195                 200                 205

Val Asn Asp Trp His Ala Gly Leu Val Pro Ile Leu Leu Ala Ala Lys
    210                 215                 220

Tyr Arg Pro Tyr Gly Val Tyr Lys Asp Ala Arg Ser Ile Leu Ile Ile
225                 230                 235                 240

His Asn Leu Ala His Gln Gly Val Glu Pro Ala Ala Thr Tyr Thr Asn
                245                 250                 255

Leu Gly Leu Pro Ser Glu Trp Tyr Gly Ala Val Gly Trp Val Phe Pro
            260                 265                 270

Thr Trp Ala Arg Thr His Ala Leu Asp Thr Gly Glu Ala Val Asn Val
        275                 280                 285

Leu Lys Gly Ala Ile Val Thr Ser Asp Arg Ile Ile Thr Val Ser Gln
    290                 295                 300

Gly Tyr Ala Trp Glu Ile Thr Val Glu Gly Gly Tyr Gly Leu Gln
305                 310                 315                 320
```

```
Asp Leu Leu Ser Ser Arg Lys Ser Val Ile Asn Gly Ile Thr Asn Gly
                325                 330                 335

Ile Asn Val Asp Glu Trp Asn Pro Ser Thr Asp His Ile Pro Phe
            340                 345                 350

His Tyr Ser Ala Asp Asp Val Ser Glu Lys Ile Lys Cys Lys Met Ala
            355                 360                 365

Leu Gln Lys Glu Leu Gly Leu Pro Ile Arg Pro Glu Cys Pro Met Ile
370                 375                 380

Gly Phe Ile Gly Arg Leu Asp Tyr Gln Lys Gly Ile Asp Leu Ile Gln
385                 390                 395                 400

Thr Ala Gly Pro Asp Leu Met Val Asp Ile Gln Phe Val Met Leu
                405                 410                 415

Gly Ser Gly Asp Pro Lys Tyr Glu Ser Trp Met Arg Ser Met Glu Glu
            420                 425                 430

Thr Tyr Arg Asp Lys Phe Arg Gly Trp Val Gly Phe Asn Val Pro Ile
            435                 440                 445

Ser His Arg Ile Thr Ala Gly Cys Asp Ile Leu Leu Met Pro Ser Arg
    450                 455                 460

Phe Glu Pro Cys Gly Leu Asn Gln Leu Tyr Ala Met Arg Tyr Gly Thr
465                 470                 475                 480

Ile Pro Val Val His Gly Thr Gly Gly Leu Arg Asp Thr Val Glu Asn
                485                 490                 495

Phe Asn Pro Tyr Ala Glu Gly Gly Ala Gly Ala Gly Thr Gly Trp Val
            500                 505                 510

Phe Thr Pro Leu Ser Lys Asp Ser Met Val Ser Ala Leu Arg Leu Ala
            515                 520                 525

Ala Ala Thr Tyr Arg Glu Tyr Lys Gln Ser Trp Glu Gly Leu Met Arg
530                 535                 540

Arg Gly Met Thr Arg Asn Tyr Ser Trp Glu Asn Ala Ala Val Gln Tyr
545                 550                 555                 560

Glu Gln Val Phe Gln Trp Val Phe Met Asp Pro Pro Tyr Val Ser
                565                 570                 575

<210> SEQ ID NO 16
<211> LENGTH: 657
<212> TYPE: PRT
<213> ORGANISM: Theobroma cacao

<400> SEQUENCE: 16

Met Glu Ser Leu Thr Leu Gly Arg Val Leu Ser Cys Lys Leu Ser Thr
1               5                   10                  15

Asn Ile Ser Arg Lys Val Cys Ser Phe Met Pro Ser Lys Gln Leu Gly
                20                  25                  30

Phe Gly His Phe Leu Arg Arg Ser Phe Lys Asn Val Lys Leu Thr Val
            35                  40                  45

Val Lys Ser Glu Glu Ser Gly Asn Gly Gly Glu Phe Gly Gly Leu Ala
    50                  55                  60

Asp Gly Ser Asn Ser Asn Ala Val Glu Glu Glu Glu Glu Glu Glu Glu
65                  70                  75                  80

Glu Lys Lys Glu Asp Glu Lys Glu Lys Arg Gly Leu Met Leu Gly Ile
                85                  90                  95

Asp Arg Asp Asp Ser Gly Ser Val Ile Gly Leu His Leu Ile Pro Pro
            100                 105                 110

Ser Gly Asp Tyr Glu Val Ile Asp Ser His Glu Asp Val Thr Thr Asp
```

-continued

```
                115                 120                 125
Thr Lys Glu Lys Asp Gly Glu Ile Glu Glu Lys Pro Gln Thr Arg
130                 135                 140
Ile Thr Tyr Asn Ile Val Phe Val Thr Ala Glu Ala Pro Tyr Ser
145                 150                 155                 160
Lys Ser Gly Gly Leu Gly Asp Val Cys Gly Ser Leu Pro Val Ala Leu
                165                 170                 175
Ala Gly Arg Gly His Arg Val Met Val Val Ser Pro Arg Tyr Leu His
            180                 185                 190
Gly Thr Pro Ala Asp Lys Asn Ile Ala Gly Ala Leu Asp Ile Asp Arg
        195                 200                 205
Arg Ile Lys Ile Tyr Cys Phe Gly Gly Glu Gln Glu Val Ala Phe Phe
    210                 215                 220
His Glu Tyr Arg Glu Gly Val Asp Trp Val Phe Val Asp His Pro Ser
225                 230                 235                 240
Tyr His Arg Pro Gly Asn Pro Tyr Gly Asp Ser His Gly Ala Phe Gly
                245                 250                 255
Asp Asn Gln Phe Arg Phe Thr Leu Leu Cys His Ala Ala Cys Glu Ala
            260                 265                 270
Pro Leu Val Leu Pro Leu Gly Gly Tyr Thr Tyr Gly Glu Lys Cys Leu
        275                 280                 285
Phe Leu Val Asn Asp Trp His Ala Gly Leu Val Pro Val Leu Leu Ala
    290                 295                 300
Ser Lys Tyr His Pro Phe Gly Val Tyr Lys Asp Ala Arg Ser Ile Leu
305                 310                 315                 320
Ile Ile His Asn Leu Ala His Gln Gly Val Glu Pro Ala Ala Thr Phe
                325                 330                 335
Lys Asn Leu Gly Leu Pro Ser Asp Trp Tyr Gly Ala Leu Glu Trp Val
            340                 345                 350
Phe Pro Thr Trp Ala Arg Thr His Ala Leu Asp Thr Gly Glu Ala Val
        355                 360                 365
Asn Ile Leu Lys Gly Ala Ile Val Thr Ala Asp Arg Ile Leu Thr Val
    370                 375                 380
Ser Lys Gly Tyr Ala Trp Glu Ile Thr Thr Val Glu Gly Gly Tyr Gly
385                 390                 395                 400
Leu His Glu Leu Leu Ser Ser Arg Arg Ser Val Leu Asn Gly Ile Ala
                405                 410                 415
Asn Gly Ile Asp Ile Ala Glu Trp Asp Pro Ser Ser Asp Glu His Ile
            420                 425                 430
Gly Phe His Tyr Ser Ala Asp Asp Leu Ser Gly Lys Val Gln Cys Lys
        435                 440                 445
Thr Ala Leu Gln Lys Glu Leu Ala Leu Pro Ile Arg Pro Glu Cys Pro
    450                 455                 460
Leu Ile Gly Phe Ile Gly Arg Leu Asp Tyr Gln Lys Gly Ile Asp Leu
465                 470                 475                 480
Ile Arg Trp Ala Thr Pro Glu Leu Met Glu Asp Val Gln Phe Val
                485                 490                 495
Met Leu Gly Ser Gly Asp Pro Leu Tyr Glu Asp Trp Met Arg Ala Ala
            500                 505                 510
Glu Thr Thr Tyr Arg Asp Lys Phe Arg Gly Trp Val Gly Phe Asn Ile
        515                 520                 525
Pro Ile Ser His Arg Ile Thr Ala Gly Cys Asp Ile Leu Leu Met Pro
    530                 535                 540
```

```
Ser Arg Phe Glu Pro Cys Gly Leu Asn Gln Leu Tyr Ala Met Arg Tyr
545                 550                 555                 560

Ala Thr Val Pro Val His Ala Thr Gly Gly Leu Arg Asp Thr Val
            565                 570                 575

Glu Asn Phe Asn Pro Tyr Ala Gly Gly Gly Asn Gly Asp Gly Thr Gly
            580                 585                 590

Trp Thr Phe Ser Pro Leu Thr Lys Glu Ser Met Leu Glu Ala Leu Arg
            595                 600                 605

Met Ala Ile Leu Thr Tyr Arg Glu His Lys Leu Thr Trp Glu Gly Leu
610                 615                 620

Met Arg Arg Gly Leu Gln Arg Asp Cys Thr Trp Glu Ser Ala Ala Val
625                 630                 635                 640

Gln Tyr Glu Gln Val Phe Glu Trp Ala Ser Ile Asp Pro Tyr Ile
            645                 650                 655

Met

<210> SEQ ID NO 17
<211> LENGTH: 633
<212> TYPE: PRT
<213> ORGANISM: Manihot esculenta

<400> SEQUENCE: 17

Met Glu Ser Leu Arg Ile Thr Asn Gly Arg Leu Cys Pro Ser Phe Ser
1               5                   10                  15

Lys Ser Ala Asn Thr His Leu Cys Phe Ser Pro Ile Lys Gln Leu Gly
            20                  25                  30

Phe Val Tyr Leu Cys Gly Glu Arg Cys Lys Arg Ala Ser Leu Thr Leu
        35                  40                  45

Gly Arg Ser Glu Ile Gly Gly Leu Gly Ser Ser Arg Asp Glu Asp Glu
    50                  55                  60

Glu Lys Ser His Ile Leu Gly Ala Glu Arg Asp Asp Ser Gly Ser Ile
65                  70                  75                  80

Ile Gly Phe Asn Leu Ile Ser Gln Ser Gly Asp Gly Ile Glu Ser
            85                  90                  95

His Glu Asp Val Ala Thr Glu Ile Ala Glu Glu Thr Glu Asn Thr Glu
            100                 105                 110

Gly Arg Glu Glu Ala Gln Val Arg Glu Arg Leu Asn Ile Val Phe Val
            115                 120                 125

Ala Ala Glu Ala Ala Pro Tyr Ser Lys Thr Gly Gly Leu Gly Asp Val
            130                 135                 140

Cys Gly Ser Leu Pro Ile Val Leu Ala Ala Arg Gly His Arg Val Met
145                 150                 155                 160

Val Val Ser Pro Arg Tyr Leu His Phe Ile His Gln Asp Lys Val Phe
            165                 170                 175

Ala Asn Ala Leu Asp Leu Asp Arg His Ile Lys Val His Cys Phe Gly
            180                 185                 190

Gly Ala Gln Asp Val Ser Phe Phe His Glu Tyr Arg Glu Gly Val Asp
        195                 200                 205

Trp Val Phe Val Asp His Pro Ser Tyr His Arg Pro Gly Asn Pro Tyr
210                 215                 220

Gly Asp Ser Arg Gly Ala Phe Gly Asp Asn Gln Phe Arg Phe Thr Leu
225                 230                 235                 240

Leu Cys His Ala Ala Cys Glu Ala Pro Leu Val Leu Pro Leu Gly Gly
            245                 250                 255
```

-continued

Tyr Thr Tyr Gly Glu Lys Cys Leu Phe Leu Ala Asn Asp Trp His Ala
            260                 265                 270

Gly Leu Val Pro Val Leu Leu Ala Ala Lys Tyr Arg Pro His Gly Val
            275                 280                 285

Tyr Lys Asp Ala Arg Cys Leu Leu Val Ile His Asn Leu Ala His Gln
290                 295                 300

Gly Val Glu Pro Ala Val Thr Tyr Lys Asn Phe Gly Leu Pro Ser Glu
305                 310                 315                 320

Trp Tyr Gly Ala Leu Glu Trp Val Phe Pro Asn Trp Ala Arg Ala His
                325                 330                 335

Ala Leu Asp Lys Gly Glu Ala Val Asn Val Leu Lys Gly Ala Ile Val
            340                 345                 350

Thr Ala Asp Arg Ile Leu Thr Val Ser Lys Gly Tyr Ala Trp Glu Val
            355                 360                 365

Thr Thr Val Glu Gly Gly Tyr Gly Leu His Glu Leu Leu Ser Ser Arg
370                 375                 380

Arg Ser Val Leu Asp Gly Ile Thr Asn Gly Ile Asp Val Ser Glu Trp
385                 390                 395                 400

Asp Pro Ser Ala Asp Glu His Ile Ala Ala His Tyr Ser Val Asp Asp
                405                 410                 415

Leu Ser Gly Lys Val Gln Cys Lys Ile Ala Leu Gln Lys Glu Leu Gly
            420                 425                 430

Leu Pro Ile Arg Pro Met Cys Pro Leu Ile Gly Phe Ile Gly Arg Leu
            435                 440                 445

Asp Tyr Gln Lys Gly Ile Asp Leu Ile Arg Trp Ala Ile Pro Glu Leu
450                 455                 460

Met Glu Asp Asp Val Gln Phe Val Met Leu Gly Ser Gly Asp Pro Leu
465                 470                 475                 480

Tyr Glu Glu Trp Met Arg Val Thr Glu Ser Ser Tyr Arg Asp Lys Phe
                485                 490                 495

Arg Gly Trp Val Gly Phe Asn Val Pro Ile Ser His Arg Ile Thr Ala
            500                 505                 510

Gly Cys Asp Ile Leu Leu Met Pro Ser Arg Phe Glu Pro Arg Gly Leu
            515                 520                 525

Asn Gln Leu Phe Ala Met Arg Tyr Gly Thr Val Pro Val Val His Ser
530                 535                 540

Thr Gly Gly Leu Arg Asp Thr Val Gln Thr Phe Asn Pro Tyr Ala Asp
545                 550                 555                 560

Gly Gly Ile Asp Glu Gly Thr Gly Trp Thr Phe Ser Pro Leu Ser Lys
                565                 570                 575

Asp Ser Met Leu Thr Ala Ile Arg Leu Ala Val Lys Thr Tyr Arg Asp
            580                 585                 590

Tyr Lys Ser Ser Trp Glu Gly Ile Met Lys Arg Gly Met Glu Arg Asp
            595                 600                 605

Asn Thr Trp Glu Asn Ala Ala Ile His Tyr Glu Gln Val Phe Glu Trp
610                 615                 620

Ala Phe Ile Asp Ser Pro Tyr Ile Ser
625                 630

<210> SEQ ID NO 18
<211> LENGTH: 648
<212> TYPE: PRT
<213> ORGANISM: Cicer arietinum

```
<400> SEQUENCE: 18

Met Asp Ser Leu Glu Leu Pro Arg Leu Leu His His Pro Arg Ser
1               5                   10                  15

Ser Ser Pro Leu Thr Arg Pro Gln Tyr Asn Ser Arg Phe Leu Pro Gln
            20                  25                  30

Leu Pro Asn Phe Pro Ser Lys Leu Lys Asn Ala Thr Lys Tyr Ala Thr
                35                  40                  45

Leu Arg Ser Ile Ser Gly Gly Ser Asp Ala Ser Lys Asp Gly Pro
50                  55                  60

Ser Ala Phe Asp Asp Ser Ala Leu Leu Ser Arg Glu Ile Asp
65                  70                  75                  80

Asp Phe Gly Ser Leu Val Gly Phe Arg Leu Ile Pro Asp Ser Gly Thr
                85                  90                  95

Val Leu His Ala Gly Lys Thr Thr Lys Thr Gln Gly Asp Leu Arg Ser
            100                 105                 110

Asp Glu Val Glu Lys Leu Glu Val Glu Asn Val Gly Glu Lys Ala
            115                 120                 125

Lys Thr Arg Val Ser Tyr Asn Ile Val Phe Val Thr Ser Glu Ala Ala
130                 135                 140

Pro Tyr Ser Lys Thr Gly Gly Leu Ala Asp Val Cys Gly Ser Leu Pro
145                 150                 155                 160

Ile Ala Leu Ala Ala Arg Gly His Arg Val Met Val Ile Ser Pro Arg
                165                 170                 175

Tyr Ile His Gly Thr Ala Ala Asp Ser Lys Tyr Ser Gly Ala Val Asp
                180                 185                 190

Leu Asp Ser Gly Val Lys Val Phe Cys Phe Gly Gly Val Gln Glu Val
            195                 200                 205

Gly Phe Phe His Glu Tyr Arg Glu Gly Val Asp Trp Val Phe Val Asp
210                 215                 220

His Pro Ser Phe His Arg Pro Gly Asn Pro Tyr Gly Asp Lys Phe Gly
225                 230                 235                 240

Thr Phe Gly Asp Asn Gln Phe Arg Phe Thr Leu Leu Ser His Ala Ala
                245                 250                 255

Cys Glu Ala Pro Leu Val Leu Pro Leu Gly Gly Phe Thr Tyr Gly Glu
            260                 265                 270

Lys Cys Leu Phe Leu Val Asn Asp Trp His Ala Ser Leu Val Pro Val
            275                 280                 285

Leu Leu Ala Ser Lys Tyr Arg Pro His Gly Val Tyr Lys Asp Ala Arg
290                 295                 300

Ser Ile Leu Val Ile His Asn Ile Ala His Gln Gly Val Glu Pro Ala
305                 310                 315                 320

Ile Thr Tyr Ser Asn Leu Gly Leu Pro Pro Asp Trp Tyr Gly Ala Leu
                325                 330                 335

Gly Trp Val Phe Pro Thr Trp Ala Arg Thr His Ala Leu Asp Thr Gly
            340                 345                 350

Glu Ala Val Asn Phe Leu Lys Gly Ala Ile Val Thr Ala Asp Arg Ile
            355                 360                 365

Val Thr Val Ser Lys Gly Tyr Ser Trp Glu Ile Thr Asn Glu Gly
370                 375                 380

Gly Phe Gly Leu His Glu Ile Leu Thr Glu Arg Arg Ser Ile Leu Ser
385                 390                 395                 400

Gly Ile Thr Asn Gly Ile Asp Val Thr Glu Trp Asp Pro Leu Ser Asp
                405                 410                 415
```

```
Glu His Ile Ala Cys Asn Tyr Ser Ala Asp Asp Leu Ser Gly Lys Val
            420                 425                 430

Lys Cys Lys Ile Ala Leu Gln Lys Glu Leu Gly Leu Pro Val Arg Pro
            435                 440                 445

Asp Cys Pro Leu Ile Gly Phe Val Gly Arg Leu Asp Tyr Gln Lys Gly
            450                 455                 460

Ile Asp Leu Ile Arg Gln Ala Ile Pro Glu Leu Met Gln Asp Asp Val
465                 470                 475                 480

Gln Phe Val Met Leu Gly Ser Gly Asn Pro Ile Tyr Glu Asp Trp Met
                485                 490                 495

Arg Ala Thr Glu Leu Ala Tyr Lys Asp Gln Phe Arg Gly Trp Val Gly
            500                 505                 510

Phe Asn Val Pro Val Ser His Arg Ile Thr Ala Gly Cys Asp Ile Leu
            515                 520                 525

Leu Met Pro Ser Thr Phe Glu Pro Cys Gly Leu Asn Gln Leu Tyr Ala
            530                 535                 540

Met Arg Tyr Gly Thr Ile Pro Val Val His Glu Thr Gly Gly Leu Arg
545                 550                 555                 560

Asp Thr Val Gln Thr Phe Asn Pro Tyr Ala Glu Gly Ser Asn Ala Glu
                565                 570                 575

Gly Ser Asn Ala Glu Gly Thr Gly Trp Thr Phe Ser Pro Leu Thr Lys
            580                 585                 590

Glu Ser Met Leu Val Ala Leu Arg Tyr Ala Ile Gln Thr Phe Asn Glu
            595                 600                 605

His Lys Pro Ser Trp Glu Gly Leu Met Lys Arg Gly Met Thr Arg Asp
            610                 615                 620

Tyr Thr Trp Val Asn Ala Ala Thr Gln Tyr Glu Gln Ile Ile Glu Trp
625                 630                 635                 640

Ala Phe Met Asp Pro Pro Tyr Cys
                645

<210> SEQ ID NO 19
<211> LENGTH: 645
<212> TYPE: PRT
<213> ORGANISM: Prunus persica

<400> SEQUENCE: 19

Met Glu Ser Leu Lys Phe Thr Ser Leu Ile Pro Cys Lys Ser Ser Val
1               5                   10                  15

Asn Leu Ile Pro Thr Thr Lys Phe Val Asn His Glu Val Ile Gly Gln
            20                  25                  30

Val Gly Phe Val Pro Leu Trp Lys Arg Arg Ser Thr Arg Pro Ala Phe
        35                  40                  45

Arg Leu Arg Ala Gln Val Ser Gly Ser Gly Ala Gln Asp Gly
    50                  55                  60

Ala Ser Ala Leu Glu Asp Gln Arg Glu Glu Lys Gly Val Leu Leu Gly
65                  70                  75                  80

Ala Glu Thr Asp Ser Ser Gly Ser Val Ile Gly Phe Asn Leu Ile Pro
                85                  90                  95

Pro Asn Gly Glu Leu Lys Val Pro Asp Ser Pro Glu Asp Ala Thr
            100                 105                 110

Ser Asp Arg Leu Asp Glu Thr Glu Asp Ile Asp Gly Lys Glu Lys Ser
        115                 120                 125

Lys Ala Lys Val Thr Arg Asn Ile Val Phe Val Thr Ala Glu Ala Ala
```

```
            130                 135                 140
Pro Tyr Ser Lys Thr Gly Gly Leu Gly Asp Val Cys Gly Ser Leu Pro
145                 150                 155                 160

Thr Val Leu Ala Ala Arg Gly His Arg Val Met Val Val Ser Pro Arg
                    165                 170                 175

Tyr Gln Asn Gly Thr Ala Ala Asp Gln Lys Phe Ser Gly Ala Leu
                180                 185                 190

Asp Leu Asp Thr Arg Ile Lys Ile Tyr Cys Phe Gly Asp Gln Glu
                195                 200                 205

Val Gly Phe Phe His Glu Tyr Arg Glu Gly Val Asp Trp Val Phe Val
210                 215                 220

Asp His Pro Ser Phe His Arg Pro Gly Asn Pro Tyr Gly Asp Ser Phe
225                 230                 235                 240

Gly Ala Phe Gly Asp Asn Gln Phe Arg Phe Thr Leu Leu Cys His Ala
                245                 250                 255

Ala Cys Glu Ala Pro Leu Val Leu Pro Leu Gly Gly Tyr Thr Tyr Gly
                260                 265                 270

Glu Lys Cys Leu Phe Met Val Asn Asp Trp His Ala Gly Leu Val Pro
                275                 280                 285

Leu Leu Leu Ala Ala Lys Tyr Arg Pro Tyr Gly Val Tyr Lys Asp Ala
290                 295                 300

Arg Ser Val Val Ile His Asn Leu Ala His Gln Gly Val Glu Pro
305                 310                 315                 320

Ala Val Thr Phe Lys Asn Leu Gly Ile Pro Pro Glu Trp Tyr Gly Ala
                325                 330                 335

Leu Glu Trp Val Phe Pro Thr Trp Ala Arg Thr His Ala Leu Asp Thr
                340                 345                 350

Gly Glu Ala Val Asn Ile Leu Lys Gly Ala Ile Val Thr Ser Asp Arg
                355                 360                 365

Ile Leu Thr Val Ser Glu Gly Tyr Ser Trp Glu Ile Thr Thr Val Glu
                370                 375                 380

Gly Gly Tyr Gly Leu Asn Glu Leu Leu Ser Ser Arg Lys Ser Ile Ile
385                 390                 395                 400

Thr Gly Ile Thr Asn Gly Val Asp Val Val Glu Trp Asp Pro Ser Ser
                405                 410                 415

Asp Val His Ile Ala Ser His Tyr Ser Ala Asp Asp Leu Ser Gly Lys
                420                 425                 430

Val Gln Cys Lys Leu Ala Leu Gln Lys Glu Leu Gly Leu Pro Ile Arg
                435                 440                 445

Pro Asp Cys Pro Leu Ile Gly Phe Ile Gly Arg Leu Asp Tyr Gln Lys
450                 455                 460

Gly Ile Asp Leu Ile Gln Ser Gly Met Pro Gln Leu Met Glu Asp Asp
465                 470                 475                 480

Val Gln Phe Val Met Leu Gly Ser Gly Asp Pro Leu Cys Glu Asp Trp
                485                 490                 495

Met Arg Ala Ala Glu Ala Thr Tyr Lys Asp Lys Phe Arg Gly Trp Val
                500                 505                 510

Gly Phe Asn Val Pro Val Ser His Arg Ile Thr Ala Gly Cys Asp Ile
                515                 520                 525

Leu Leu Met Pro Ser Arg Phe Glu Pro Cys Gly Leu Asn Gln Leu Tyr
530                 535                 540

Ala Met Arg Tyr Gly Thr Val Pro Val Val His Ser Thr Gly Gly Leu
545                 550                 555                 560
```

Arg Asp Thr Val Leu Asn Phe Asn Pro Tyr Ala Gln Gly Gly Gln Gly
            565                 570                 575

Asp Gly Thr Gly Trp Thr Phe Ser Pro Leu Thr Lys Glu Ser Met Leu
            580                 585                 590

Ala Ala Leu Arg Leu Ala Cys Arg Thr Phe Thr Glu Tyr Lys Pro Ser
            595                 600                 605

Trp Glu Gly Leu Met Lys Arg Gly Met Glu Arg Asp Phe Thr Trp Glu
            610                 615                 620

Ser Ala Ala Val Lys Tyr Glu Gln Val Phe Glu Trp Ala Phe Ile Asp
625                 630                 635                 640

Pro Pro Tyr Ile Cys
            645

<210> SEQ ID NO 20
<211> LENGTH: 641
<212> TYPE: PRT
<213> ORGANISM: Solanum lycopersicum

<400> SEQUENCE: 20

Met Gly Ser Leu Arg Thr Pro Thr Asn Leu Ser Asn Lys Ser Cys Leu
1               5                   10                  15

Cys Val Ser Gly Arg Val Val Lys Gly Leu Arg Val Glu Arg Gln Val
                20                  25                  30

Gly Leu Gly Phe Ser Trp Leu Leu Lys Gly Arg Arg Asn Arg Lys Val
            35                  40                  45

Gln Ser Leu Cys Val Thr Ser Ser Val Ser Asp Gly Ser Ser Ile Ala
        50                  55                  60

Glu Asn Lys Lys Val Ser Glu Gly Leu Leu Leu Gly Pro Glu Arg Asp
65                  70                  75                  80

Gly Ser Gly Ser Val Val Gly Phe Gln Leu Ile Pro His Ser Val Ala
                85                  90                  95

Gly Asp Ala Thr Met Val Glu Ser His Asp Ile Val Ala Asn Asp Arg
            100                 105                 110

Asp Asp Leu Arg Glu Asp Ala Glu Glu Met Glu Glu Thr Pro Ile Lys
        115                 120                 125

Leu Thr Phe Asn Ile Ile Phe Val Thr Ala Glu Ala Ala Pro Tyr Ser
130                 135                 140

Lys Thr Gly Gly Leu Gly Asp Val Cys Gly Ser Leu Pro Met Ala Leu
145                 150                 155                 160

Ala Ala Arg Gly His Arg Val Met Val Val Ser Pro Arg Tyr Leu Asn
                165                 170                 175

Gly Gly Pro Ser Asp Glu Lys Tyr Ala Asn Ala Val Asp Leu Asp Val
            180                 185                 190

Arg Ala Thr Val His Cys Phe Gly Asp Ala Gln Glu Val Ala Phe Tyr
        195                 200                 205

His Glu Tyr Arg Ala Gly Val Asp Trp Val Phe Val Asp His Ser Ser
    210                 215                 220

Tyr Arg Arg Pro Gly Thr Pro Tyr Gly Asp Ile Tyr Gly Ala Phe Gly
225                 230                 235                 240

Asp Asn Gln Phe Arg Phe Thr Leu Leu Ser His Ala Ala Cys Glu Ala
                245                 250                 255

Pro Leu Val Leu Pro Leu Gly Gly Phe Thr Tyr Gly Glu Lys Cys Leu
            260                 265                 270

Phe Leu Ala Asn Asp Trp His Ala Ser Leu Val Pro Leu Leu Leu Ala

```
                275                 280                 285
Ala Lys Tyr Arg Pro Tyr Gly Val Tyr Lys Asp Ala Arg Ser Ile Val
290                 295                 300
Ala Ile His Asn Ile Ala His Gln Gly Val Glu Pro Ala Ala Thr Tyr
305                 310                 315                 320
Asn Asn Leu Gly Leu Pro Pro Gln Trp Tyr Gly Ala Leu Glu Trp Ile
                325                 330                 335
Phe Pro Thr Trp Ala Arg Ala His Ala Leu Asp Thr Gly Glu Thr Val
            340                 345                 350
Asn Val Leu Lys Gly Ala Ile Ser Val Ala Asp Arg Ile Leu Thr Val
            355                 360                 365
Ser Gln Gly Tyr Ser Trp Glu Ile Thr Thr Pro Glu Gly Gly Tyr Gly
370                 375                 380
Leu His Glu Leu Leu Ser Ser Arg Gln Ser Val Leu Asn Gly Ile Thr
385                 390                 395                 400
Asn Gly Ile Asp Val Asn Asp Trp Asn Pro Ser Thr Asp Glu His Ile
                405                 410                 415
Ala Ser His Tyr Ser Ile Asn Asp Leu Ser Gly Lys Ala Gln Cys Lys
            420                 425                 430
Thr Asp Leu Gln Lys Glu Leu Gly Leu Pro Ile Arg Pro Asp Cys Pro
            435                 440                 445
Leu Ile Gly Phe Ile Gly Arg Leu Asp Tyr Gln Lys Gly Val Asp Ile
450                 455                 460
Ile Leu Ser Ala Ile Pro Glu Leu Leu Gln Lys Asp Val Gln Phe Val
465                 470                 475                 480
Met Leu Gly Ser Gly Glu Lys Gln Tyr Glu Asp Trp Met Arg His Thr
                485                 490                 495
Glu Asn Leu Phe Lys Asp Lys Phe Arg Ala Trp Val Gly Phe Asn Val
            500                 505                 510
Pro Val Ser His Arg Ile Thr Ala Gly Cys Asp Ile Leu Leu Met Pro
            515                 520                 525
Ser Arg Phe Glu Pro Cys Gly Leu Asn Gln Leu Tyr Ala Met Arg Tyr
530                 535                 540
Gly Thr Ile Pro Val Val His Ser Thr Gly Gly Leu Arg Asp Thr Val
545                 550                 555                 560
Lys Asp Phe Asn Pro Tyr Ala Gln Glu Gly Lys Gly Glu Gly Thr Gly
                565                 570                 575
Trp Thr Phe Ser Pro Leu Thr Ser Glu Lys Leu Leu Asp Thr Leu Lys
            580                 585                 590
Leu Ala Ile Gly Thr Tyr Thr Glu His Lys Ser Ser Trp Glu Gly Leu
            595                 600                 605
Met Lys Arg Gly Met Gly Arg Asp Tyr Ser Trp Glu Asn Ala Ala Ile
            610                 615                 620
Gln Tyr Glu Gln Val Phe Thr Trp Ala Phe Met Asp Pro Pro Tyr Val
625                 630                 635                 640
Arg
```

<210> SEQ ID NO 21
<211> LENGTH: 2623
<212> TYPE: DNA
<213> ORGANISM: Oryza sativa

<400> SEQUENCE: 21
gtgccccacc gcctcagcgc ctctccctcg cttaaaacca aacccacaca cccacctctt    60

```
ctctctctct catcgtctcc gcgactcagc ccactcctct ctctccacca ccaccaccac    120
caccaccacc gcccgccaag cgcggcccgc ccgacacagc agcagcagga tcggcggaga    180
ggagggggga tcatggcgac ggcggcgggg atggggatcg gggcggcgtg cctggtggcg    240
ccgcaggtga ggccggggag gaggttgcgg ctccagcggg tgcggaggcg gtgcgtggcg    300
gagctgagca gggacggtgg gtcggcgcag cgcccgctgg caccggcgcc gctggtgaag    360
cagccggtcc tgccgacctt cctcgtgccg acgtcgacgc cacccgcgcc cacgcagtcg    420
ccggcgccgg cgccgacccc gccgccgttg ccggactccg gcgtgggggga gatcgagccc    480 gatctagaag gtctcacaga agattccatc gacaaaacaa tttttgtggc tagtgagcag    540
gagtctgaga tcatggatgt gaaggagcaa gctcaagcta aagtaacacg cagcgttgtc    600
tttgtaaccg gtgaagcttc tccttatgca aagtcaggtg gactaggaga tgttgtggt     660 tcactgccaa ttgctcttgc tcttcgtggt catcgtgtga tggttgtaat gccgagatac    720
atgaacgggg ccttgaacaa aaattttgca aacgcatttt acactgagaa gcacattaag    780
attccatgct tggcggaga catgaagtt acttttttc acgagtatag ggattctgtt       840
gattgggtgt tgttgatca tccctcatat catagacctg gaaatttgta tggagataat     900
tttggtgctt ttggcgataa tcagttcaga tacacactcc tgtgctatgc ggcgtgtgaa    960
gccccattaa ttcttgaact gggaggatat atctatggac agaaatgcat gtttgttgtg    1020
aatgattggc atgccagtct tgtgccagtc cttcttgctg caaaatatag accatatggt    1080
gtttacaggg atgcccgcag tgttcttgtc atacataatc tagcacatca gggtgtggag    1140
cctgccagta catatcctga cctgggattg ccacctgaat ggtatggagc attagaatgg    1200
gtgtttccag agtgggcaag gcggcatgcc cttgacaagg gtgaggcagt caatttttta    1260
aaaggcgcag ttgtgacagc agatcgaatt gtgactgtca gccagggggta ttcatgggag   1320 gtcacaactg ctgaaggtgg gcaaggcctc aatgagctct taagctcccg gaagagtgta    1380
ttgaatggaa ttgtaaatgg aattgacatt aatgattgga acccatccac agacaagttt    1440
ctcccttatc attattctgt tgatgacctg tccggaaagg ccaagtgtaa agctgaattg    1500
cagaaggagc tgggtttacc tataaggccc gatgtgcctc tgattggctt tattggaaga    1560
ttggactatc aaaaaggcat tgatctaatt aaacttgcca ttccagatct catgcgggac    1620
aatattcaat tcgtcatgct tggatctggt gacccaggtt ttgaaggatg gatgagatcc    1680
acagaatcag ggtacaggga taaatttcgt ggatgggttg gatttagtgt tccagtttcc    1740
caccgaataa ctgcaggttg cgatatattg ttgatgccat ccagattcga accttgtggc    1800
ctcaatcagc tatatgctat gcaatatggt acagtgcctg ttgttcatgg aactggaggc    1860
ctcagagata cagtggagaa ttttaacccg tttgctgaga aaggagagca gggtacaggg    1920
tgggcattct cgccactaac cattgaaaaa atgctgtggg cattgcggat ggcaatttcg    1980
acatacaggg aacacaagtc ctcttgggag ggtctaatga agcgaggcat gtcaagcgac    2040
tttacatggg accatgccgc ctcacagtat gaacagatct tcgaatgggc cttcatggat    2100
caaccatatg tcatgtaaat ggatttgaag gaagcagcga atttctccga ggaccctcaa    2160
tcttcctgtc tttcatgagc ggaatgaaaa ctttgtacac tacatggaaa gggaaccagt    2220
tatgcaaagt tgcaaacgat cactcaaggt taccccttgta ggcctgctac ttggccaata    2280
tggttccagt gaccatatgc agagtcaggt tcagatgaat ggcacttgtg agtagtgaag    2340
aataagatga ggatgcttga agcggtttca catgtggctg ataccacgca agcaacctct    2400
```

```
caatgcatcg aaatgtgagt cttggaatca ataggattta gctcccatca attacagttg    2460
tacccttttt tgcttaatac tttgtcgcct gtgctgttct tatatttgtg tgaagataaa    2520
ttttagtcca ttaggtaact gtattgttga gtcttaaggt gaagactaaa tagtgtttgg    2580
aagctgtagc tactgcgatg tcaagtgtca aaagagatct tgg                      2623

<210> SEQ ID NO 22
<211> LENGTH: 463
<212> TYPE: DNA
<213> ORGANISM: Artificial Sequence
<220> FEATURE:
<223> OTHER INFORMATION: Synthesized plasmid from 5' end of rice SSS
      gene with leader sequence

<400> SEQUENCE: 22
tcactcgagg gatccgttta acatcatgg cgacggcggc ggggatgggg atcggggcgg      60
cgtgcctggt ggcgccgcag gtgaggccgg ggaggaggtt gcggctccag cgggtgcgga    120
ggcggtgcgt ggcggagctg agcagggacg gtgggtcggc gcagcgcccg ctggcaccgg    180
cgccgctggt gaagcagccg gtcctgccga ccttcctcgt gccgacgtcg acgccacccg    240
cgcccacgca gtcgccggcg ccggcgccga ccccgccgcc gttgccggac tccggcgtgg    300
gggagatcga gcccgatcta gaaggtctca cagaagattc catcgacaaa acaattttg     360 tggctagtga gcaggagtct gagatcatgg atgtgaagga gcaagctcaa gctaaagtaa    420
cacgcagcgt tgtctttgta accggtgaag cttctcctta tgc                      463

<210> SEQ ID NO 23
<211> LENGTH: 1674
<212> TYPE: DNA
<213> ORGANISM: Artificial Sequence
<220> FEATURE:
<223> OTHER INFORMATION: PCR product of 3' end of the SSS gene from,
      Kitaake rice cDNA

<400> SEQUENCE: 23
agcccgatct agaaggtctc acagaagatt ccatcgacaa acaattttt gtggctagtg       60 agcaggagtc tgagatcatg gatgtgaagg agcaagctca agctaaagta acacgcagcg    120
ttgtctttgt aaccggtgaa gcttctcctt atgcaaagtc aggtggacta ggagatgttt    180
gtggttcact gccaattgct cttgctcttc gtggtcatcg tgtgatggtt gtaatgccga    240
gatacatgaa cggggccttg aacaaaaatt ttgcaaacgc attttacact gagaagcaca    300
ttaagattcc atgctttggc ggagaacatg aagttacttt ttttcacgag tatagggatt    360
ctgttgattg ggtgtttgtt gatcatccct catatcatag acctggaaat ttgtatggag    420
ataattttgg tgcttttggc gataatcagt tcagatacac actcctgtgc tatgcggcgt    480
gtgaagcccc attaattctt gaactgggag atatatcta tggacagaaa tgcatgtttg    540
ttgtgaatga ttggcatgcc agtcttgtgc cagtccttct tgctgcaaaa tatagaccat    600
atggtgttta cagggatgcc cgcagtgttc ttgtcataca taatctagca catcagggtg    660
tggagcctgc cagtacatat cctgacctgg gattgccacc tgaatggtat ggagcattag    720
aatgggtgtt tccagagtgg gcaaggcggc atgcccttga caaggtgag gcagtcaatt     780 ttttaaaagg cgcagttgtg acagcagatc gaattgtgac tgtcagccag gggtattcat    840
gggaggtcac aactgctgaa ggtgggcaag gcctcaatga gctcttaagc tcccggaaga    900
gtgtattgaa tggaattgta aatggaattg acattaatga ttggaaccca tccacagaca    960
agtttctccc ttatcattat tctgttgatg acctgtccgg aaaggccaag tgtaaagctg   1020
```

```
aattgcagaa ggagctgggt ttacctataa ggcccgatgt gcctctgatt ggctttattg    1080
gaagattgga ctatcaaaaa ggcattgatc taattaaact tgccattcca gatctcatgc    1140
gggacaatat tcaattcgtc atgcttggat ctggtgaccc aggttttgaa ggatggatga    1200
gatccacaga atcagggtac agggataaat ttcgtggatg ggttggattt agtgttccag    1260
tttcccaccg aataactgca ggttgcgata tattgttgat gccatccaga ttcgaacctt    1320
gtggcctcaa tcagctatat gctatgcaat atggtacagt gcctgttgtt catgaactg     1380 gaggcctcag agatacagtg gagaatttta acccgtttgc tgagaaagga gagcagggta    1440
cagggtgggc attctcgcca ctaaccattg aaaaaatgct gtgggcattg cggatggcaa    1500
tttcgacata cagggaacac aagtcctctt gggagggtct aatgaagcga ggcatgtcaa    1560
gcgactttac atgggaccat gccgcctcac agtatgaaca gatcttcgaa tgggccttca    1620
tggatcaacc atatgtcatg taaatggatt tgaaggaagc agcgaatttc tccg          1674
```

<210> SEQ ID NO 24
<211> LENGTH: 26
<212> TYPE: DNA
<213> ORGANISM: Artificial Sequence
<220> FEATURE:
<223> OTHER INFORMATION: Synthetic primer

<400> SEQUENCE: 24
agcccgatct agaaggtctc acagaa                                          26

<210> SEQ ID NO 25
<211> LENGTH: 24
<212> TYPE: DNA
<213> ORGANISM: Artificial Sequence
<220> FEATURE:
<223> OTHER INFORMATION: Synthetic primer

<400> SEQUENCE: 25
cggagaaatt cgctgcttcc ttca                                            24

<210> SEQ ID NO 26
<211> LENGTH: 124
<212> TYPE: DNA
<213> ORGANISM: Artificial Sequence
<220> FEATURE:
<223> OTHER INFORMATION: Multiple cloning site of pCR-Blunt.
<220> FEATURE:
<221> NAME/KEY: misc_feature
<222> LOCATION: (61)..(62)
<223> OTHER INFORMATION: Integration site of blunt PCR product between
      residues 61 and 62. Sequence was inserted in reverse orientation.

<400> SEQUENCE: 26
atcaagcttg gtaccgagct cggatccact agtaacggcc gccagtgtgc tggaattcag    60
gcctgaattc tgcagatatc catcacactg gcggccgctc gagcatgcat ctagagggcc    120
caat                                                                  124

<210> SEQ ID NO 27
<211> LENGTH: 2020
<212> TYPE: DNA
<213> ORGANISM: Artificial Sequence
<220> FEATURE:
<223> OTHER INFORMATION: Synthesized sequence in pCRBLUNT-SSS from XhoI
      site to the BamHI site of pCRBLUNT

<400> SEQUENCE: 27

```
ctcgagggat ccgtttaaac atcatggcga cggcggcggg gatggggatc ggggcggcgt    60
gcctggtggc gccgcaggtg aggccgggga ggaggttgcg gctccagcgg gtgcggaggc   120
ggtgcgtggc ggagctgagc agggacggtg ggtcggcgca gcgcccgctg gcaccggcgc   180
cgctggtgaa gcagccggtc ctgccgacct tcctcgtgcc gacgtcgacg ccacccgcgc   240
ccacgcagtc gccggcgccg gcgccgaccc cgccgccgtt gccggactcc ggcgtggggg   300
agatcgagcc cgatctagaa ggtctcacag aagattccat cgacaaaaca attttttgtgg  360
ctagtgagca ggagtctgag atcatggatg tgaaggagca agctcaagct aaagtaacac   420
gcagcgttgt ctttgtaacc ggtgaagctt ctccttatgc aaagtcaggt ggactaggag   480
atgtttgtgg ttcactgcca attgctcttg ctcttcgtgg tcatcgtgtg atggttgtaa   540
tgccagata catgaacggg gccttgaaca aaaattttgc aaacgcattt tacactgaga    600
agcacattaa gattccatgc tttggcggag aacatgaagt tacttttttt cacgagtata   660
gggattctgt tgattgggtg tttgttgatc atccctcata tcatagacct ggaaatttgt   720
atggagataa ttttggtgct tttggcgata tcagttcag atacacactc ctgtgctatg    780
cggcgtgtga agccccatta attcttgaac tgggaggata tatctatgga cagaaatgca   840
tgtttgttgt gaatgattgg catgccagtc ttgtgccagt ccttcttgct gcaaaatata   900
gaccatatgg tgtttacagg gatgcccgca gtgttcttgt catacataat ctagcacatc   960
agggtgtgga gcctgccagt acatatcctg acctgggatt gccacctgaa tggtatggag  1020
cattagaatg ggtgtttcca gagtgggcaa ggcggcatgc ccttgacaag ggtgaggcag  1080
tcaattttt aaaaggcgca gttgtgacag cagatcgaat tgtgactgtc agccaggggt   1140
attcatggga ggtcacaact gctgaaggtg ggcaaggcct caatgagctc ttaagctccc  1200
ggaagagtgt attgaatgga attgtaaatg gaattgacat taatgattgg aacccatcca  1260
cagacaagtt tctcccttat cattattctg ttgatgacct gtccggaaag gccaagtgta  1320
aagctgaatt gcagaaggag ctgggtttac ctataaggcc cgatgtgcct ctgattggct  1380
ttattggaag attggactat caaaaaggca ttgatctaat taaacttgcc attccagatc  1440
tcatgcggga caatattcaa ttcgtcatgc ttggatctgg tgacccaggt tttgaaggat  1500
ggatgagatc cacagaatca gggtacaggg ataaatttcg tggatgggtt ggatttagtg  1560
ttccagtttc ccaccgaata actgcaggtt gcgatatatt gttgatgcca tccagattcg  1620
aaccttgtgg cctcaatcag ctatatgcta tgcaatatgg tacagtgcct gttgttcatg  1680
gaactggagg cctcagagat acagtggaga attttaaccc gtttgctgag aaaggagagc  1740
agggtacagg gtgggcattc tcgccactaa ccattgaaaa aatgctgtgg gcattgcgga  1800
tggcaatttc gacatacagg gaacacaagt cctcttggga gggtctaatg aagcgaggca  1860
tgtcaagcga ctttacatgg gaccatgccg cctcacagta tgaacagatc ttcgaatggg  1920
ccttcatgga tcaaccatat gtcatgtaaa tggatttgaa ggaagcagcg aatttctccg  1980
cctgaattcc agcacactgg cggccgttac tagtggatcc                         2020
```

<210> SEQ ID NO 28
<211> LENGTH: 22
<212> TYPE: DNA
<213> ORGANISM: Artificial Sequence
<220> FEATURE:
<223> OTHER INFORMATION: Synthetic primer

<400> SEQUENCE: 28

```
gtgcctctga ttggctttat tg                                             22
```

<210> SEQ ID NO 29
<211> LENGTH: 24
<212> TYPE: DNA
<213> ORGANISM: Artificial Sequence
<220> FEATURE:
<223> OTHER INFORMATION: Synthetic primer

<400> SEQUENCE: 29
aggtaaaccc agctccttct gcaa                                              24

<210> SEQ ID NO 30
<211> LENGTH: 24
<212> TYPE: DNA
<213> ORGANISM: Artificial Sequence
<220> FEATURE:
<223> OTHER INFORMATION: Synthetic primer

<400> SEQUENCE: 30
tgccaattgc tcttgctctt cgtg                                              24

<210> SEQ ID NO 31
<211> LENGTH: 23
<212> TYPE: DNA
<213> ORGANISM: Artificial Sequence
<220> FEATURE:
<223> OTHER INFORMATION: Synthetic primer

<400> SEQUENCE: 31
tcagcagttg tgacctccca tga                                               23

<210> SEQ ID NO 32
<211> LENGTH: 23
<212> TYPE: DNA
<213> ORGANISM: Artificial Sequence
<220> FEATURE:
<223> OTHER INFORMATION: Synthetic primer

<400> SEQUENCE: 32
gccaattgct cttgctcttc gtg                                               23

<210> SEQ ID NO 33
<211> LENGTH: 24
<212> TYPE: DNA
<213> ORGANISM: Artificial Sequence
<220> FEATURE:
<223> OTHER INFORMATION: Synthetic primer

<400> SEQUENCE: 33
ttcagcagtt gtgacctccc atga                                              24

<210> SEQ ID NO 34
<211> LENGTH: 23
<212> TYPE: DNA
<213> ORGANISM: Artificial Sequence
<220> FEATURE:
<223> OTHER INFORMATION: Synthetic primer

<400> SEQUENCE: 34
atctgtgcct tgaccgtatc agg                                               23

<210> SEQ ID NO 35
<211> LENGTH: 24
<212> TYPE: DNA
<213> ORGANISM: Artificial Sequence
<220> FEATURE:

-continued

<223> OTHER INFORMATION: Synthetic primer

<400> SEQUENCE: 35
gacatcaaca ttcagagcac catc                24

<210> SEQ ID NO 36
<211> LENGTH: 647
<212> TYPE: PRT
<213> ORGANISM: Triticum aestivum

<400> SEQUENCE: 36

Met Ala Ala Thr Gly Val Gly Ala Gly Cys Leu Ala Pro Ser Val Arg
1               5                   10                  15

Leu Arg Ala Asp Pro Ala Thr Ala Ala Arg Ala Ser Ala Cys Val Val
            20                  25                  30

Arg Ala Arg Leu Arg Arg Leu Ala Arg Gly Arg Tyr Val Ala Glu Leu
        35                  40                  45

Ser Arg Glu Gly Pro Ala Ala Arg Pro Ala Gln Gln Gln Gln Leu Ala
    50                  55                  60

Pro Pro Leu Val Pro Gly Phe Leu Ala Pro Pro Pro Ala Pro Ala
65                  70                  75                  80

Gln Ser Pro Ala Pro Thr Gln Pro Pro Leu Pro Asp Ala Gly Val Gly
                85                  90                  95

Glu Leu Ala Pro Asp Leu Leu Leu Glu Gly Ile Ala Glu Asp Ser Ile
            100                 105                 110

Asp Ser Ile Ile Val Ala Ala Ser Glu Gln Asp Ser Glu Ile Met Asp
        115                 120                 125

Ala Asn Glu Gln Pro Gln Ala Lys Val Thr Arg Ser Ile Val Phe Val
    130                 135                 140

Thr Gly Glu Ala Ala Pro Tyr Ala Lys Ser Gly Gly Leu Gly Asp Val
145                 150                 155                 160

Cys Gly Ser Leu Pro Ile Ala Leu Ala Ala Arg Gly His Arg Val Met
                165                 170                 175

Val Val Met Pro Arg Tyr Leu Asn Gly Ser Ser Asp Lys Asn Tyr Ala
            180                 185                 190

Lys Ala Leu Tyr Thr Gly Lys His Ile Lys Ile Pro Cys Phe Gly Gly
        195                 200                 205

Ser His Glu Val Thr Phe Phe His Glu Tyr Arg Asp Asn Val Asp Trp
    210                 215                 220

Val Phe Val Asp His Pro Ser Tyr His Arg Pro Gly Ser Leu Tyr Gly
225                 230                 235                 240

Asp Asn Phe Gly Ala Phe Gly Asp Asn Gln Phe Arg Tyr Thr Leu Leu
                245                 250                 255

Cys Tyr Ala Ala Cys Glu Ala Pro Leu Ile Leu Glu Leu Gly Gly Tyr
            260                 265                 270

Ile Tyr Gly Gln Asn Cys Met Phe Val Val Asn Asp Trp His Ala Ser
        275                 280                 285

Leu Val Pro Val Leu Leu Ala Ala Lys Tyr Arg Pro Tyr Gly Val Tyr
    290                 295                 300

Arg Asp Ser Arg Ser Thr Leu Val Ile His Asn Leu Ala His Gln Gly
305                 310                 315                 320

Leu Glu Pro Ala Ser Thr Tyr Pro Asp Leu Gly Leu Pro Pro Glu Trp
                325                 330                 335

Tyr Gly Ala Leu Glu Trp Val Phe Pro Glu Trp Ala Arg Arg His Ala
            340                 345                 350

-continued

Leu Asp Lys Gly Glu Ala Val Asn Phe Leu Lys Gly Ala Val Val Thr
          355                 360                 365

Ala Asp Arg Ile Val Thr Val Ser Gln Gly Tyr Ser Trp Glu Val Thr
     370                 375                 380

Thr Ala Glu Gly Gly Gln Gly Leu Asn Glu Leu Leu Ser Ser Arg Lys
385                 390                 395                 400

Ser Val Leu Asn Gly Ile Val Asn Gly Ile Asp Ile Asn Asp Trp Asn
              405                 410                 415

Pro Thr Thr Asp Lys Cys Leu Pro His His Tyr Ser Val Asp Asp Leu
              420                 425                 430

Ser Gly Lys Ala Lys Cys Lys Ala Glu Leu Gln Lys Glu Leu Gly Leu
          435                 440                 445

Pro Val Arg Glu Asp Val Pro Leu Ile Gly Phe Ile Gly Arg Leu Asp
     450                 455                 460

Tyr Gln Lys Gly Ile Asp Leu Ile Lys Met Ala Ile Pro Glu Leu Met
465                 470                 475                 480

Arg Glu Asp Val Gln Phe Val Met Leu Gly Ser Gly Asp Pro Ile Phe
              485                 490                 495

Glu Gly Trp Met Arg Ser Thr Glu Ser Ser Tyr Lys Asp Lys Phe Arg
          500                 505                 510

Gly Trp Val Gly Phe Ser Val Pro Val Ser His Arg Ile Thr Ala Gly
     515                 520                 525

Cys Asp Ile Leu Leu Met Pro Ser Arg Phe Glu Pro Cys Gly Leu Asn
530                 535                 540

Gln Leu Tyr Ala Met Gln Tyr Gly Thr Val Pro Val Val His Gly Thr
545                 550                 555                 560

Gly Gly Leu Arg Asp Thr Val Glu Thr Phe Asn Pro Phe Gly Ala Lys
              565                 570                 575

Gly Glu Glu Gly Thr Gly Trp Ala Phe Ser Pro Leu Thr Val Asp Lys
          580                 585                 590

Met Leu Trp Ala Leu Arg Thr Ala Met Ser Thr Phe Arg Glu His Lys
     595                 600                 605

Pro Ser Trp Glu Gly Leu Met Lys Arg Gly Met Thr Lys Asp His Thr
     610                 615                 620

Trp Asp His Ala Ala Glu Gln Tyr Glu Gln Ile Phe Glu Trp Ala Phe
625                 630                 635                 640

Val Asp Gln Pro Tyr Val Met
              645

<210> SEQ ID NO 37
<211> LENGTH: 647
<212> TYPE: PRT
<213> ORGANISM: Ae. tauschii

<400> SEQUENCE: 37

Met Ala Ala Thr Gly Val Gly Ala Gly Cys Leu Ala Pro Ser Val Arg
1               5                   10                  15

Leu Arg Ala Asp Pro Ala Thr Ala Ala Arg Ala Ser Ala Cys Val Val
              20                  25                  30

Arg Ala Arg Leu Arg Arg Leu Ala Gly Arg Tyr Val Ala Glu Leu
          35                  40                  45

Ser Arg Glu Gly Pro Ala Ala Arg Pro Ala Gln Gln Gln Leu Ala
     50                  55                  60

Pro Pro Leu Val Pro Gly Phe Leu Ala Pro Pro Pro Ala Pro Ala

```
                65                  70                  75                  80
            Gln Ser Pro Ala Pro Thr Gln Pro Pro Leu Pro Asp Ala Gly Val Gly
                            85                  90                  95
            Glu Leu Ala Pro Asp Leu Leu Leu Glu Gly Ile Ala Glu Asp Ser Ile
                           100                 105                 110
            Asp Ser Ile Ile Val Ala Ala Ser Glu Gln Asp Ser Glu Ile Met Asp
                           115                 120                 125
            Ala Asn Glu Gln Pro Gln Ala Lys Val Thr Arg Ser Ile Val Phe Val
                           130                 135                 140
            Thr Gly Glu Ala Ala Pro Tyr Ala Lys Ser Gly Leu Gly Asp Val
            145                 150                 155                 160
            Cys Gly Ser Leu Pro Ile Ala Leu Ala Ala Arg Gly His Arg Val Met
                           165                 170                 175
            Val Val Met Pro Arg Tyr Leu Asn Gly Ser Ser Asp Lys Asn Tyr Ala
                           180                 185                 190
            Lys Ala Leu Tyr Thr Ala Lys His Ile Lys Ile Pro Cys Phe Gly Gly
                           195                 200                 205
            Ser His Glu Val Thr Phe Phe His Glu Tyr Arg Asp Asn Val Asp Trp
                           210                 215                 220
            Val Phe Val Asp His Pro Ser Tyr His Arg Pro Gly Ser Leu Tyr Gly
            225                 230                 235                 240
            Asp Asn Phe Gly Ala Phe Gly Asp Asn Gln Phe Arg Tyr Thr Leu Leu
                           245                 250                 255
            Cys Tyr Ala Ala Cys Glu Ala Pro Leu Ile Leu Glu Leu Gly Gly Tyr
                           260                 265                 270
            Ile Tyr Gly Gln Asn Cys Met Phe Val Val Asn Asp Trp His Ala Ser
                           275                 280                 285
            Leu Val Pro Val Leu Leu Ala Ala Lys Tyr Arg Pro Tyr Gly Val Tyr
                           290                 295                 300
            Arg Asp Ser Arg Ser Thr Leu Val Ile His Asn Leu Ala His Gln Gly
            305                 310                 315                 320
            Val Glu Pro Ala Ser Thr Tyr Pro Asp Leu Gly Leu Pro Pro Glu Trp
                           325                 330                 335
            Tyr Gly Ala Leu Glu Trp Val Phe Pro Glu Trp Ala Arg Arg His Ala
                           340                 345                 350
            Leu Asp Lys Gly Glu Ala Val Asn Phe Leu Lys Gly Ala Val Val Thr
                           355                 360                 365
            Ala Asp Arg Ile Val Thr Val Ser Gln Gly Tyr Ser Trp Glu Val Thr
                           370                 375                 380
            Thr Ala Glu Gly Gly Gln Gly Leu Asn Glu Leu Leu Ser Ser Arg Lys
            385                 390                 395                 400
            Ser Val Leu Asn Gly Ile Val Asn Gly Ile Asp Ile Asn Asp Trp Asn
                           405                 410                 415
            Pro Thr Thr Asp Lys Cys Leu Pro His His Tyr Ser Val Asp Asp Leu
                           420                 425                 430
            Ser Gly Lys Ala Lys Cys Lys Ala Glu Leu Gln Lys Glu Leu Gly Leu
                           435                 440                 445
            Pro Val Arg Glu Asp Val Pro Leu Ile Gly Phe Ile Gly Arg Leu Asp
                           450                 455                 460
            Tyr Gln Lys Gly Ile Asp Leu Ile Lys Met Ala Ile Pro Glu Leu Met
            465                 470                 475                 480
            Arg Glu Asp Val Gln Phe Val Met Leu Gly Ser Gly Asp Pro Ile Phe
                           485                 490                 495
```

```
Glu Gly Trp Met Arg Ser Thr Glu Ser Ser Tyr Lys Asp Lys Phe Arg
                500                 505                 510

Gly Trp Val Gly Phe Ser Val Pro Val Ser His Arg Ile Thr Ala Gly
            515                 520                 525

Cys Asp Ile Leu Leu Met Pro Ser Arg Phe Glu Pro Cys Gly Leu Asn
        530                 535                 540

Gln Leu Tyr Ala Met Gln Tyr Gly Thr Val Pro Val His Gly Thr
545                 550                 555                 560

Gly Gly Leu Arg Asp Thr Val Glu Thr Phe Asn Pro Phe Gly Ala Lys
                565                 570                 575

Gly Glu Glu Gly Thr Gly Trp Ala Phe Ser Pro Leu Thr Val Asp Lys
            580                 585                 590

Met Leu Trp Ala Leu Arg Thr Ala Met Ser Thr Phe Arg Glu His Lys
        595                 600                 605

Pro Ser Trp Glu Gly Leu Met Lys Arg Gly Met Thr Lys Asp His Thr
    610                 615                 620

Trp Asp His Ala Ala Glu Gln Tyr Glu Gln Ile Phe Glu Trp Ala Phe
625                 630                 635                 640

Val Asp Gln Pro Tyr Val Met
                645

<210> SEQ ID NO 38
<211> LENGTH: 643
<212> TYPE: PRT
<213> ORGANISM: Hordeum vulgare

<400> SEQUENCE: 38

Met Ala Ala Thr Gly Val Gly Ala Gly Cys Leu Ala Pro Ser Val Arg
1               5                   10                  15

Leu Arg Ala Asp Pro Ala Ala Arg Ala Thr Ala Cys Val Val Arg Ala
                20                  25                  30

Arg Leu Arg Arg Val Ala Arg Gly Arg Tyr Val Ala Glu Leu Ser Arg
            35                  40                  45

Glu Gly Pro Ala Ala Arg Pro Ala Gln Gln Leu Ala Pro Pro Val Val
        50                  55                  60

Pro Gly Phe Leu Ala Pro Pro Pro Ala Pro Ala Gln Ser Pro Ala
65              70                  75                  80

Pro Thr Gln Pro Pro Leu Pro Asp Ala Gly Val Gly Glu Leu Ala Pro
                85                  90                  95

Asp Leu Leu Leu Glu Gly Ile Ala Glu Asp Ser Ile Asp Thr Ile Val
            100                 105                 110

Val Ala Ala Ser Glu Gln Asp Ser Glu Ile Met Asp Ala Asn Asp Gln
        115                 120                 125

Pro Leu Ala Lys Val Thr Arg Ser Ile Val Phe Val Thr Gly Glu Ala
    130                 135                 140

Ala Pro Tyr Ala Lys Ser Gly Gly Leu Gly Asp Val Cys Gly Ser Leu
145                 150                 155                 160

Pro Ile Ala Leu Ala Ala Arg Gly His Arg Val Met Val Met Pro
                165                 170                 175

Arg Tyr Leu Asn Gly Thr Ser Asp Lys Asn Tyr Ala Lys Ala Leu Tyr
            180                 185                 190

Thr Gly Lys His Ile Lys Ile Pro Cys Phe Gly Gly Ser His Glu Val
        195                 200                 205

Thr Phe Phe His Glu Tyr Arg Asp Asn Val Asp Trp Val Phe Val Asp
```

```
                210                 215                 220
His Pro Ser Tyr His Arg Pro Gly Ser Leu Tyr Gly Asp Asn Phe Gly
225                 230                 235                 240

Ala Phe Gly Asp Asn Gln Phe Arg Tyr Thr Leu Leu Cys Tyr Ala Ala
                245                 250                 255

Cys Glu Ala Pro Leu Ile Leu Glu Leu Gly Gly Tyr Ile Tyr Gly Gln
                260                 265                 270

Ser Cys Met Phe Val Val Asn Asp Trp His Ala Ser Leu Val Pro Val
        275                 280                 285

Leu Leu Ala Ala Lys Tyr Arg Pro Tyr Gly Val Tyr Arg Asp Ser Arg
290                 295                 300

Ser Thr Leu Val Ile His Asn Leu Ala His Gln Gly Val Glu Pro Ala
305                 310                 315                 320

Ser Thr Tyr Pro Asp Leu Gly Leu Pro Pro Glu Trp Tyr Gly Ala Leu
                325                 330                 335

Glu Trp Val Phe Pro Glu Trp Ala Arg Arg His Ala Leu Asp Lys Gly
                340                 345                 350

Glu Ala Val Asn Phe Leu Lys Gly Ala Val Val Thr Ala Asp Arg Ile
                355                 360                 365

Val Thr Val Ser Gln Gly Tyr Ser Trp Glu Val Thr Thr Ala Glu Gly
        370                 375                 380

Gly Gln Gly Leu Asn Glu Leu Leu Ser Ser Arg Lys Ser Val Leu Asn
385                 390                 395                 400

Gly Ile Val Asn Gly Ile Asp Ile Asn Asp Trp Asn Pro Thr Thr Asp
                405                 410                 415

Lys Cys Leu Pro His His Tyr Ser Val Asp Asp Leu Ser Gly Lys Ala
                420                 425                 430

Lys Cys Lys Ala Glu Leu Gln Arg Glu Leu Gly Leu Pro Val Arg Glu
        435                 440                 445

Asp Val Pro Leu Ile Gly Phe Ile Gly Arg Leu Asp Tyr Gln Lys Gly
450                 455                 460

Ile Asp Leu Ile Lys Met Ala Ile Pro Asp Leu Met Arg Glu Asp Val
465                 470                 475                 480

Gln Phe Val Met Leu Gly Ser Gly Asp Pro Val Phe Glu Gly Trp Met
                485                 490                 495

Arg Ser Thr Glu Ser Ser Tyr Lys Asp Lys Phe Arg Gly Trp Val Gly
                500                 505                 510

Phe Ser Val Pro Val Ser His Arg Ile Thr Ala Gly Cys Asp Ile Leu
        515                 520                 525

Leu Met Pro Ser Arg Phe Glu Pro Cys Gly Leu Asn Gln Leu Tyr Ala
530                 535                 540

Met Gln Tyr Gly Thr Val Pro Val Val His Gly Thr Gly Gly Leu Arg
545                 550                 555                 560

Asp Thr Val Glu Thr Phe Asn Pro Phe Gly Ala Lys Gly Glu Glu Gly
                565                 570                 575

Thr Gly Trp Ala Phe Ser Pro Leu Thr Val Glu Lys Met Leu Trp Ala
                580                 585                 590

Leu Arg Thr Ala Ile Ser Thr Phe Arg Glu His Lys Pro Ser Trp Glu
        595                 600                 605

Gly Leu Met Lys Arg Gly Met Thr Lys Asp His Thr Trp Asp His Ala
        610                 615                 620

Ala Glu Gln Tyr Glu Gln Ile Phe Glu Trp Ala Phe Val Asp Gln Pro
625                 630                 635                 640
```

Tyr Val Met

<210> SEQ ID NO 39
<211> LENGTH: 1936
<212> TYPE: DNA
<213> ORGANISM: Vitis vinifera
<220> FEATURE:
<221> NAME/KEY: misc_feature
<222> LOCATION: (1)..(1936)
<223> OTHER INFORMATION: Codon optimized sequence for Vitis vinifera SSS
      gene

<400> SEQUENCE: 39

| | | | | |
|---|---|---|---|---|
| ggatccgttt | aaacgccacc | atggagagcc | tgcaatcgcc | cctggtgctg | tcgtctaagc | 60 |
| tgctgcctaa | ctcgctgaag | aagcccgtcc | tggaggttgg | gttcgcttgc | ttcttcaagc | 120 |
| aaaggcgcgt | catccagtct | gtttccatca | agaggtctgt | ggtctgctgc | tccagaaagg | 180 |
| gcggggggcgg | gggctcgcaa | gacggctcca | gcgcgatgct | ggtgaacacc | gacaagaagg | 240 |
| atgctagcga | ctcggtcggc | ttccacctcg | ttccacctcc | tagcggcgat | aacggggtca | 300 |
| tcgacccgca | tgagaagctc | tcgacccaga | aggaggccga | gacgggcaac | tcagaggggg | 360 |
| aggaggagag | gaagaccaag | gtgacgtaca | acatcgtgtt | cgtcacctca | gagtctgctc | 420 |
| catactctaa | gacgggggc | ctgggcgacg | tgtgcgggtc | cctgccgatc | gccctcgccg | 480 |
| cgcacggcca | tcgggtcatg | gttgtgtccc | ccagatacca | aaacggcacc | tgcagcgatg | 540 |
| agatcttctc | cggggctagc | gacctcgagc | acccgatcaa | ggtgcattgc | ttcggggggcg | 600 |
| tccaggaggt | ttccttcttc | cacgagtacc | gggcgggcgt | cgattgggtt | ttcgtggacc | 660 |
| accccagcta | ccataggcct | ggcaacccctt | acggcgatgg | gtacggcgct | ttcggcgaca | 720 |
| accaattccg | cttcacccctc | ctgtgccacg | ctgcttgcga | ggctcctctc | gttctgcctc | 780 |
| tcggggggctt | cacctacggc | gagaagtgcc | tgttcctcgt | caacgactgg | cacgcttccc | 840 |
| tcgtccctgt | tctcctggct | gctaagtaca | ggcctcatgg | cgtgtacaag | gatgcgcgca | 900 |
| ccgtgctggt | catccacaac | ctcgcccatc | aaggcgtgga | gcctgcggtc | acgtacgaca | 960 |
| acctgggcct | ccctccagag | tggtacggggg | ccgtggagtg | ggtcttccca | acctgggcta | 1020 |
| gaacgcacgc | tctcgacacc | ggccaggctg | tcaacctcct | gaaggggggcc | atcgttaccg | 1080 |
| tggatcgcat | cctcacggtg | tccaagggct | acgcttggga | ggtcaccacg | cctgaggggg | 1140 |
| gctacggcct | ccacgagctc | ctgacctcaa | ggaaggcggt | tatcaacggc | atcacgaacg | 1200 |
| ggatcgacgt | gtctgagtgg | gatcaatcgt | cagacgagca | catcccattc | cattacagcg | 1260 |
| ccgaggatct | gtcgggcaag | gtgcaatgca | agatcgcgct | ccagaaggag | ctgagcctcc | 1320 |
| ctatccggcc | agactgcccg | ctgatcggct | tcatcgggag | actcgattac | caaaagggca | 1380 |
| tcgacgtgat | caggctggct | acccctgagc | tcatgggcga | ggatgttcag | ctcgtgatgc | 1440 |
| tcgggagcgg | caaccctgag | gacgaggagt | ggatgcgcgt | catggagtcg | acctacaggg | 1500 |
| ataagttccg | cggctgggtt | gggttcaacg | tgccaatctc | acaccgcatc | accgcctctt | 1560 |
| gcgacatcct | cctgatgcca | tccagattcg | agccttgcgg | cctgaaccag | ctctacgcga | 1620 |
| tgagatacgg | cgctgtccct | gtcgttcatg | gaccggggg | cctgagggac | acggttgaga | 1680 |
| acttcaaccc | ttacgctggg | ggggggtccg | gggagggcac | cgggtggacg | ttctcgccac | 1740 |
| tctcaaagga | caccatgctg | gctgctctca | gagtggctat | ccggacgtac | agagagcaca | 1800 |
| agccatcatg | ggagcggctg | atgaagagag | gcatggagaa | ggattacacc | tgggacaagg | 1860 |
| ccgcgctgga | gtacgagcaa | gtgttcaagt | gggctttcat | cgacccccccc | tacgtgtcct | 1920 | gagtttaaac ggatcc                                                    1936

<210> SEQ ID NO 40
<211> LENGTH: 1984
<212> TYPE: DNA
<213> ORGANISM: Poplar triocarpa
<220> FEATURE:
<221> NAME/KEY: misc_feature
<222> LOCATION: (1)..(1984)
<223> OTHER INFORMATION: Codon optimized sequence for Poplar triocarpa
      SSS gene

<400> SEQUENCE: 40

| | | | | | | |
|---|---|---|---|---|---|---|
| ggatccgttt | aaacgccacc | atggagtctc | tctgcatcgt | tgggaacggg | ggggttagca | 60 |
| cctgccaggc | tttcacgagg | ctggacacca | cgagggtcgg | cttcaggcct | agagctcaac | 120 |
| tgggcttcgg | gtgcttcgtc | cgggagagat | acaagtacgg | caacctcgtt | atcgcccgct | 180 |
| cagggcgctc | tgaagtgggc | aacagcaagg | acgggaactt | cgcggtggag | acgagaaga | 240 |
| aggagaagag | aggcgggctc | atcctgggcc | ctgagagaga | ctccagcggg | tcgatcatcg | 300 |
| gcttcaacct | gatcccaccg | tccggcatgg | acatcagctt | caccgtcctc | gagtcacacg | 360 |
| aggatgctac | cacgggcggg | acggaggagg | ctgaggacat | cgagggcgtg | gagaaggtcc | 420 |
| agaccagggt | gacgtacaac | atcgtcttcg | ttacctcgga | ggctgctcct | tactcaaaga | 480 |
| cgggcgggct | cggggacgtc | tgcggcagcc | tgcctatcgt | tctcgctgct | agaggccaca | 540 |
| gagtcatggt | ggtctctcct | cgctacctgc | atggctcccc | agcggacaag | aacttcgcgg | 600 |
| gggcttcgga | gctcgattgc | cacatcaagg | tctactgctt | cggcggggag | caagaggttg | 660 |
| ccttcttcca | tgagtaccgg | gagggcgtgg | actgggtgtt | cgtcgatcac | ccaagctacc | 720 |
| ataggcctgg | gaacccttac | ggcgactcga | gagggctttc | ggcgataac | cagttccggt | 780 |
| tcgctctcct | gtgccacgct | gcttgcgagg | ctcctctcgt | cctgccactc | ggcgggtaca | 840 |
| cctacggcga | gaagtgcctg | ttcctcgtta | cgactggca | tgctggcctg | gttcctgtgc | 900 |
| tcctggctag | caagtacaga | ccctacggcg | tgtacaagga | cgcgaggacc | atcctggtca | 960 |
| tccacaacct | cgctcatcaa | ggcgttgagc | ctgccgcgac | ctacacgaac | ctgggcctcc | 1020 |
| catccgagtg | gtacggggct | ctgggctggg | tcttccctac | ctgggctaga | acgcacgctc | 1080 |
| tcgataccgg | cgaggctgtg | aacctcctga | aggggggctat | cgtcaccgtt | gaccgcatcc | 1140 |
| tcacggtgtc | taagggctac | gcttgggaga | tcaccacggt | cgagggcggc | tacggcctgc | 1200 |
| acgagctcct | gtcgtcaagg | cgctccgtgc | tcaacgggat | caccaacggc | atcgacatct | 1260 |
| acgagtggaa | cccatcttcc | gataagcata | tcgcttccaa | ctacagcgtg | gacgatctgt | 1320 |
| ccggcaaggt | ccaatgcaag | atcgccctcc | agaaggagct | gggcctccca | atcaagccgg | 1380 |
| actgccctct | gatcgggttc | atcggcagac | tcgactacca | aaagggcatc | gatctcatca | 1440 |
| gatgggctac | ccctgagctc | ctggaggacg | atgttcagtt | cgtgatgctg | ggctcagggg | 1500 |
| acccccctcta | cgaggattgg | atgagagcca | ccgagtctac | gtacaaggat | aagttcaggg | 1560 |
| ggtgggtggg | cttcaacatc | cctatctccc | acaagatcac | cgctggcgct | gacatcctcc | 1620 |
| tgatgcctag | cagattcgag | ccttgcggcc | tgaaccaact | ctacgcgatg | cggtacggca | 1680 |
| ccgttccagt | tgtgcatggg | accggcgggc | tcagagacac | ggtgcaggcc | ttcgatcctt | 1740 |
| actcaaaggg | cgggctgggc | gaggggaccg | gctggatctt | ctcgccactc | tcaaaggagt | 1800 |
| ctatgctggc | tgccctcagg | gtcgcgatca | tgacctaccg | cgatcacaag | agctcgtggg | 1860 |
| agggcatcat | gaagagggggg | atggtgaagg | actccacgtg | ggagaacgcc | gctgtccatt | 1920 |

```
acgagcaggt gttcgagtgg gctttcatcg acccgccata catcaactga gtttaaacgg    1980
atcc                                                                  1984

<210> SEQ ID NO 41
<211> LENGTH: 1924
<212> TYPE: DNA
<213> ORGANISM: Sorghum bicolor
<220> FEATURE:
<221> NAME/KEY: misc_feature
<222> LOCATION: (1)..(1924)
<223> OTHER INFORMATION: Codon optimized sequence for Sorghum bicolor
      SSS gene

<400> SEQUENCE: 41
ggatccgttt aaacgccacc atggctacgc cttccgctgt cggggctgct tgcctggttc      60
tggctcgggc tgctgctggg ctgggctcg gccggggag gggggcgac agagctaggc     120 ctaggagatt ccaaagagtg gtccggagac gctgcgtggc tgagctgagc agagagggcc    180
ctgctccaac cccgaggcct ctcccacctg ctctcctggc cctcctctg gtcccagctt     240 tcctcgctcc acctagcgag cctgagggcg agcctgcgtc acccccccct ccactgcctg    300
acgctggcct cggggatctc ggcctgcaac ctgagggcat cgctgagggg tccatcgacg    360
agacggttgt ggtcgcgagc gagcaggatt cggagatcgt tgtgggcaag gagcaagcca    420
gggcgaaggt gacccagtcc atcgtgttcg tcacggcga ggcgtcgcca tacgctaagt     480
caggcgggct gggcgacgtt tgcgggagcc tgcctgtggc tctcgctgct agaggccacc    540
gggtcatggt cgttatgccc agatacctca acgggacctc cgacaagaac tacgctaacg    600
ccttctacac ggagaagcat atccgcatcc catgcttcgg cggggagcac gaggtcacct    660
tcttccatga gtaccgcgac tcagttgatt gggttttcgt ggaccaccca tcttaccatc    720
ggccgggcaa cctctacggg gacaagttcg gcgccttcgg ggataaccaa ttccgctaca    780
ccctcctgtg ctacgctgct tgcgaggctc cactcgtgct ggagctcggc gggtacatct    840
acggccagaa ctgcatgttc gtggtcaacg actggcacgc ttcgctcgtc ccagttctcc    900
tggctgctaa gtaccgcccg tacggcgtct caaggattc gcggtcaatc ctggttatcc    960
acaacctcgc tcatcaaggc gtggagcctg cttcaaccta ccctgacctg gcctcccctc   1020
ctgagtggta cggggccctc gagtgggtgt tcccagagtg gctagaaga cacgctctgg    1080 acaagggcga ggcggtcaac ttcctcaagg gggctgttgt gaccgccgat cgcatcgtga   1140
cggtctcaaa gggctactct tgggaggtga ccacggctga gggcgggcag gggctgaacg    1200
agctcctgtc cagccggaag tccgtgctca acggcatcgt caacgggatc gacatcaacg    1260
attggaaccc cgccaccgac aagtgcatcc cttgccacta ctctgtggac gatctgtccg    1320
gcaaggcgaa gtgcaagagc gctctccaaa aggagctggg cctccctatc agaccagagg    1380
tcccgctgat cggcttcatc gggaggctcg actaccaaaa gggcatcgat ctgatccagc    1440
tcatcatccc gcatctcatg cgcgacgatg tccagttcgt tatgctgggc tcggggggacc    1500 ccgagctcga ggattggatg cgctctaccg agtccgactt caaggataag ttccggggct    1560
gggtggggtt ctccgttcca gtgagccaca gaatacgggc cggctgcgac atcctcctga    1620
tgccatccag gttcgagccg tgcggcctga accaactcta cgccatgcag tacgggaccg    1680
tgcctgtcgt tcatgctacc ggcgggctga gggacacggt cgagaacttc aaccctttcg    1740
gcgagaacgg ggagcagggc accgggtggg cttcgctcc actcaccacg gagaacatgt    1800
tcgtcgacat cgccaactgc aacttcgata tccaaggcgc gcagatcttc ctgggcaggg    1860
```

```
cgcacgagga ggggcatgtg aagcggctcc acgtcgggcc ttgcaggtga gtttaaacgg   1920
atcc                                                                1924
```

EXPRESSION OF THERMOSTABLE STARCH SYNTHASE GENES IMPROVES THE YIELD IN HEAT STRESS

CROSS-REFERENCE TO RELATED APPLICATIONS

The present application is a divisional of U.S. Ser. No. 14/911,990, filed Feb. 12, 2016, which is the National Stage of International Patent Application No. PCT/US2014/050932, filed Aug. 13, 2014, which claims the priority benefit of U.S. Provisional Patent Application Ser. No. 61/865,767, filed Aug. 14, 2013, entitled EXPRESSION OF THERMOSTABLE STARCH SYNTHASE GENES IMPROVES THE YIELD IN HEAT STRESS, each of which is incorporated by reference in its entirety herein.

SEQUENCE LISTING

The following application contains a sequence listing in computer readable format (CRF), submitted as a text file in ASCII format entitled "Sequence Listing," created on Aug. 12, 2014, as 133 KB. The content of the CRF is hereby incorporated by reference. Only one strand of each nucleic acid sequence is shown, but the complementary strand is understood as included by any reference to the displayed strand.

BACKGROUND OF THE INVENTION

Field of the Invention

The present invention relates to genetically-modified plants having increased tolerance and yield under heat stress.

Description of Related Art

Starch synthase (SS), including soluble starch synthase (SSS), is a key enzyme in starch deposition and storage in plants. Starch synthesis occurs in plastids of leaves during daylight using carbon fixed through photosynthesis, which is then mobilized to the storage organs at night. Starch consists of two D-glucose homopolymers: amylose and amylopectin. Amylose is a linear chain of a (1-4) linked D-glucose monomers and generally makes up ~30% of starch. Amylopectin is a highly branched monomer joining linear chains made by α (1-6) linkages. Starch biosynthesis occurs in chloroplasts in green photosynthetic tissues, and in non-green tissue amyloplasts, such as endosperm. In the endosperm of a seed, biosynthesis of amylopectin requires a properly coordinated series of enzymatic reactions which involve the enzymes including ADP glucose pyrophosphorylase (AGPase), four different soluble starch synthases (SSI-IV), starch branching enzyme (BE), and starch debranching enzyme (DBE), whereas amylose biosynthesis requires only AGPase and granule-bound starch synthase (GBSS). There is a possibility that plastidial starch phosphorylase (Pho1) also plays an important role in primer formation in the starch biosynthesis reaction. In higher plants, AGPase produces ADP-Glc and pyrophosphate (PPi) from Glc-1-P and ATP. Starch synthase enzymes make linear glucan chains by transferring glucosyl units of ADP-Glc to the non-reducing end of a glucan chain. In cereal endosperm, a number of isoforms of starch synthase enzymes have been identified, including GBSS, SSI, SSII, SSIII and SSIV. GBSS has two isoforms that are mostly confined to storage tissue and involved in amylose synthesis, whereas different starch synthase isoforms, along with some amylose, are predominantly involved in formation of amylopectin. In rice, SSIIa and SSIIIa transcripts are most abundant during the grain filling phase, meanwhile SSIIb and SSIIIb transcripts are found in the pre-storage phase, indicating that SSIIa and SSIIIa may play vital roles in starch biosynthesis in rice compared to other SS enzymes. The presence of any one of the SSI or SSIIIa genes can continue starch biosynthesis in rice, although rice has only one SSI isoform. SSI has been shown to have higher activity than SSIIIa, and accounts for almost 70% of the total SS activity. Similar results have been found for the soluble fraction of wheat developing endosperm and maize endosperm. These observations suggest that SSI is critical for starch biosynthesis. SSI preferentially synthesizes short sequences, while further chain elongation of amylopectin synthesis is performed by other SS enzymes.

Wheat (*Triticum aestivum* L.) is the most important staple crop for approximately 36% of the world's population. In a dry wheat seed, starch is the most abundant element accounting for 75-85% of grain dry weight. Thus, the grain yield (based upon seed number per unit area and individual seed weight) is largely dependent on starch deposition in the growing endosperm. However, elevated temperature has significant adverse effects on starch deposition in the endosperm during the grain filling stage of different crops, possibly by inactivating soluble starch synthase. For example, temperatures above 25° C. significantly reduce soluble starch synthase enzyme activity in the wheat endosperm. Of the total wheat production in the world, 40% is affected by terminal heat stress. Heat stress usually affects wheat production by reducing the yield and quality. Thus, there is a need in the art for improving the heat tolerance of various plants, including wheat, to heat stress.

SUMMARY OF THE INVENTION

The present invention is broadly concerned with genetically-modified plants having increased tolerance to heat stress as compared to a control plant. The genetically-modified plants comprise exogenous nucleic acid encoding a thermostable protein having starch synthase activity.

Methods of increasing tolerance to heat stress in a plant are also provided. The methods comprise transforming a plant with an exogenous nucleic acid encoding a thermostable protein having starch synthase activity to yield a transformed plant, thereby increasing the heat stress tolerance of the transformed plant.

Additional methods of producing genetically-modified plants having increased tolerance to heat stress as compared to a control plant are also described. The methods comprise crossing a first parent plant with a second parent plant to thereby produce progeny, wherein at least one of the first or second parent plants is a genetically-modified plant as described herein. Advantageously, the progeny have increased tolerance to heat stress as compared to a control plant. Genetically-modified seed produced according to the described methods are also disclosed.

Recombinant plant cells are also disclosed herein. The recombinant plant cells have ectopic expression of an exogenous thermostable protein having starch synthase activity by stable transformation with a nucleic acid construct encoding the thermostable protein. Additional features of the various embodiments of the invention are described in more detail below.

BRIEF DESCRIPTION OF THE DRAWINGS

Figure (FIG. 1 illustrates: (a) Construct pAHC17 containing Ubip (maize ubiquitin promoter), SSI-cDNA from rice soluble starch synthase 1 gene, and NosT (nopaline synthase gene terminator); (b) Construct pJL10P5 having rice soluble starch synthase 1 gene, and DY10 (high molecular weight glutenin promoter); and (c) Construct pAHC20 having BAR gene which confers resistance to the herbicide glufosinate and bialaphos.

DETAILED DESCRIPTION OF PREFERRED EMBODIMENTS

Figure 1:
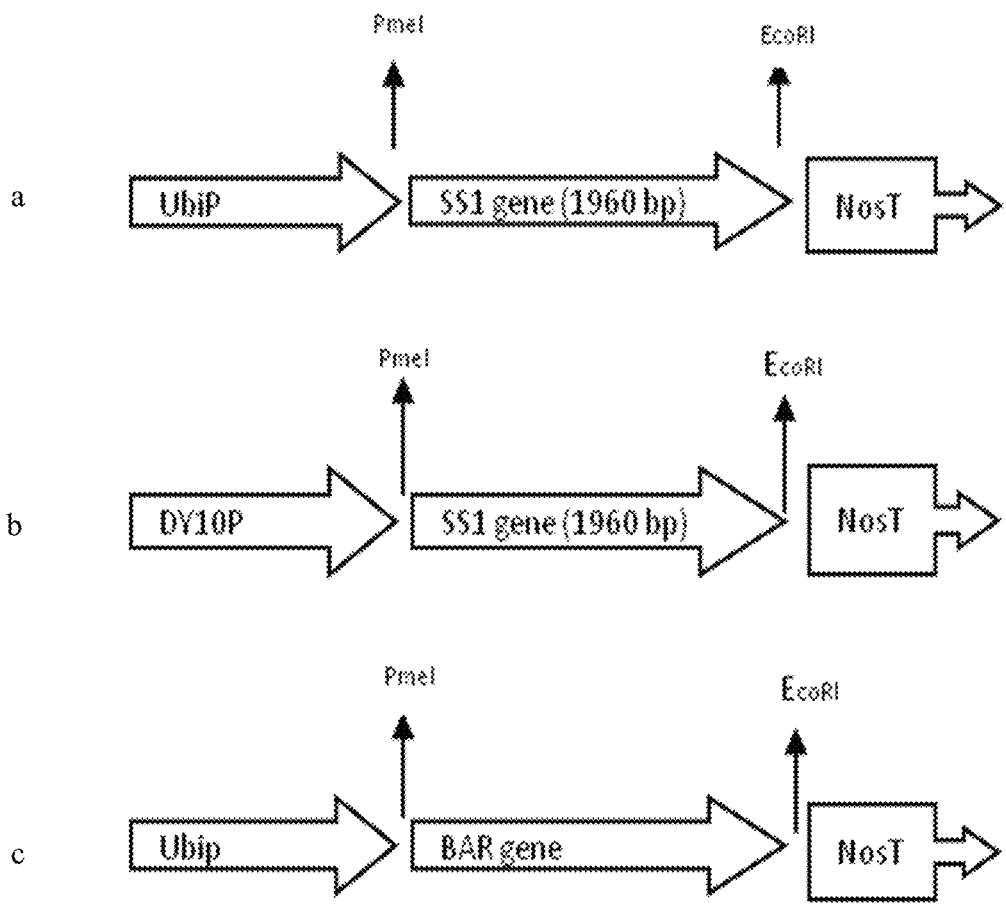

In more detail, the present invention is concerned with genetically-modified plants and methods of making and using the same to increase tolerance to heat stress in plants. Unless otherwise indicated by the context, references herein to a "plant" or "plants" includes tissues, organs, or parts thereof (e.g., leaves, stems, tubers, shoots, roots, blooms, buds), fruit, or cells thereof. Methods of creating such non-naturally occurring, genetically-modified plants (aka "transgenic" plants) are also provided, along with nucleic acid constructs and vectors useful in such methods. The invention is suitable for use with various plants, including both monocotyledons (i.e., plants having one cotyledon (seed-leaf), aka "monocots") and dicotyledons (i.e., plants having two cotyledons, aka "dicots"). Non-limiting examples of plants suitable for the disclosed embodiments include grains (e.g., wheat, oat, barley, rice, maize, millet, rye, sorghum, triticale, buckwheat, quinoa), legumes (e.g., soybeans, beans, peas, alfalfa), tubers (e.g., potatoes, sweet potatoes, cassava, yam), and the like.

Heat stress occurs when a plant is subjected to elevated growing temperatures at least about 7° C. higher than the normal plant growing temperatures for short durations such as hours or days and at least about 4° C. higher for longer durations such as days and weeks. The present invention is particularly concerned with increasing tolerance to elevated temperatures encountered during the starch synthesis phase of plant growth (e.g., seed-filling stage). The term "elevated" growing temperatures, in the context of the invention, refers to temperatures at or above which plant growth and/or yield, including endogenous starch synthase activity in the plant, is decreased or inactivated. "Normal" plant growing conditions or temperatures refers to condition or temperature ranges suggested for optimal growth and/or yield, which for most species are known in the art. For example, plants such as wheat prefer an optimal temperature of between about 15° C. and about 20° C. The optimum temperature for growth for plants such as maize is between about 20° C. and about 23° C. Plants such as sorghum prefer a daytime temperature of between about 25° C. and about 28° C. for reproductive growth. Plants such as soybean prefer a daytime temperature of about 29° C. In general, preferred nighttime temperatures for most plants are about 2° C. to about 5° C. lower than daytime temperatures.

Genetically-modified plants according to the invention have increased tolerance to heat stress, where the term "tolerance" refers to the ability of the plant to continue growing and producing yield outside of its normal plant growing conditions. The heat tolerance of a transgenic plant is considered to be "increased" when the transgenic plant's growth, development, and/or yield is superior to the growth, development, and/or yield of a control plant under the elevated growing temperatures, even if the transgenic plant is not completely resistant to or unaffected by the heat stress. Increased "yield" will depend upon the particular species of the modified plant and may manifest itself as one or more of the following: a) an increase in total seed weight, size, or volume, on an individual seed basis and/or per plant and/or per acre; b) increased thousand kernel weight (TKW), which is the weight in grams of one thousand kernels of wheat; c) increased number of flowers per plant; d) increased biomass; and/or e) increased harvest index, which is expressed as a ratio of the yield of harvestable parts, such as seeds, divided by the total biomass. An increased TKW may result from an increased seed size and/or seed weight, and may also result from an increase in embryo and/or endosperm size. The present invention is particularly concerned with improved plants having increased yield as compared to control plants grown under elevated temperatures during the starch synthesis stage of plant development.

Advantageously, unlike many other transgenic plants, plants according to the invention have a phenotype/morphology that is otherwise substantially similar to, and in some cases, nearly identical to wild type plants of the same species (when such wild type plants are grown under non-stress conditions). In other words, the shape, size, and/or abundance of seed, foliage and/or fruit/vegetable is substantially similar between the transgenic plants and wild type plants. Plants are considered to be "substantially similar" herein if those skilled in the art have difficulty visually distinguishing between the genetically-modified plant and the control plant when grown under identical normal growing conditions. In contrast, when grown under heat stress, transgenic plants according to the various embodiments of the invention, have significantly improved morphologies as compared to control plants grown under the same conditions. For example, the transgenic plant may have one or more of the following improved morphological or physical characteristics as compared to a control plant: vigorous growth, abundant foliage, longer primary roots, height, etc. when grown under heat stress. Thus, there is no detrimental effect on morphology or phenotype in the genetically-modified plants.

The genetically-modified plants comprise an exogenous nucleic acid encoding for a thermostable protein having starch synthase activity, and preferably soluble starch synthase activity. The term "soluble starch synthase activity" or "starch synthase activity" refers to protein/enzyme biosynthesis of starch, such as soluble starch. The term "exogenous" is used herein to refer to a nucleic acid sequence (e.g., DNA, RNA), gene, or protein that originates from a source outside of (i.e., foreign to) the host plant into which it is introduced to create the transgenic plant. For example, the term as it is used in reference to expression of an encoding nucleic acid, refers to introduction of an exogenous encoding nucleic acid in an expressible form into the host plant. In other words, the nucleic acid is not native to and/or has not been derived from that particular plant. In contrast, the term "endogenous" is used herein interchangeably with "native" and refers to nucleic acid sequences, genes, gene products, proteins, etc. that are naturally associated with or found in a control or wild-type plant.

In one or more embodiments, the exogenous nucleic acid encoding the thermostable starch synthase protein is also heterologous. The term "heterologous" refers to genetic material derived from a source other than the referenced species, and is contrasted with "homologous," which refers to genetic material derived from, naturally associated with, or native to, the species of the host plant (although not necessarily to the host plant itself). For example, in some embodiments of the invention, the transgenic plants are created by introducing genetic material encoding for a starch synthase from one species into a host plant of a different species, wherein the host plant expresses that heterologous gene product. Thus, since an exogenous nucleic acid molecule is heterologous with respect to the host plant, the transformed plant cells will contain transcripts of the nucleic acid molecules introduced that would not be detected in a control plant qualitatively or quantitatively (e.g., by PCR). If, on the other hand, an exogenous nucleic acid molecule is homologous with respect to the host plant, the transformed plants can be distinguished from control plants based upon additional expression of transcripts, which can be detected using "quantitative" PCR techniques. In the present invention, it is particularly advantageous to introduce heterologous nucleic acids encoding starch synthase, which are native to more heat tolerant or tropical plant species into more moderate, temperate, or cool weather plant species to increase their tolerance to heat stress. The starch synthase coding sequence can be isolated from the more heat tolerant plant, or a synthetic coding sequence (e.g., cDNA) can be synthesized based upon available genetic information for the more heat tolerant plants. Advantageously, expression or overexpression of the exogenous thermostable starch synthase increases the tolerance of the transformed plant to heat stress.

A protein is considered to be "thermostable" when the protein remains enzymatically active, such that the function and/or activity of the protein is maintained at a given temperature (usually an elevated temperature) without significant decrease in activity. In other words, a protein is thermostable at a given elevated temperature if it maintains its native folded (functional) conformation and is not denatured or otherwise rendered non-functional at such temperatures. Thus, in the context of the present invention, thermostable proteins are selected such that they will maintain starch synthase activity in the transformed plant cell(s) under elevated growing temperatures—temperatures at or above which the endogenous starch synthase enzymes of the transformed plant typically have decreased starch synthase activity or even inactivity. That is, the exogenous thermostable proteins have a higher relative thermostability and are more "thermotolerant" than the endogenous proteins of the transformed plant. Suitable thermostable proteins can be selected for relative thermostability at temperatures ranging from about 4° C. to about 30° C. (and preferably 5° C. to about 15° C.) higher than the thermostability of the endogenous starch synthase enzymes of the host plant. For example, if the thermostability temperature of the endogenous starch synthase enzymes of the host plant is about 25° C., then the plant can be transformed using an exogenous thermostable protein having thermostability at about 30° C. to about 55° C. However, it will be appreciated that the thermotolerant SS protein must also remain enzymatically active throughout a range of growing temperatures, and not be inactivated at lower temperatures. In one or more embodiments, suitable thermostable proteins will be enzymatically active at temperatures greater than about 55° C., preferably from about 23° C. to about 55° C., and more preferably from about 23.5° C. to about 43.5° C. (75° F.-110° F.). Thus, starch synthase genes can be identified or isolated from plants having a higher relative thermostability and then used to transform plants having a lower intrinsic relative thermostability, thereby increasing the heat stress tolerance of the modified plant. Thermostability can be predicted using a publicly-available algorithm (ThermoRank, accessible via www dot abl dot ku dot edu/services) developed by Li et al. at the Kansas University Applied Bioinformatics Lab, and the relative thermostability of several species is shown in the working examples below. In one or more embodiments, starch synthase genes and/or starch synthase proteins native to plants such as rice, cottonwood, grapes, *sorghum*, soybean, maize, common beans, algae, clover, amaranth, *arabidopsis*, cocoa, tomatoes, cassava, alfalfa, chickpeas, and/or peaches can be used to increase the heat tolerance of less heat tolerance plants.

Transformation techniques for plants are well known in the art and include any technique involving the uptake of exogenous genetic material by the plant, such as particle bombardment-mediated delivery, *Agrobacterium*-mediated techniques, PEG- or electroporation-mediated uptake, viral infection, and/or microinjection.

In some embodiments, the tolerance to heat stress is increased by expressing in the plant a nucleic acid which comprises (or consists of): (a) a nucleotide sequence encoding a thermostable SS protein comprising (or consisting of) SEQ ID NO: 2, 4, 6, 8, 9, 10, 11, 12, 13, 14, 15, 16, 17, 18, 19, or 20, or (b) a nucleotide sequence encoding a thermostable SS protein having at least about 50% amino acid identity (preferably at least about 70% amino acid identity, and more preferably at least about 80% amino acid identity) to SEQ ID NO: 2, 4, 6, 8, 9, 10, 11, 12, 13, 14, 15, 16, 17, 18, 19, or 20, and retaining the functional characteristics thereof. The "functional characteristics" of the thermostable SS proteins refers to the ability of the expressed protein or enzyme to remain enzymatically active to synthesize (soluble) starch at the elevated growing temperatures. In one or more embodiments, the nucleic acid comprises (or consists of) a sequence selected from the group consisting of (a) a nucleotide sequence of SEQ ID NO: 1, 3, 5, or 7; and (b) a nucleotide sequence having at least about 70% sequence identity (preferably at least about 80% sequence identity, and more preferably at least about 90% sequence identity) to SEQ ID NO: 1, 3, 5, or 7 (i.e., conservatively modified variants thereof). Thus, "conserved variants" of the disclosed nucleic acid and amino acid sequences are contemplated herein, as long as the resulting proteins or enzymes retain starch synthase activity.

In one or more embodiments, the method of increasing the tolerance of a plant to heat stress comprises introducing and expressing in a plant cell a nucleic acid construct encoding thermostable protein having starch synthase activity. In one or more embodiments, the thermostable protein is starch synthase, preferably soluble starch synthase, and more preferably soluble starch synthase I. A recombinant plant cell comprising the nucleic acid construct, preferably stably incorporated into its genome, is also provided herein. The nucleic acid construct can comprise a nucleic acid coding sequence which is operably linked to a promoter that drives expression in the plant cell. Suitable promoters include constitutive promoters, as well as endosperm-specific promoters. Non-limiting examples of promoters include maize ubiquitin promoters, high molecular weight (HMW) glutenin promoter subunit (Dy10), the CaMV35S promoter, the soybean GMubi3 promoter, and/or rice actin promoter. More preferably, the transgenic plant is prepared by introducing into a plant cell a vector or plasmid comprising the nucleic acid construct. Thus, in one or more embodiments, a plant cell transformed with an expression vector or plasmid described herein is also provided. In further embodiments, a vector or plasmid is provided for preparing a transgenic plant having increased tolerance to heat stress. The vector or plasmid comprises an expression cassette comprising a nucleic acid construct encoding thermostable SS protein, operably linked a suitable promoter for driving expression of the nucleic acid in the plant cell.

In some embodiments, the nucleic acid construct comprises (or consists of) a sequence selected from the group consisting of: (a) a nucleotide sequence encoding for a thermostable SS protein comprising (or consisting of) SEQ ID NO: 2, 4, 6, 8, 9, 10, 11, 12, 13, 14, 15, 16, 17, 18, 19, or 20; (b) a nucleotide sequence encoding for a thermostable SS protein having at least about 50% amino acid identity (preferably at least about 70% amino acid identity, and more preferably at least about 80% amino acid identity) to SEQ ID NO: 2, 4, 6, 8, 9, 10, 11, 12, 13, 14, 15, 16, 17, 18, 19, or 20, and retaining the functional characteristics thereof; (c) a nucleotide sequence of SEQ ID NO: 1, 3, 5, or 7; and (d) a nucleotide sequence having at least about 70% sequence identity (preferably at least about 80% sequence identity, and more preferably at least about 90% sequence identity) to SEQ ID NO: 1, 3, 5, or 7 (i.e., conservatively modified variants thereof).

In some embodiments, there is provided an isolated nucleotide sequence encoding a thermostable protein having starch synthase activity for increasing heat stress tolerance in plants. In some embodiments, the nucleotide sequence comprises a sense sequence corresponding to SEQ ID NO: 1, 3, 5, or 7, or the conservatively modified variants thereof. In some embodiments, the nucleotide sequence encodes a protein comprising SEQ ID NO: 2, 4, 6, 8, 9, 10, 11, 12, 13, 14, 15, 16, 17, 18, 19, or 20, or a protein having at least about 50% amino acid identity (preferably at least about 70% amino acid identity, and more preferably at least about 80% amino acid identity) to SEQ ID NO: 2, 4, 6, 8, 9, 10, 11, 12, 13, 14, 15, 16, 17, 18, 19, or 20, and retaining the functional characteristics thereof.

Methods of the invention include culturing plant tissue (e.g., leaf, cotyledon, or hypocotyl explants) on a suitable media (e.g., Murashige and Skoog (MS), supplemented media, etc.) followed by introduction of the exogenous nucleic acid into the tissue using suitable techniques, such as those described above and in the working examples. The exogenous nucleic acid can be introduced using a construct, vector, plasmid or other suitable technique. Expression of the nucleotide sequence results in transformed or modified tissue. Reporter genes and/or selection media can be used to select for and verify transformation. The transformed tissue can then be used to regenerate transgenic whole plants having increased heat stress tolerance. Transgenic plants can be regenerated using various techniques depending upon the plant species involved. In one or more embodiments, regeneration comprises inducing callus formation from the transformed tissue, and regeneration of shoots, followed by rooting of the shoots in soil or other appropriate rooting media to generate the whole plant.

The resulting transgenic plants can be crossed to prepare progeny, and preferably homozygous progeny or seeds. Thus, heat tolerant plants can also be produced indirectly by breeding parent plants having increased tolerance to heat stress with other heat stress-tolerant plants, or even with other cultivars having additional desired characteristics (e.g., pest or herbicide resistance, geographic adaptation, stalk strength, etc.). The resulting progeny can then be screened to identify progeny having increased tolerance to heat stress.

In one or more embodiments, the invention is also concerned with a process of producing (transgenic) seed. In some embodiments, the method comprises self-pollination of a transgenic plant as described herein. In some embodiments, the method comprises crossing a first plant with a second plant, wherein at least one of the first or second plants is a transgenic plant having increased tolerance to heat stress, as described herein. In some embodiments, the first and second plants are both transgenic plants having increased tolerance to heat stress, as described herein. In one or more embodiments, the first and second plants can be crossed via cross-pollination using insects (e.g., flies in cloth cages), manual (hand) pollination, and the like.

Additional advantages of the various embodiments of the invention will be apparent to those skilled in the art upon review of the disclosure herein and the working examples below. It will be appreciated that the various embodiments described herein are not necessarily mutually exclusive unless otherwise indicated herein. For example, a feature described or depicted in one embodiment may also be included in other embodiments, but is not necessarily included. Thus, the present invention encompasses a variety of combinations and/or integrations of the specific embodiments described herein.

Nucleic acids or proteins "comprising" a nucleotide sequence or amino acid sequence means that the entire sequence is present, but may include one or more additional nucleotides or amino acids on the 3' or 5' end of the designated sequence, as long as the sequence retains the functional characteristics of the gene or protein. Nucleic acids or proteins "consisting of" a nucleotide sequence or amino acid sequence means that the entire sequence is present, and no further nucleotides or amino acids are encompassed by the nucleic acid or protein.

A "control" plant, as used in the present invention, refers to a plant used to compare against transgenic or genetically-modified plants according to the invention for the purpose of identifying changes in the transgenic or genetically-modified plant. The control plant is of the same species as the non-naturally occurring plant. In some cases, the control plant may be a wild-type (native) plant, although cultivars and genetically altered plants that otherwise have normal expression of starch synthase and/or heat tolerance can also be used a references for comparison. A "wild type" plant is a plant that has not been genetically modified or treated in an experimental sense. A "wild-type" gene is one that has the characteristics of a gene isolated from a naturally occurring source. A "wild-type" gene product is one that has the characteristics of a gene product isolated from a naturally occurring source, whereas "modified" genes or gene products are those having modifications in sequence and/or functional properties (i.e., altered characteristics) when compared to the wild-type gene or gene product. The term "transgenic" is used herein to refer to a plant, a plant structure, a plant cell, a plant tissue, or a plant seed that contains at least one heterologous gene in one or more of its cells. Likewise, "genetically-modified", "modified," or "transformed," cells, tissues, seeds, plants, etc. are those that have been altered to include a transgene expressing exogenous gene products, as opposed to non-modified cells, tissues, etc. The terms are synonymous with "genetically-engineered."

The term gene "expression" is used herein to refer to the process of converting genetic information encoded in a gene into RNA (e.g., mRNA, rRNA, tRNA, or snRNA) through transcription of the gene (i.e., via the enzymatic action of an RNA polymerase), and into protein, through translation of mRNA. Gene expression can be regulated at many stages in the process. The term "overexpression" refers to the production of a gene product in transgenic plants that exceeds levels of production in normal, control, or non-transgenic plants. References to altered "levels" of expression refers to the production of gene product(s) in modified plants, such as transgenic plants, in amounts or proportions that differ from that of normal, control, or non-modified plants.

The term "operably linked" refers to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced The term "vector" refers to nucleic acid molecules that transfer DNA segment(s) from one cell to another. The term includes recombinant DNA molecules containing a desired coding sequence(s) and appropriate nucleic acid sequences (e.g., promoters) necessary for the expression of the operably linked coding sequence in a particular host organism. It is used interchangeably herein with the term "plasmid." Examples of suitable vectors for used in the invention include pACH20, pJL10P5, pGmubi, pACH17, and the like.

The term "transform" is used herein to refer to the introduction of foreign DNA into cells. Transformation may be accomplished by a variety of means known to the art and described herein.

The term "isolated" when used in relation to a nucleic acids or proteins, refers to sequences that are identified and separated from at least one contaminant nucleotide or amino acid with which it is ordinarily associated in its natural environment. That is, an isolated nucleic acid or protein is one that is present in a form or setting that is different from that in which it is found in nature.

The terms "sequence identity" or "amino acid identity" are used herein to describe the sequence relationships between two or more nucleic acid or amino acid sequences when aligned for maximum correspondence over a specified comparison window. The percentage of "identity" is determined by comparing two optimally aligned sequences over the comparison window. For "optimal alignment" of the two sequences, it will be appreciated that the portion of the sequence in the comparison window may include gaps (e.g., deletions or additions) as compared to the reference sequence, which does not contain additions or deletions. After alignment, the number of matched positions (i.e., positions where the identical nucleic acid base or amino acid residue occurs in both sequences) is determined and then divided by the total number of positions in the comparison window. This result is then multiplied by 100 to calculate the percentage of sequence or amino acid identity. It will be appreciated that a sequence having a certain percentage of sequence identity to a reference sequence does not necessarily have to have the same total number of nucleotides or amino acids (see e.g., microRNAs discussed above). Thus, a sequence having a certain level of "identity" includes sequences that correspond to only a portion (i.e., 5' non-coding regions, 3' non-coding regions, coding regions, etc.) of the reference sequence.

As used herein, the phrase "and/or," when used in a list of two or more items, means that any one of the listed items can be employed by itself or any combination of two or more of the listed items can be employed. For example, if a composition is described as containing or excluding components A, B, and/or C, the composition can contain or exclude A alone; B alone; C alone; A and B in combination; A and C in combination; B and C in combination; or A, B, and C in combination.

The present description also uses numerical ranges to quantify certain parameters relating to various embodiments of the invention. It should be understood that when numerical ranges are provided, such ranges are to be construed as providing literal support for claim limitations that only recite the lower value of the range as well as claim limitations that only recite the upper value of the range. For example, a disclosed numerical range of about 10 to about 100 provides literal support for a claim reciting "greater than about 10" (with no upper bounds) and a claim reciting "less than about 100" (with no lower bounds).

EXAMPLES

The following examples set forth methods in accordance with the invention. It is to be understood, however, that these examples are provided by way of illustration and nothing therein should be taken as a limitation upon the overall scope of the invention.

Introduction

Starch synthase (SS), including soluble starch synthase (SSS), is one of the key enzyme components that shows sensitivity to high temperature during starch deposition and grain growth. In wheat, temperatures above 25° C. reduce soluble starch synthase activity in wheat endosperm. However, there are significant differences in sensitivity to high temperatures among soluble starch synthases of different plant species. For example, rice soluble starch synthase is able to maintain a high enzyme activity at 35° C., resulting in production of long, linear chain amylopectin in the endosperm. Since wheat soluble starch synthase is deactivated at elevated temperature and rice soluble starch synthase withstands high temperature, expression of a rice soluble starch synthase gene in wheat may increase the sink strength and thereby increase the productivity under heat stress. The objective of this study was to investigate the effects of expression of a rice soluble starch synthase gene on starch deposition and the yield of wheat kernel weight under heat stress conditions. The SSI gene cloned in wheat had 81% amino acid similarity with rice SSI and produced a 75 kDa protein, whereas rice SSI produces a 57 kDa protein. The wheat and rice SSI are structurally similar, consisting of 15 exons and 14 introns. The exons of both genes are virtually identical in length, but introns 1, 2, 4 and 10 of wheat SSI are longer and introns 6, 11 and 14 are shorter than that of the corresponding rice introns.

Example 1

Vector Construction and Plant Transformation

1. Vector Construction

Instead of amplifying the Rice Soluble Starch Synthase gene directly from rice mRNA using Genbank accession # NM_001063416 (SEQ ID NO:21), a 1675 bp PCR product was generated from cDNA derived from rice plants (Kitakke) using the primer pair SSS-AF (SEQ ID NO:24) and SSR-BR (SEQ ID NO:25) and cloned into the pCR-Blunt plasmid (SEQ ID NO:26). This 1675 bp PCR Fragment (SEQ ID NO:23) corresponded to the back two-thirds of the rice SSS gene (SEQ ID NO:21). For the 5' end of the rice SSS gene, Plasmid 41637-1 (SEQ ID NO:22) was synthesized by Genscript and contained 440 bp of SEQ ID NO:21, starting at −3 from the start codon and including an additional 23 bp leader sequence 5' for cloning. This leader sequence contained XhoI, BamHI, and PmeI sites.

The two fragments of the SSS gene were ligated together by digesting plasmid 41637-1 to completion with XhoI and HindIII and isolating a 486 bp fragment. The pCRBlunt-1675SSR plasmid was digested with XhoI and partially digested with HindIII. Next, the 486 bp fragment was ligated into the pCR-Blunt plasmid resulting in a complete SSS gene (pCRBlunt-SSS) (SEQ ID NO:27) containing a 1960 bp coding sequence for the SSS protein.

For overexpression in wheat the pCRBlunt-SSS plasmid was digested with BamHI and subcloned into either pAHC17 (containing the maize ubiquitin promoter). For seed specific expression pCRBlunt-SSS was digested with BamHI, end filled with T4 DNA Polymerase and blunt end ligated into the PmeI site between the DY10 promoter and terminator.

Construct pAHC17 was made using cDNA of rice (cv Katake) soluble starch synthase 1 (SSI, 1960 bp) controlled by maize ubiquitin 1 promoter and the nopaline synthase (NOS) terminator is shown in FIG. 1a. Construct pJL10P5 was made using the same cDNA controlled by HMW-Dy10 promoter and the nopaline synthase (NOS) terminator, and is shown in FIG. 1b. A third construct, pAHC20 contained the bar gene controlled by ubiquitin 1 promoter and NOS terminator (FIG. 1c) which confers resistance to the herbicides glufosinate (trade name Liberty; Bayer Crop Sciences, Research Triangle, N.C., USA) and bialaphos.

2. Transformation a. Production of Transgenic Plants Bobwhite wheat (*Triticum aestivum* L. cv. 'Bobwhite') was used for transformation. Immature embryos 2-3 mm in length were collected from 10-14 day old, surface sterilized caryopses, and placed upside down on CM4 media (Murashige & Skoog salts and Gamborg B5 vitamins, supplemented with 40 g/L maltose, 2.2 mg/L picloram, 0.5 gm/L 2,4-D, and 2 g/L Gelrite) for two to seven days in a dark room at 25° C. for callus formation. Three to five days after the transfer, the initiated calli were either pretreated four to eighteen hours on 0.4M Mannitol/Sorbitol CM4 media or air-dried in the laminar hood for 30 minutes prior to transformation. For transformation, plasmid pAHC20 was used in combination with constructs pAHC17 or pJL10P5. Genetic transformation was performed using a particle inflow gun. After particle bombardment, tissues were kept on the CM4 media for two to five days to allow better recovery. Wheat calli were then transferred onto selection media (CM4 media containing 5 mg/L glufosinate ammonium) and maintained for two weeks in the dark. The tissues were transferred to CM4 media containing 10 mg/L glufosinate ammonium in darkness for two cycles of 14 days each. The tissues were then transferred to MSP media (Murashige & Skoog salts, supplemented with 5 nM NH4, 20 mM NO3, Gamborg B5 vitamins, 4% maltose, 0.2 mg/L 2,4-D and 2 g/L Gelrite) containing 10 mg/L glufosinate ammonium in light for shoot production. Tissues developing shoots were transferred to a shoot elongation media, MSE (Murashige & Skoog salts, supplemented with 5 nM NH4, 20 mM NO3, Gamborg B5 vitamins, 4% maltose, and 2 g/L Gelrite) containing 5 mg/L glufosinate ammonium in light for 14 days. When shoots elongated to ~3-6 mm, the whole clumps were transferred to large culture tubes with 13 ml of MSE media containing 10 mg/L glufosinate ammonium. Plants with well-developed roots and shoots were planted into small peat pots for hardening with high humidity. These hardened plants were selected for herbicide resistance using 0.2% (v/v) Liberty solution by painting a marked area of the 3rd leaf, followed by observation at three to five days.

b. PCR Screening of Transgenic Lines

In each generation, PCR was performed using genomic DNA to screen transgenic wheat plants for the rice SSI gene. DNA was isolated from leaf tissue using a modified CTAB method. A leaf tissue sample of 100-150 mg leaf was taken and placed in a 2 mL centrifuge tube and crushed in liquid nitrogen. Next, 800 μL of 2×CTAB extraction buffer containing 4 μL 2-Mercaptoethanol (Sigma, St. Louis, Mo.) was added to the sample. Tubes were incubated in a water bath for 60 minutes at 65° C. followed by 10 minutes cooling at room temperature. Then, 500 μL chloroform: isoamyl alcohol (24:1) was added and the tubes were placed on a rotary shaker for 30 to 60 minutes followed by centrifuging for 20 minutes at 1,200 rpm. Supernatant was transferred to a clean tube and 2 μL RNase was added to remove RNA from DNA. DNA in aqueous phase was precipitated by adding approximately ⅔ volume of isopropanol and placing the tubes at −20° C. overnight. In each generation, PCR screening was conducted using two primer pairs to screen for transgenic plants containing the SSI gene.

For the first PCR target, the forward primer, SEQ ID NO:28, anneals starting 1345 bases downstream from the initiation codon of SSI cDNA, and the reverse primer, SEQ ID NO:29, hybridizes starting 145 bases upstream of the stop codon of SSI cDNA. This primer pair amplifies a 471 bp PCR product from the 3' end of the gene. The PCR program for this primer was 95° C. for 5 minutes, 30 cycles of 95° C. 30 s, 57° C. 30 s, and 72° C. 90 s followed by 72° C. for 10 minutes. For the second PCR target, the forward primer, anneals starting 476 bases downstream of the start codon and the reverse primer (SEQ ID NO:30) anneals starting 815 bases upstream of the stop codon of the gene, and produces a 670 base pair PCR product. PCR conditions were the same as above except the annealing temperature was 60° C. instead of 57° C.

c. Southern Blot Analysis

PCR was conducted using a second primer pair (SEQ ID NOs:32 and 33) and pAHC17 plasmid DNA as the template. The PCR product was purified using QIAGEN gel purification kit, and labeled with dCTP ($\alpha$-$^{32}$P) using Megapriming DNA labeling system (Amersham, UK). The labeled PCR product was used as a probe in Southern blot analysis. Next, 25 μg genomic DNA from $T_2$ plant leaves were digested with BamH1 and EcoR1 enzymes. Digested DNA were separated on 0.8% agarose gels, and transferred to a nylon hybridization membrane and hybridized with 32p-labelled PCR product of rice SSI gene.

d. Reverse Transcriptase (RT) PCR

RNA was isolated from both leaf and 20-day-old developing seeds of $T_2$ plants. For the leaf sample, QIAGEN RNA isolation kit was used, while isolation from the seed was done by using a Guanidine Thiocyanate solution. Wheat (*Triticum aestivum* L.) seeds (50-100 mg) were collected and ground to a fine powder in liquid nitrogen with pre-chilled mortar and pestle. The flour sample was then transferred into a pre-chilled 1.5 ml RNase free microcentrifuge tube. A 400-μl extraction buffer I (100 mM TRIS (pH 8.0), 150 mM LiCl, 50 mM EDTA, 1.5% SDS and 1.5% 2-mercaptoethanol) aliquot was immediately added to the seed powder. After mixing the content by vigorously vortexing, 250 μl mixture of phenol:chloroform (1:1, pH 4.7) was added, and the samples were mixed well by inversion. Samples were then centrifuged immediately at 13,000 g for 15 min at 4° C. The upper aqueous phase was carefully transferred to a new 1.5 ml tube containing 250 μl of extraction buffer II (4.2M Guanidine thiocyanate, 25 mM Sodium citrate, 0.5% Laurylsacosine and 1 M Sodium acetate (pH 4.0)). Samples were mixed by gentle inversion and incubated at room temperature for 10 min. After the incubation, 200 μl of chloroform: isoamyl alcohol (24:1) was added and the samples were then centrifuged at 13,000 g for 15 min at 4° C. To the recovered supernatant, 300 μl iso-propanol and 250 μl 1.2 M sodium chloride were added. The samples were then mixed by inversion and put on ice for 15 min. The sample was centrifuged at 13,000 g for 15 min at 4° C., then the supernatants were discarded and the RNA pellets were washed carefully with 400 μl 70% ethanol. The RNA pellets were then dried for 15 to 20 min at room temperature in a laminar flow hood and were re-suspended in the appropriate volume of RNase free water (e.g. 50 μl), and stored at −70° C. RNA was reverse-transcribed to cDNA using a reverse transcription system kit from Promega. PCR was conducted with the first primer pair described above (gene specific primer) and found the amplification in 1% agarose gel. DNA contamination in RNA was checked by performing PCR using a house keeping gene called Tubulin (SEQ ID NOs:34 and 35). PCR conditions were the same as the first primer pair except the annealing temperature was 58° C. instead of 57° C.

e. Western Blot Analysis

Total soluble proteins of flag leaves and seeds were extracted from each $T_2$ transgenic wheat event, one non-transgenic wheat variety (BW), and one rice variety (Nipponbare) at 20 days after anthesis. Total proteins were extracted from both leaf and seed samples by grinding and homogenizing samples in protein extraction buffer. Protein concentrations were estimated using Quick Start Bradford Protein Assay kit (Bio Rad). Samples were diluted in the buffer to maintain equal concentration for equal loading. Equal loading was also maintained by checking stained gels. Proteins were separated by loading 40 μg of each sample on a 10% SDS polyacrylamide gel for separation. SDS-PAGE-separated proteins were transferred to polyvinylidene deflouride (PDVF) membranes for immunoblotting. PDVF membranes with the transferred proteins were probed for rice soluble starch synthase1 (SSI) protein using rabbit polyclonal anti-SSI antibodies raised by AnaSpec, Inc. (California, USA) and goat anti-rabbit secondary antibodies conjugated to horseradish peroxidase (Santa Cruz Biotechnology, Inc, California, USA). Equal amount of total protein (40 μg) was loaded in each lane.

Example 2

Heat Stress Treatment and Phenotyping

Experiments were conducted for phenotyping under heat stress and optimum temperature conditions using eight to twenty pots for each event/line in each experiment. In the first experiment (Exp 1), $T_2$ plants from a ubiquitin promoter event (Ub-1), a Dy10 promoter event (Dy10), and non-transgenic Bobwhite produced from tissue culture (BWTC) were grown in the greenhouse. Following germination, seedlings were PCR screened for the presence of SSI gene in the laboratory and single seedlings were transplanted to pots (14 cm height, 50 cm top perimeter and 36 cm bottom perimeter) filled with Metro Mix 200 potting soil (Hummert Intl. Topeka, Kans.). The greenhouse was set at day/night temperature of 22/15° C. with 16 hours of light and 8 hours of dark for normal growth. Plants were watered daily. One or two tillers per plant were tagged at anthesis, and half the plants from each event/line were transferred to a high-temperature growth chamber at 10 days after anthesis, as determined using tagged tiller/s. Growth chambers were set at 31/24° C. (day/night) with 16/8 h (light/dark) and 70-80% humidity. The remaining plants were transferred to another growth chamber having optimum day/night temperature (22/15° C.) with the same other conditions as the high temperature chamber. Thousand kernel weights (TKW) were obtained from the tagged tillers by drying to equivalent moisture content, weighing the seeds, and converting to TKW using the seed number of that tagged head. Effective tillers number was also counted during harvest. Chlorophyll content was measured from flag leaves, started at 12 days after anthesis then every other day for twelve days. Days required for physiological maturity were calculated from date of anthesis to date of physiological maturity. Non-transgenic and transgenic event means were compared using two sample t-tests with unequal sample variance at $\alpha$=0.05.

In the second experiment (Exp 2), $T_2$ plants from two ubiquitin promoter events Ub-1, Ub-2, a Dy10 promoter event (Dy10), BWTC, and Bobwhite from non-tissue culture (BWNTC) were grown in the greenhouse following the procedure in Exp. 1. Heat stress was given in a growth chamber set at 33/26° C. maintaining all other conditions similar to Exp. 1. Control plants were grown in the greenhouse at optimum temperature (22/15° C.) with 16/8 h (light/dark) and 70-80% humidity. Exp. 2 was done following the procedure for Exp. 1 except that chlorophyll content data were not taken.

In the third experiment (Exp. 3), $T_3$ plants from 2 ubiquitin promoter event Ub-1, Ub-2, a Dy10 promoter event (Dy10), BWTC, and BWNTC were grown in the greenhouse. Phenotyping both under heat stress (34/28° C.) and optimum temperature (22/15° C.) was done in growth chambers following the procedure in Exp 1.

In a final experiment (Exp. 4), $T_4$ plants from the three transgenic events along with non-transgenic Bobwhite (BWNTC) were grown in the greenhouse and transferred into the growth chamber for phenotyping under both high and optimum temperature condition following the procedure in Exp. 1. In this experiment, growth chambers were maintained at 32-33/30° C. for heat stress and 20/15° C. for optimum temperature condition. Data were taken only on thousand seed weight and seed number per head.

Temperature fluctuation of ±1.5° C. was found for highest temperature in growth chamber from the set point, while fluctuation varied (±2 to 4) in the green house depending on the outside air temperature.

Results and Discussion

1. Transgenic Plant Production, Transgene Stable Insertion, Inheritance and Copy Number Estimation A total of six bar-positive transgenic wheat lines were developed using co-transformation with pAHC17/pAHC20 and p7L10P5/pAHC20. Five of six lines contained the modified rice SSI gene as determined by PCR analysis from leaf DNA in the $T_0$ generation.

TABLE 1

Presence of rice soluble starch synthase in six Liberty positive wheat events and their $X^2$ value.

| Event # | Promoter | PCR test in $T_0$ | # of PCR positive $T_1$ plants | # of PCR negative $T_1$ plants | $X^2$ value (based on 3:1 ratio) |
|---|---|---|---|---|---|
| 1286 (Ub1) | Ubiquitin | + | 37 | 6 | 2.79 |
| 1588 | Ubiquitin | + | 4 | 2 | 1.33 |
| 1700 (Ub2) | Ubiquitin | + | 7 | 2 | 0.037 |
| 2036 | DY10 | + | 46 | 20 | 0.99 |
| 2173 (Dy10) | DY10 | + | 13 | 5 | 0.074 |
| 2540 | DY10 | − | 0 | 10 | — |

Ultimately, two previously SSI-positive lines tested as PCR negative. The remaining three SSI-positive lines were used for further analysis. Two lines contained the ubiquitin promoter, and one contained the Dy10 promoter.

Figure 2:
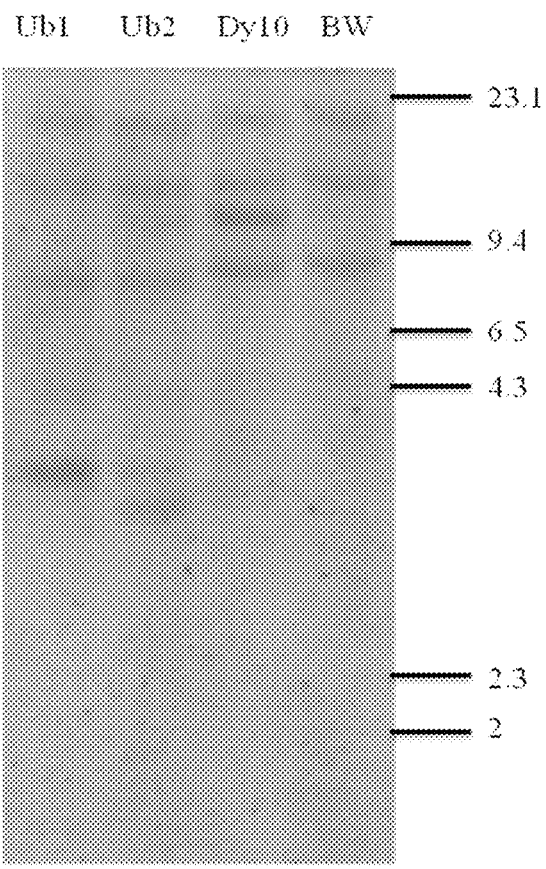
FIG. 2 is an image of Southern blot analysis of three $T_2$ generation transgenic wheat events and a non-transgenic Bobwhite (BW) control, where Ub1: Event #1286 with ubiquitin promoter; Ub2: Event #1700 with ubiquitin promoter; Dy10: Event #2173 with Dy10 promoter; and BW: non-transgenic Bobwhite variety.

Analysis of SSI gene segregation using $X^2$-test in $T_1$ plants showed that the SSI gene segregated in a 3:1 ratio for the Ub1, Ub2 and Dy10 events, indicating insertion of at least one copy of the SSI. Southern analysis using genomic DNA from $T_2$ leaves and the SSI gene sequence as a probe demonstrated that all three transgenic events and the non-transgenic BW had three bands in common (FIG. 2), indicating that probe hybridized with wheat endogenous SSI gene sequences and, due to its hexaploid nature, the wheat genome harbors three homologous SSI genes (copies). Each lane of the transgenic events also showed additional unique bands (FIG. 2), confirming transgene integration. Based on the uncommon band numbers, Ub1 and Dy10 transgenic events appeared to harbor only a single SSI gene insertion (single copy), while, Ub2 seems to harbor three copies of the rice gene. These results demonstrated the stable insertion of the rice gene into the wheat genome that followed the expected pattern of inheritance.

2. Transgene Expression

Figure 3:
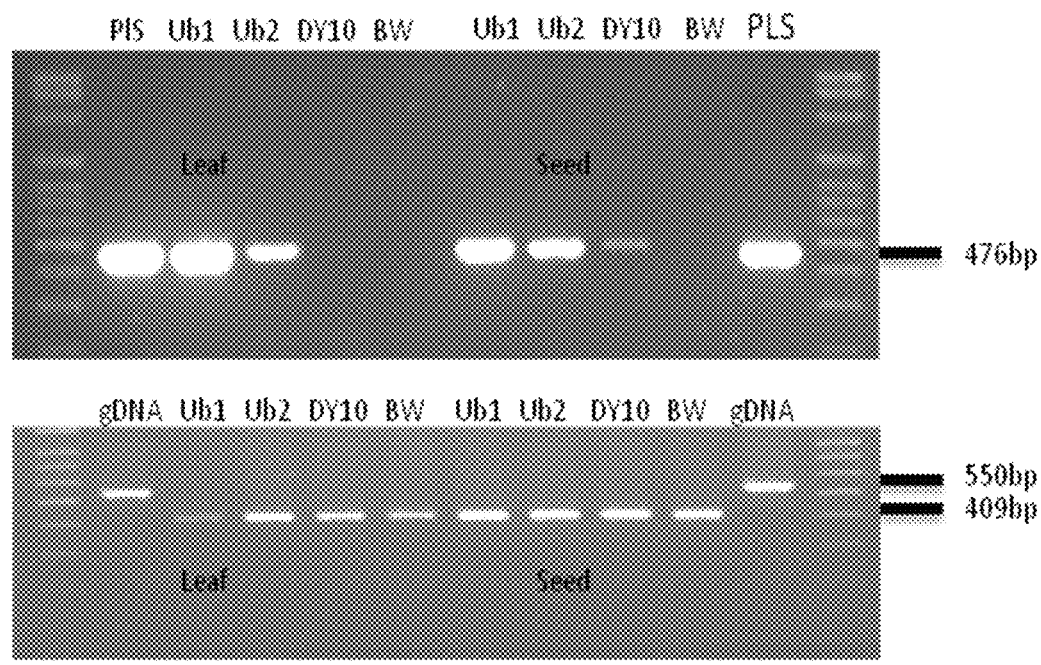
FIG. 3 is an image of: (a) Reverse transcriptase (RT)-PCR for leaf samples (left) and seed samples (right), where Pls: Plasmid DNA having SSI gene; Ub1: Event #1286 with ubiquitin promoter; Ub2: Event #1700 with ubiquitin promoter; Dy10: Event #2173 with Dy10 promoter; and BW: non-transgenic Bobwhite variety; and (b) RT-PCR using Tubulin gene primer for leaf samples (left) and seed sample (right), where gDNA: genomic DNA of BW.

Reverse Transcriptase (RT) PCR was conducted using the RNA isolated from both leaf and seed samples of three PCR positive transgenic lines and non-transgenic Bobwhite. The leaf samples from the two ubiquitin promoter events (Ub1 and Ub2) produced a band matching the expected size from the rice SSI gene (FIG. 3a). The Dy10 promoter event and the non-transgenic BW did not show any bands (FIG. 3a), indicating that, as expected, the Dy10 promoter is seed specific. The seeds of non-transgenic BW did not show the rice SSI band, while the seeds of all three independent events showed a clear rice SSI band, indicating that both ubiquitin and Dy10 promoters were active in the seeds of the transgenic plants. Single tubulin bands with different sizes between genomic DNA samples and RNA samples demonstrated that RNA samples were not contaminated with DNA (FIG. 3b). Genomic DNA makes a 550 bp band and cDNA makes a 409 bp band with that primer.

Figure 4:
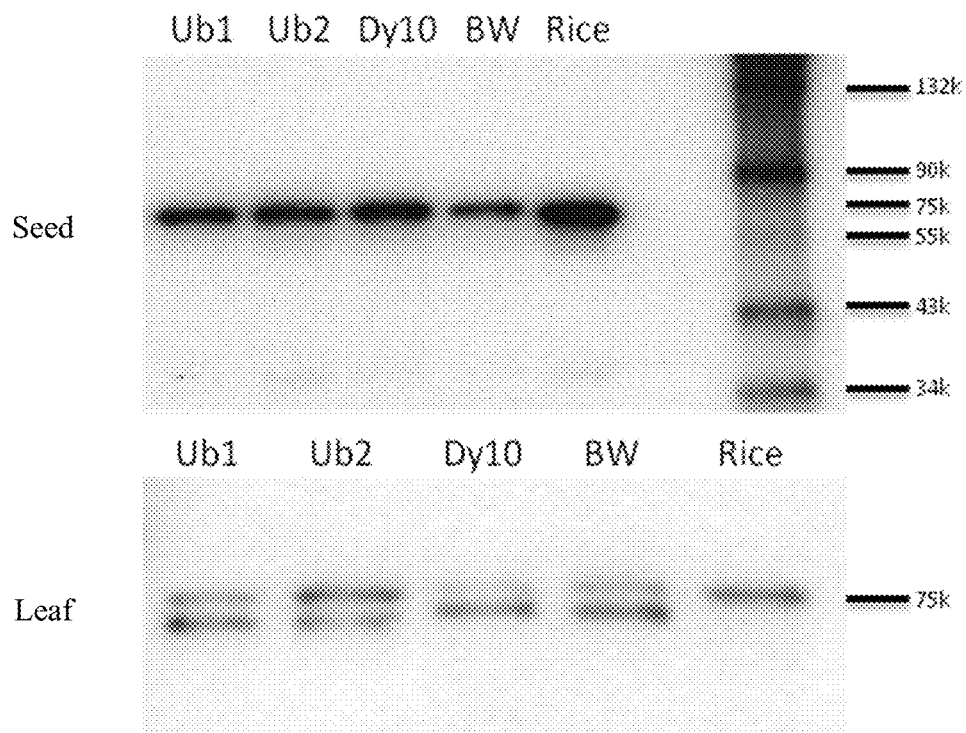
FIG. 4 shows an image of Western blot analysis using seed and leaf samples from three $T_2$ generation transgenic wheat events, one non-transgenic Bobwhite (BW), and one rice sample.

Western blots were used to detect the presence of SSI proteins in wheat. A rice leaf sample was also included. The antibody developed from rice SSI protein sequence recognized SSI proteins in both rice and wheat. In seeds, only one SSI protein band was detected in the three transgenic events, non-transgenic BW and rice. The SSI proteins showed the same molecular weight (75 kD) in both wheat and rice (FIG. 4). However, the SSI band intensities were much stronger in the transgenic wheat events than in non-transgenic wheat, indicating that the rice SSI protein was produced in the seeds of the three transgenic wheat events. In seed samples, all transgenic events along with rice showed stronger signal than non-transgenic wheat. The antibody binds with both wheat endogenous SSI and rice SSI protein.

In leaves, two SSI protein bands (isoforms 60 KD and 75 KD) were detected in three transgenic events and non-transgenic BW. The 75 KD SSI isoform showed stronger band intensity in the Ub2 event than the Ub1 event, Dy10 and non-transgenic BW. Only the 75 KD isoform was detected in rice (FIG. 4).

3. Yield Related Traits Analysis of Transgenic Events Under Heat Stress

Based on PCR, RT-PCR, Southern blot analysis and Western blot analysis, three events (Ub1, Ub2 and Dy10) were found positive for transgene (SSI). PCR negative plants from different lines (BWTC) and Bobwhite plants not derived from tissue culture (BWNTC) were compared with different SSI positive lines.

Ub2 was not included in the first experiment and only BWTC plants were considered as control. Significant differences were found for TKW for Ub1 (3.22%) and Dy10 (6.71%) events compared to BWTC, as shown in the data in the tables below.

TABLE 2

TKW and seed number/selected head in transgenic and non-transgenic wheat in T2 generation (Exp 1) using soluble starch synthase gene (SS1) of rice.

| Temp. | Event name | TKW (g) | | | Seed number/selected head | | |
|---|---|---|---|---|---|---|---|
| | | Mean "+" | STD | T stat | Mean "+" | STD | T stat |
| 31/24° C. | BWTC(6) | 29.5 | 1.21 | | 54.33 | 11.58 | |
| | Ub1 (10) | 30.45 | 1.32 | 1.85* | 54.2 | 14.24 | 0.02 |
| | Dy10 (4) | 31.48 | 0.83 | 3.47** | 41.25 | 4.03 | 2.54* |
| 22/15° C. | BWTC (3) | 35.62 | 1.5 | | 59.33 | 11.5 | |
| | Ub1 (9) | 37.71 | 1.96 | 1.92 | 58.55 | 11.1 | 0.1 |
| | Dy10(4) | 37.53 | 2.89 | 1.13 | 45.75 | 12.44 | 1.49 |

† Number of plants studied in this experiment is accompanied by event name in parenthesis.
BWTC - non-transgenic Bobwhite but established through tissue culture, Ub1 - event 1286 having ubiquitin promoter, Dy10 - Event 2173 having Dy10 promoter.
* and ** denote P < 0.05 and 0.01 confidence levels, respectively.

TABLE 3

Percent change in TKW compared to control for the three experiments

| Event | 1st Exp. (31/24° C.) | 1st Exp. (22/15° C.) | 2nd Exp. (33/26° C.) | 2nd Exp. (22/15° C.) | 3rd Exp. (34/28° C.) | 3rd Exp. (22/15° C.) |
|---|---|---|---|---|---|---|
| Ub1 | 3.22* | 5.87 | 7.66* | 3.12 | 21.20* | 8.43 |
| Ub2 | Absent | Absent | 10.83 | −1.40 | 24.59** | 7.44* |
| Ub | 3.22* | 5.87 | 9.25* | 0.88 | 22.94** | 7.96* |
| Dy10 | 6.71* | 5.36 | 25.67*** | −0.75 | 34.59** | 11.19 |

*, , and *, denote $P < 0.05$, 0.01 and 0.001 respectively found in the comparison.
The Ub observation combines the Ub1 and Ub2 observation.

As shown in Table 4, effective tiller number per plant and days required for physiological maturity showed no significant difference, but as can be seen from Table 2 above, seed number per selected head was significantly lower for the Dy10 event. There was no significant difference between transgenic and non-transgenic events for any studied trait (Tables 2 and 4) under optimum temperature conditions.

TABLE 4

Tiller number/plant and days required for anthesis to PM in transgenic and non-transgenic wheat in T2 generation (Exp 1) using soluble starch synthase gene (SS1) of rice

| Temp | Event name | Tiller number/plant Mean | STD | T stat | Days required for PM Mean | STD | T stat |
|---|---|---|---|---|---|---|---|
| 31/24° C. | BWTC(6) | 5.33 | 1.03 | | 27.33 | 1.03 | |
| | UbI (10) | 5.7 | 0.82 | 0.74 | 27.4 | 0.97 | 0.13 |
| | Dy10 (4) | 5.75 | 0.5 | 0.85 | 27.5 | 1.29 | 0.22 |
| 22/15° C. | BWTC (3) | 6 | 1.0 | | 37.33 | 0.57 | |
| | Ub1 (9) | 6.22 | 0.96 | 0.34 | 37.11 | 0.78 | 0.53 |
| | Dy10(4) | 6.25 | 2.22 | 0.2 | 36.75 | 0.5 | 1.4 |

† Number of plants studied in this experiment is accompanied by event name in parenthesis.
BWTC - non-transgenic Bobwhite but established through tissue culture, Ub 1 - event 1286 having ubiquitin promoter, Dy10 - Event 2173 having Dy10 promoter.

$T_2$ plants were used for experiment 2 (Exp. 2) and higher temperatures were used for the heat stress treatment. All three transgenic events were compared with non-transgenic Bobwhite plants. No significant differences between PCR negative Bobwhite (BWTC) and normal Bobwhite (BWNTC) were found for the traits under consideration. Both the tissue culture-derived and non-tissue culture-derived plants were pooled as controls. Transgenic events with ubiquitin (10.70%) and Dy10 (25.67%) promoter showed significant increases in TKW compared to non-transgenic (BW) plants, as shown in Table 3 above, and Table 5 below. As shown in Table 5, individually all events having the transgene had higher TKW than non-transgenic lines.

TABLE 5

TKW comparison between transgenic and non-transgenic wheat in $T_2$ and $T_3$ generation (Exp. 2 and 3) using rice soluble starch synthase gene (SSI).

| Temp | Event name | 2nd experiment (high temp 33/26° C.) Mean"+" | Mean"−" | STD | T stat | 3rd Experiment (high temp 34/28° C.) Mean"+" | Mean"−" | STD | T stat |
|---|---|---|---|---|---|---|---|---|---|
| High | BWTC | | 22.87 (5) | 1.94 | 0.301 | | 20.23 (5) | 2.65 | 0.134 |
| | BWNTC | | 22.51 (4) | 1.67 | | | 19.94 (5) | 3.89 | |
| | BW | | 22.71 (9) | 1.73 | — | | 20.09 (10) | 3.14 | — |
| | Ub1 | 24.45 (4) | | 1.44 | 1.89* | 24.35 (5) | | 4.31 | 1.96* |
| | Ub2 | 25.17 (4) | | 2.35 | 1.88 | 25.03 (6) | | 2.46 | 3.50** |
| | Ub | 24.81 (8) | | 1.84 | 2.41* | 24.70 (11) | | 3.24 | 3.30** |
| | Dy10 | 28.54 (6) | | 1.85 | 6.14*** | 27.04 (4) | | 3.12 | 3.75** |
| Optimum 22/15° C. | BWTC | | 40.95 (5) | 2.27 | 0.144 | | 40.91 (5) | 2.68 | 0.932 |
| | BWNTC | | 40.69 (4) | 3 | | | 39.45 (5) | 2.25 | |
| | BW | | 40.84 (9) | 2.41 | — | | 40.18 (10) | 2.46 | — |
| | Ub1 | 42.11 (4) | | 3.37 | 0.68 | 43.57 (6) | | 4.28 | 1.77 |
| | Ub2 | 40.27 (4) | | 1.36 | 1.81 | 43.17 (6) | | 2.16 | 2.55* |
| | Ub | 41.20 (8) | | 2.57 | 0.292 | 43.38 (12) | | 3.25 | 2.63** |
| | Dy10 | 40.53 (5) | | 1.76 | 0.276 | 44.68 (4) | | 4.54 | 1.87 |

† Number of plants studied in this experiment is accompanied by mean in parenthesis.
Mean"+" - positive transgenic plants and Mean"−" are the non-transgenic plants.
BWTC - non-transgenic Bobwhite but established through tissue culture, BWNTC, non-transgenic Bobwhite plants not regenerated through tissue culture. Ub1 - event 1286 having ubiquitin promoter, Ub2 - event 1700 having ubiquitin promoter, The Ub observation combines the Ub1 and Ub2 observation.
Dy10 - Event 2173 having Dy10 promoter, STD - Standard deviation
*, , and *, denote $P < 0.05$, 0.01 and 0.001 respectively.

TABLE 6

Comparison of seed numbers per selected head between transgenic and non-transgenic wheat in T₂ and T₃ generation (Exp. 2 and 3 respectively) using rice soluble starch synthase gene (SSI).

| Temp | Event name | 2$^{nd}$ experiment (high temp 33/26° C.) | | | | 3$^{rd}$ Experiment (high temp 34/28° C.) | | | |
|---|---|---|---|---|---|---|---|---|---|
| | | Mean"+" | Mean"−" | STD | T stat | Mean"+" | Mean"−" | STD | T stat |
| High | BWTC | | 47.4 | 4.56 | 0.475 | | 46.6 | 11.74 | 0.32 |
| | BWNTC | | 46 | 4.24 | | | 48.8 | 9.73 | |
| | BW | | 46.78 | 4.20 | — | | 47.7 | 10.23 | — |
| | Ub1 | 46 | | 4.08 | 0.314 | 50.4 | | 12.80 | 0.41 |
| | Ub2 | 49.5 | | 13.47 | 0.395 | 48.33 | | 4.13 | 0.173 |
| | Ub | 47.75 | | 9.41 | 0.269 | 49.27 | | 8.67 | 0.378 |
| | Dy10 | 36.83 | | 9.22 | 2.476* | 25.25 | | 5.85 | 5.14** |
| Optimum 22/15° C. | BWTC | | 39 | 8.18 | 0 | | 50.2 | 11.26 | 0.989 |
| | BWNTC | | 39 | 10.61 | | | 56.4 | 8.35 | |
| | BW | | 39 | 8.70 | — | | 53.3 | 9.9 | — |
| | Ub1 | 37.5 | | 9.15 | 0.276 | 53.83 | | 10.06 | 0.103 |
| | Ub2 | 49.5 | | 11.15 | 1.67 | 53.84 | | 9.54 | 0.106 |
| | Ub | 43.5 | | 20.06 | 0.587 | 53.83 | | 9.35 | 0.129 |
| | Dy10 | 30 | | 7.11 | 1.96* | 36.75 | | 16.52 | 1.87 |

-Mean"+" - positive transgenic plants and Mean"−" are the non-transgenic plants.
BWTC - non-transgenic Bobwhite but established through tissue culture, BWNTC - non-transgenic Bobwhite not regenerated in tissue culture, Ub1 - event 1286, having ubiquitin promoter, Ub2 - event 1700, having ubiquitin promoter, The Ub observation combines the Ub1 and Ub2 observation.
Dy10 - Event 2173 having Dy10 promoter, STD - Standard deviation
* and ** denote P < 0.05 and 0.01 confidence levels, respectively.

As can be seen, Dy10 event produced significantly lower number of seeds than non-transgenic control (BW) in both heat stress (33/26° C.) and optimum temperature (25/15° C.) conditions. Under optimum temperature conditions, TKW, tiller number and days required for physiological maturity were not significantly different.

TABLE 7

Comparison of days required for physiological maturity between transgenic and non-transgenic wheat in T₂ and T₃ generation (Exp. 2 and 3 respectively) using rice soluble starch synthase gene (SSI).

| Temp. | Event name | 2$^{nd}$ experiment (high temp 33/26° C.) | | | | 3$^{rd}$ Experiment (high temp 34/28° C.) | | | |
|---|---|---|---|---|---|---|---|---|---|
| | | Mean"+" | Mean"−" | STD | T stat | Mean"+" | Mean"−" | STD | T stat |
| High | BWTC | | 26.8 | 3.27 | 0.25 | | 22.8 | 1.30 | 0.63 |
| | BWNTC | | 27.25 | 2.22 | | | 22.4 | 0.54 | |
| | BW | | 27 | 2.69 | | | 22.6 | 0.97 | |
| | Ub1 | 29 | | 3.92 | 0.93 | 23.4 | | 0.89 | 1.59 |
| | Ub2 | 28 | | 2.45 | 0.66 | 23.66 | | 0.82 | 2.36* |
| | Ub | 28.5 | | 3.07 | 1.06 | 23.54 | | 0.82 | 2.41* |
| | Dy10 | 29.66 | | 2.50 | 1.96* | 24.25 | | 0.96 | 2.90* |
| Optimum 22/15° C. | BWTC | | 40.8 | 1.79 | 1.31 | | 38.8 | 1.30 | 0 |
| | BWNTC | | 43 | 2.94 | | | 38.8 | 4.82 | |
| | BW | | 41.78 | 2.49 | | | 38.8 | 3.33 | — |
| | Ub1 | 42 | | 3.46 | 0.115 | 36.5 | | 4.42 | 1.10 |
| | Ub2 | 41 | | 3.37 | 0.414 | 37.17 | | 5.19 | 0.69 |
| | Ub | 41.5 | | 3.21 | 0.20 | 36.83 | | 4.61 | 1.16 |
| | Dy10 | 41.2 | | 1.64 | 0.52 | 40.25 | | 4.03 | 0.64 |

Mean"+" - positive transgenic plants and Mean"−" are the non-transgenic plants.
BWTC - non-transgenic Bobwhite but established through tissue culture, BWNTC - non-transgenic Bobwhite not regenerated in tissue culture, Ub1 - event 1286 having ubiquitin promoter, Ub2 - event 1700 having ubiquitin promoter, The Ub observation combines the Ub1 and Ub2 observation.
Dy10 - Event 2173 having Dy10 promoter, STD - Standard deviation
*denotes P < 0.05 confidence level.

As can be seen, under heat stress the Dy10 event took significantly longer to reach physiological maturity (2.66 days) than non-transgenic events.

Exp. 3 was done using T₃ plants and the stress treatment was imposed using higher temperature (34/28° C.) than Exp 2. Transgenic events with both ubiquitin (22.94%) and Dy10 (34.59%) promoters produced seeds having significantly higher TKW than non-transgenic events under heat stress (Tables 3 and 5). The Dy10 event produced significantly lower number of seeds per selected head, while events having ubiquitin promoter showed no difference compared to non-transgenic events (Table 6).

TABLE 8

Comparison of Tiller number/plant between transgenic and non-transgenic wheat in $T_2$ and $T_3$ generation (Exp. 2 and 3 respectively) using rice soluble starch synthase gene (SSI).

| Temp | Event name | 2nd experiment (high temp 33/26° C.) | | | | 3rd Experiment (high temp 34/28° C.) | | | |
|---|---|---|---|---|---|---|---|---|---|
| | | Mean"+" | Mean"−" | STD | T stat | Mean"+" | Mean"−" | STD | T stat |
| High | BWTC | | 5.6 | 1.14 | 0.15 | | 7 | 0.71 | 0.69 |
| | BWNTC | | 5.75 | 1.71 | | | 6.4 | 1.82 | |
| | BW | | 5.67 | 1.32 | | | 6.7 | 1.34 | |
| | Ub1 | 5.75 | | 0.96 | 0.128 | 6.17 | | 1.83 | 0.62 |
| | Ub2 | 5.5 | | 1 | 0.25 | 6.5 | | 2.16 | 0.20 |
| | Ub | 5.63 | | 0.92 | 0.076 | 6.33 | | 1.92 | 0.53 |
| | Dy10 | 5.8 | | 1.30 | 0.182 | 7 | | 1.58 | 0.36 |
| Optimum | BWTC | | 6 | 1 | 0.381 | | 6.8 | 1.79 | 0.63 |
| 22/15° C. | BWNTC | | 6.25 | 0.95 | | | 7.4 | 1.14 | |
| | BW | | 6.11 | 0.93 | — | | 7.1 | 1.45 | — |
| | Ub1 | | 6.5 | 1.29 | 0.54 | 6.83 | | 1.17 | 0.40 |
| | Ub2 | | 6.25 | 0.96 | 0.243 | 7 | | 0.89 | 0.17 |
| | Ub | | 6.38 | 1.06 | 0.542 | 6.91 | | 1.0 | 0.34 |
| | Dy10 | | 6.2 | 1.30 | 0.134 | 7.4 | | 2.07 | 0.29 |

Mean"+" - positive transgenic plants and Mean"−" are the non-transgenic plants.
BWTC - non-transgenic Bobwhite but established through tissue culture, BWNTC - non-transgenic Bobwhite not regenerated in tissue culture, Ub1 - event 1286, having ubiquitin promoter, Ub2 - event 1700, having ubiquitin promoter, The Ub observation combines the Ub1 and Ub2 observation.
Dy10 - Event 2173 having Dy10 promoter, STD - Standard deviation As can be seen, tiller number per plant was not significantly different between transgenic and non-transgenic events. Days required for physiological maturity differed significantly between transgenic and non-transgenic events, with transgenic events averaging 1.28 additional day of grain filling duration than non-transgenic plants (Table 7).

Some differences in TKW were found under optimum temperatures (22/15° C.), in Exp. 1 and 3, but not in Exp. 2. In Exp. 3, Ub2 had significantly higher individual seed weight than non-transgenic BW. No significant variation was found for chlorophyll content in Exp. 1 and 3, under either heat stress or optimum temperature conditions (data not shown).

Using $T_4$ transgenic plants, the fourth experiment was done using higher night time temperature and lower daytime temperature (32-33) than Exp. 3 for heat stress.

head in any temperature condition. Towards the end of the experiment for optimum temperature condition, a malfunction of the growth chamber produced extreme high temperature. As a result, we have disregarded the results of thousand kernel weight under optimum temperature condition.

4. Discussion

Previous work has demonstrated that the SSI gene is responsible for the elongation of shorter A and B1 chains during starch biosynthesis in the soluble phase of the amyloplast. As a result, the mutation of the SSI gene or destruction of that enzyme may have a severe impact on crystalline amylopectin matrix formation, as well as grain filling. Here we tested the hypothesis by using the high temperature (35° C.) tolerance of the rice SSI gene to increase the grain filling potential of wheat under moderately high temperature. In this experiment we introduced the rice SSI gene into a spring

TABLE 9

Mean thousand kernel weight (TKW), percent change in TKW compared to BW control and mean seed number in Exp. 4

| Experiment | Event | Thousand seed weight | | | % 1000 seed | Seed number | | |
|---|---|---|---|---|---|---|---|---|
| | | Mean | Std | T-stat | wt increment | Mean | Std | |
| Heat stress | BW | 23.55 | 4.88 | | | 47.17 | 8.7 | |
| (32-33/30° C.) | UB1 | 26.75 | 2.55 | 1.39* | 13.58 | 52.6 | 1.95 | 1.48 |
| | UB2 | 26.39 | 3.89 | 1.11 | 12.06 | 51.17 | 6.55 | 0.90 |
| | DY10 | 30.50 | 3.38 | 2.94** | 29.51 | 46.57 | 3.78 | 0.16 |
| Optimum temp | BW | 34.27 | 2.1 | | | 47 | 12 | |
| (20/15° C.) | UB1 | 34.72 | 1.0 | 0.43 | 1.31 | 50.4 | 10.41 | 0.47 |
| | UB2 | 35.21 | 0.78 | 0.95 | 2.74 | 49.83 | 9.26 | 0.43 |
| | DY10 | 37.59 | 1.21 | 2.97 | 9.67 | 49 | 10.1 | 0.27 |

* and ** denote P < 0.05 and 0.01 confidence levels, respectively.

Like the previous experiments, Ub1 (13.58%), Ub2 (12.06%), and Dy10 (29.51%) showed considerable increment in thousand kernel weight than non-transgenic control under high temperature. There was high variability in kernel weight within the events; as a result, even though there was a remarkable increment in Ub1 and Ub2, they were not significantly different at 5% level. None of the transgenic events showed significant variation for seed number per wheat variety (BW) using two different promoters, which was confirmed by PCR and genomic DNA blotting in the $T_2$ generation (FIG. 3a). Molecular analysis (Southern blot) revealed three copies of the endogenous SSI gene in wheat, because the non-transgenic Bobwhite, along with all the transgenic events, produced three common hybridization bands with the probe for the rice SSI gene (FIG. 3a). This indicates the high level similarity of rice SSI and wheat endogenous SSI. In addition blast analysis of the rice SSI cDNA sequence (Blast 2 sequence program) reveals 88% nucleotide identity and 81% amino acid identity with the wheat SSI gene. The failure of the event with the DY10 promoter to produce a band using cDNA from the leaf sample (FIG. 3b) in Reverse Transcriptase (RT) PCR proved the promoter specific expression of the transgene. In western blot analysis, separation of wheat SSI from Rice SSI was not possible because of the size similarity of the two proteins. Previous work has reported that the rice SSI protein produced a 57 KD protein band, but in our western gel, it produced a nearly 75 KD band which is similar to the 75 KD wheat SSI band. Using the cDNA sequence of rice SSI we found the expected size of the protein as 75.7 KD, which is supportive of our finding. Two protein bands in the leaf protein support the expression of two isoforms of SSI in wheat leaf tissue, but only one isoform in seeds.

Here, we tested the hypothesis that the rice SSI gene with increased activity under heat will supplement the wheat SSI under high temperature stress and increase the individual grain weight by sustaining starch biosynthesis.

Three transgenic lines expressing the rice SSI gene produced significantly heavier seeds compared to non-transgenic lines under three different experiments at high temperature. Some transgenic events produced slightly heavier seed under optimum temperature in some experiments. This may be due to fluctuation of the highest temperature of the growth chambers. We observed actual temperature were somewhat elevated relative to the set temperature, which might have influenced the SSI activity. There was no variation among transgenic and non-transgenic event in optimum temperature conditions in Exp. 2 which was conducted in the greenhouse during winter. The actual temperature never exceeded the set point in this experiment. It may be possible the wheat SSI activity starts declining at around 25° C. or an even lower temperature. It was clear that the TKW differential between the transgenic and non-transgenic lines increased (Table 3) as the heat stress was increased from Exp. 1 to Exp. 2 to Exp. 3. This result also supports the hypothesis that increasing temperature decreases wheat SSI activity more than rice SSI and also supports previous research regarding the importance of SSI activity related to grain filling.

No significant variation in chlorophyll content (Data not shown) was observed between transgenic and non-transgenic events indicating that differences of starch deposition were not due to the differences in photosynthetic capacity. This result is in line with earlier work that reported that reduced grain filling during high temperature was not due to the supply of the assimilate from photosynthesis.

No variation in tiller number (Tables 4 and 8) and height of the plants (visual measurement) indicates that the transgene did not compromise the morphology of the plants. Significantly lower seeds per spike were found with the transgenic event having the Dy10 promoter in experiment 1, 2 and 3 but not in experiment 4. This could be indicative of an interaction between Dy10 promoter and seed setting capability, or simply the product of insertion site of the gene or the effect of somaclonal variation, which might have been fixed with advancing the generation. There is no evidence in the literature supporting the idea that Dy10 promoter can compromise seed setting capability of a plant.

We did note a slight increase in time to physiological maturity for transgenic plants at the highest temperature tested. However, our data suggest that SSI activity was maintained under high temperature and likely allowed continued use of photo-assimilate. The increased grain fill duration we observed may be due to reduction of feedback inhibition of photosynthesis by reducing the accumulation of sugars.

The transgene with the Dy10 promoter produced the heaviest seeds and had longest grain filling duration (GFD). This result may support the feedback inhibition theory. Although we observed that some Dy10 plants also produced fewer seeds per spike and total grain yield was reduced, this is likely as an artifact based on the gene insertion site as this was not observed in all Dy10 plants. This somaclonal variation can be addressed with advancement of the wheat lines.

Our results suggest that incorporation of more heat stable forms of key enzymes may be a good strategy for improving heat tolerance in crop plants. This approach should be beneficial for all cool season species that are grown under conditions where heat stress may limit production. It may be useful to explore the relative heat stability of SS from other species typically grown under high temperature conditions to identify the most heat tolerant source of the enzyme.

There is genetic variability within wheat for the ability to maintain greenness under heat stress. The cultivar used in this study is not particularly tolerant to heat stress. Deployment of the rice construct in lines that demonstrate heat tolerance may be an avenue to even greater levels of production under heat stress.

Example 3

Prediction of Relative Thermostability

The relative thermostabililty of various soluble starch synthase proteins was predicted using an algorithm developed by Li et al. (*A novel scoring function for discriminating hyperthermophilic and mesophilic proteins with application to predicting relative thermostability of protein mutants*, BMC Bioinformatics 11:62, 2010, open access). The Wins score-value is the relative (weighted) value assigned to the sequences. Comparing several protein sequences of starch synthases in Genbank it is predicted that the protein for rice has greater thermostability than the starch soluble synthase from wheat (Table 1). Our data from the transgenic lines of wheat expressing the modified rice (*Oryza sativa*) SSS gene corroborates this prediction. The SSS protein sequences of *Triticum aestivum* (SEQ ID NO:36), *A. tausachii* (SEQ ID NO:37), and *Hordeum vulgare* (SEQ ID NO:38) are predicted to be the least thermostable of all genes analyzed.

Based upon this data, codon-optimize DNA sequences for *Vitis vinifera* (grape) (SEQ ID NO:39), *Poplar triocarpa* (Black Cottonwood) (SEQ ID NO:40), and *Sorghum bicolor* (*sorghum*) (SEQ ID NO:41) were synthesized by Genscript. The modification of the nucleic acid sequence did not alter the resulting amino acid sequence. The modification was due in part to codon optimizing the sequence and for cloning purposes. These genes have been subcloned into the two plasmids used for wheat transformation (the DY10 and the maize ubiquitin promoter, described above). Wheat genetically modified with these vectors is in the process of being engineered.

TABLE 10

Predicted thermostability relationship of selected starch synthase proteins from various species.

| Species | SEQ ID NO: | AA | Relative Thermostability ranking[A] | Wins score_value |
|---|---|---|---|---|
| Vitis vinifera** | 4 | 633 | 0 | 0.316 |
| Theobroma cacao | 16 | 645 | 1 | 0.289 |
| Poplar triocarpa** | 6 | 649 | 2 | 0.164 |
| Manihot esculenta | 17 | 633 | 3 | 0.141 |
| Amaranthus cruentus | 9 | 649 | 4 | 0.039 |
| Phaseolus vulgaris | 10 | 645 | 5 | 0.036 |
| Solanum lycopersicum | 20 | 641 | 6 | 0.025 |
| Prunus persica | 19 | 645 | 7 | 0.024 |
| Ostreococcus tauri | 11 | 525 | 8 | 0.015 |
| Glycine max | 12 | 651 | 9 | 0.001 |
| Cicer arietinum | 18 | 648 | 10 | −0.021 |
| medicago truncatula | 13 | 655 | 11 | −0.039 |
| Oryza sativa* | 2 | 641 | 12 | −0.050 |
| Zea mays | 14 | 640 | 13 | −0.131 |
| Arabidopsis thaliana | 15 | 575 | 14 | −0.142 |
| Sorghum bicolor** | 8 | 629 | 15 | −0.151 |
| Triticum aestivum | 36 | 647 | 16 | −0.160 |
| Ae. tauschii | 37 | 647 | 17 | −0.165 |
| Hordeum vulgare | 38 | 643 | 18 | −0.191 |

*amino acid sequenced expressed in transgenic wheat lines
**modified DNA sequences introduced into wheat
[A]Listed in order of more thermally stable to less thermally stable.
Based upon this data, species at the top of the table have a higher relative thermostability as compared to species further down in the table.

Example 4

Investigation of Heat Tolerance in Transgenic Wheat Expressing SSS Proteins Predicted to have Elevated Thermotolerance Genes derived from black cottonwood, *sorghum*, and grape were codon optimized (modified from their endogenous/native sequence) for wheat and synthesized, followed by transformation into wheat and testing of selected events for heat tolerance. The three codon-optimized soluble starch synthase genes (black cottonwood (PtriSSS) (SEQ ID NO:40), grape (VvitusSSS) (SEQ ID NO:39), and *sorghum* (SbicolorSSS)) (SEQ ID NO:41)) were subcloned into either pAHC17 (containing the maize ubiquitin promoter) or pJL10P5 (containing the HMW-Dy10 glutenin promoter of wheat and the nopaline synthase (NOS) terminator) (FIG. 1) and were transformed into wheat as described in Example 1. Several events were recovered and seeds harvested from these plants (Table 11).

TABLE 11

Transgenic events recovered from wheat transformations with codon-optimized SSS gene sequences derived from grape, black cottonwood and *sorghum*.

| Vector and GOI | # transgenic BW plant |
|---|---|
| pJL-Vvitus | 19 |
| p17-Vvitus | 14 |
| pJL-Ptri | 16 |
| p17-Ptri | 9 |
| pJL-Sbi | 9 |
| p17-Sbi | 4 |

*pJL: pJL10P5 vector (the glutenin promoter); p17: pAHC17 vector (maize ubiquitin promoter)

Figure 5A:
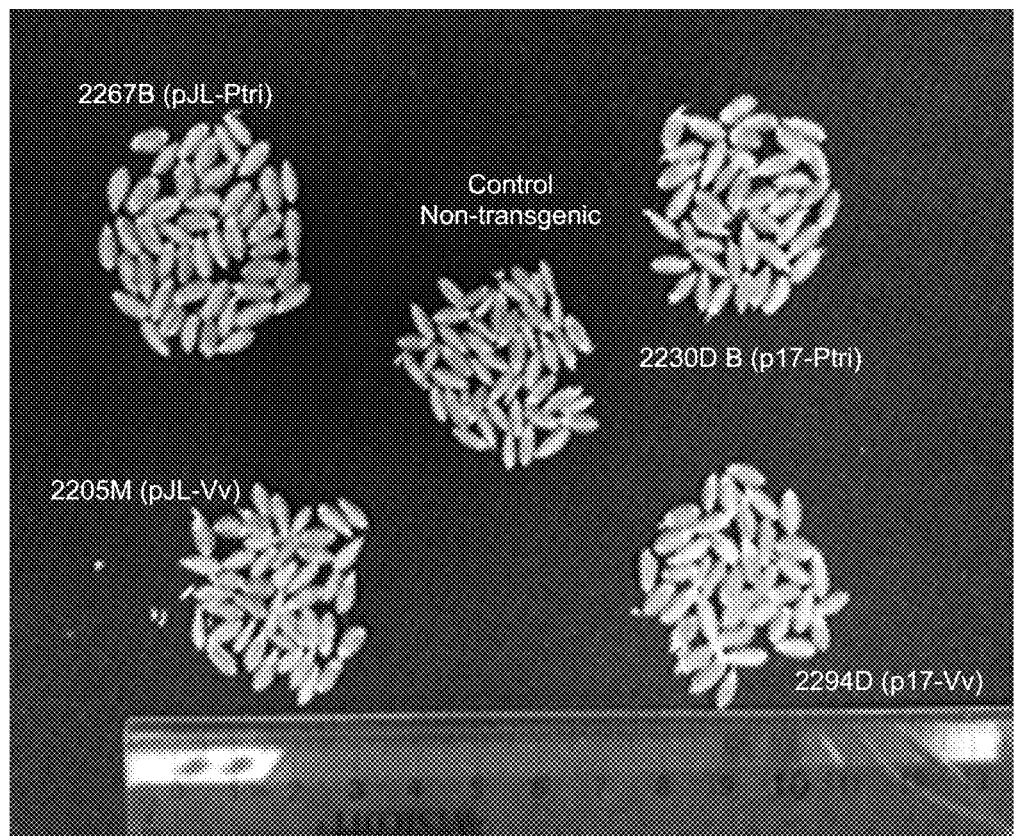
FIG. 5 is (a) a photograph of control and transgenic seed after heat treatment (32/28° C.); and (b) a graph showing the percent of thousand kernel weight (TKW) of transgenic lines over control bobwhite seeds, where * denotes P<0.05.
Figure 5B:
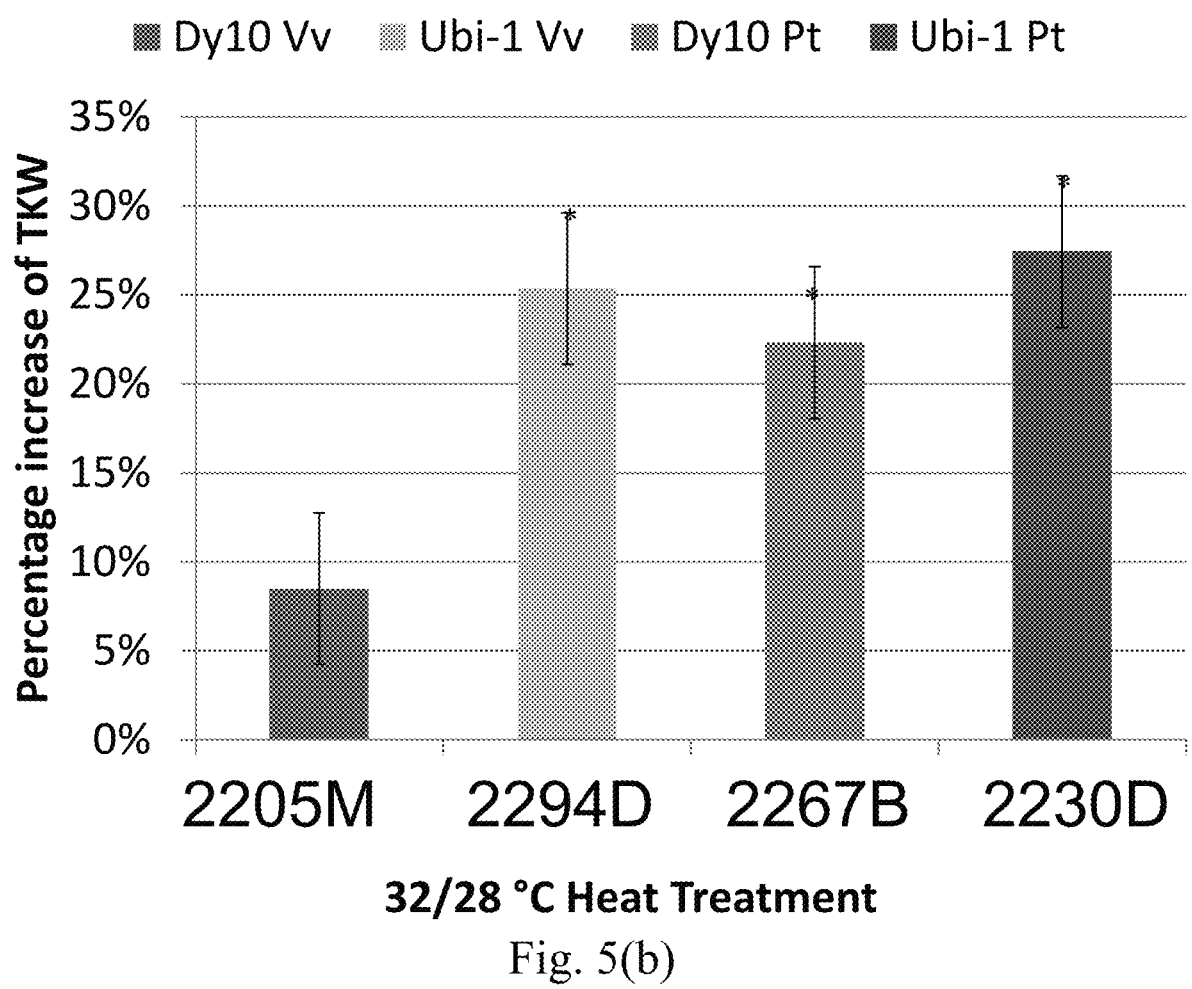

Heat treatment assays were performed on T1 generation black cottonwood and grape events. Ten seedlings each were planted from 2205M (pJL-Vvitus), 2294D (p17-Vvitus), 2267B (pJL-Ptri), and 2230D (p17-Ptri) events, as well as control (non-transformed) Bobwhite seeds. Under the optimum growth temperature, no physiological differences were observed between all transgenic plants and the non-transgenic bobwhite plants. Results from heat treatments indicated that all transgenic lines of SSS genes increased grain weight at heat stress during the grain filling stage compared to the bobwhite control plants (2205M TKW was higher than controls but not significantly) (FIG. 5). Specifically, data indicates that the seeds weight from the transgenic plants were 20-30% heavier (i.e., larger) than the control at elevated temperature.

Example 5

Figure 6A:
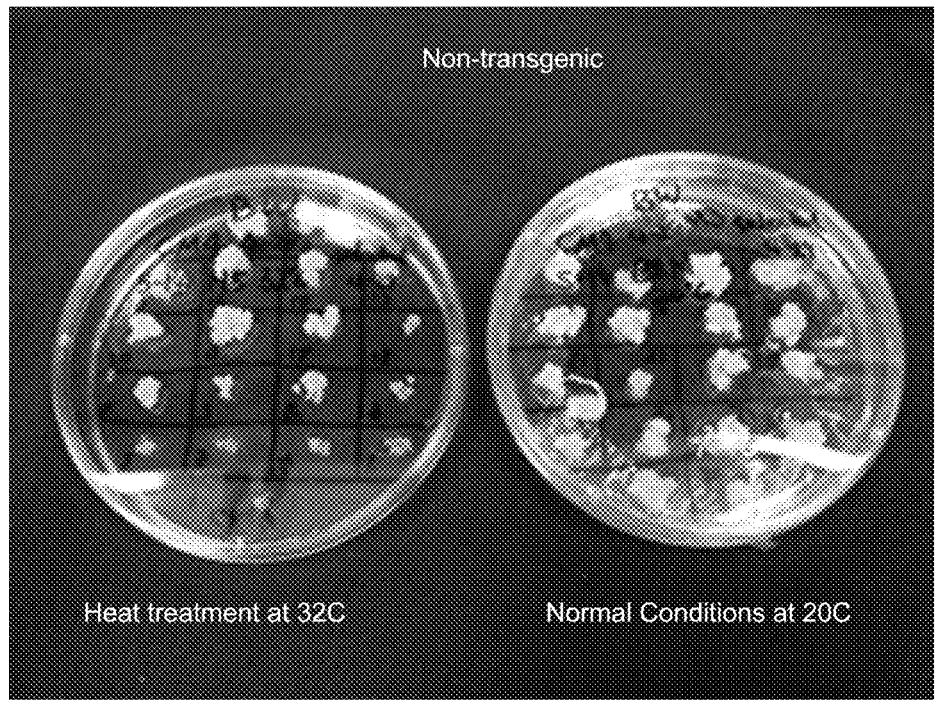
FIG. 6 shows photographs of growth comparison of (a) non-transgenic control Bobwhite calli to (b) transgenic calli of event 2205M-2 at elevated temperature (32° C.) and optimum growth conditions 20° C.
Figure 6:
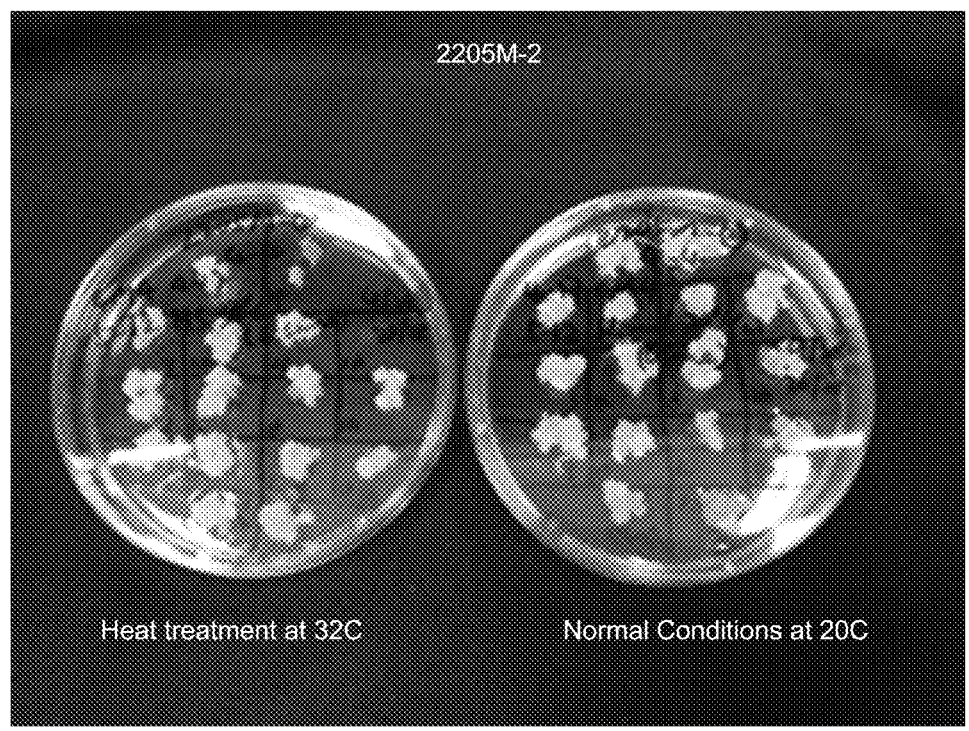

Investigation of Heat Tolerance in Wheat Embryogenic Calli Expressing SSS Proteins Predicted to have Elevated Thermotolerance In this example, the effects in vitro on tissue culture derived material (callus or calli) were tested. Heat treatment assays on transgenic calli were performed. Before heat treatment, the callus was cut into even two parts and put into the same number of grid on each petri dish. With a starch colorimetric/fluorometric assay kit, the concentrations of soluble starch in some calli under heat treatment were tested. At 32° C. some tolerance to heat stress was demonstrated, as shown in FIG. 6. Many non-transgenic calli were dead after 4 weeks of heat treatment (top left) compared to the control at 20° C. (top right). The transgenic calli growing under the same heat treatment (bottom left) continued to grow. Preliminary results indicated that the transgenic calli have increased thermotolerance contained significantly higher soluble starch than non-transgenic control after heat treatment. The data indicates that these SSS genes are effective in embryogenic tissue. Further these in vitro heat treatment assays can be used to screen the effectiveness of a target transgene.

Example 6

Investigation of Heat Tolerance in Maize Calli Expressing SSS Proteins Predicted to have Elevated Thermotolerance To validate the effects of thermotolerant SSS genes on other species beyond wheat, maize callus tissue (Hi IIA X HiIIB genotype) was co-transformed and regenerated as described by Songstadt et al. (1996) with either the black cottonwood (PtriSSS) (SEQ ID NO:40) or the grape (VvitusSSS) (SEQ ID NO:39) under control of the maize ubiquitin promoter and pACH20 containing the resistance gene for gluphosinate. Forty-eight events with the black cottonwood traits and thirteen events with the grape SSS gene have been identified and are under regeneration.

To test the effect of the thermotolerant SSS genes on growth during elevated temperatures, non-transgenic (control) and transgenic maize embryogenic calli were subjected to heat treatments (35° C.) and to normal growth temperature for maize calli (25° C.) for thirteen days. Approximately 250 mg calli were initially used in each sample and then weighed at the completion of the experiment. The growth of the control calli at 25° C. was an 8.56 fold increase in tissue compared to the initial weight. The control tissue grown at 35° C. only saw a 1.8 fold increase in growth. The growth observed from the transgenic line at 25° C. was a 7.56 fold increase over the initial weight, similar to the control. The transgenic line at 35° C. had a 9.28 fold increase compared to the initial weight. Data from this experiment suggest that the addition of the thermotolerant codon-optimized SSS gene from black cottonwood (SEQ ID NO:40) to maize significantly increases tissue growth at elevated temperatures, and indicates that expression of the Black cottonwood sequence can confer thermotolerance to corn.

What is claimed:

1. A genetically-modified plant having increased tolerance to heat stress as compared to a control plant, wherein said genetically-modified plant comprises a heterologous exogenous nucleic acid encoding soluble starch synthase from grape or cottonwood, wherein said soluble starch synthase from grape or cottonwood is expressed in said genetically-modified plant, said exogenous nucleic acid comprising a nucleotide sequence of SEQ ID NO:3 or 5, or a nucleotide sequence encoding the amino acid sequence of SEQ ID NO: 4 or 6.

2. The genetically-modified plant of claim 1, said plant being selected from the group consisting of wheat, oat, barley, rice, maize, millet, rye, *sorghum*, triticale, buckwheat, quinoa, soybeans, beans, peas, alfalfa, potatoes, sweet potatoes, cassava, and yam.

3. The genetically-modified plant of claim 1, said genetically-modified plant having increased yield as compared to said control plant, wherein said increased yield is selected from the group consisting of an increase in total seed weight, increased thousand kernel weight, increased biomass, and combinations thereof.

4. A method of increasing tolerance to heat stress in a plant, said method comprising:
   transforming said plant with a heterologous exogenous nucleic acid encoding soluble starch synthase from grape or cottonwood, wherein said soluble starch synthase is expressed in said genetically-modified plant to yield a transformed plant, thereby increasing the heat stress tolerance of said transformed plant, said exogenous nucleic acid comprising a nucleotide sequence of SEQ ID NO:3 or 5, or a nucleotide sequence encoding the amino acid sequence of SEQ ID NO: 4 or 6.

5. The method of claim 4, wherein said nucleic acid is operably linked to a promoter that drives expression of said soluble starch synthase in a plant cell.

6. The method of claim 4, wherein said plant comprises a plant tissue, and wherein said transforming comprises:
   culturing said tissue on media;
   introducing said exogenous nucleic acid into the cells of said tissue to yield transformed tissue;
   inducing callus formation from said transformed tissue;
   regenerating shoots; and
   rooting of said shoots in rooting media to regenerate said whole plant.

7. The method of claim 6, wherein said introducing is selected from the group consisting of: *Agrobacterium*-mediated transformation, PEG-mediated uptake, electroporation-mediated uptake, particle bombardment-mediated delivery, viral infection, and/or microinjection.

8. The method of claim 4, further comprising growing said transformed plant under an elevated growing temperature, wherein said transformed plant has increased yield as compared to a control plant grown under said elevated growing temperature.

9. A genetically-modified seed produced from a transformed plant according to the method of claim 4.

10. A method of producing genetically-modified plants having increased tolerance to heat stress as compared to a control plant, said method comprising: crossing a first parent plant with a second parent plant to thereby produce progeny, wherein at least one of said first or second parent plants is the genetically-modified plant according to claim 1, said progeny having increased tolerance to heat stress as compared to a control plant.

11. The method of claim 10, wherein each of said first and second parent plants is the genetically-modified plant according to claim 1.

12. The method of claim 10, wherein said first parent plant is the genetically-modified plant according to claim 1, and said second parent plant has the characteristic of pest resistance.

13. The method of claim 10, further comprising selecting for progeny plants having increased tolerance to heat stress.

14. The method of claim 10, wherein said crossing comprises:
   producing progeny seed from said first parent plant and said second parent plant;
   harvesting and planting said progeny seed to produce said progeny plant.

15. A recombinant plant cell having ectopic expression of a heterologous exogenous soluble starch synthase from grape or cottonwood by stable transformation with a nucleic acid construct encoding said soluble starch synthase, wherein said nucleic acid is synthesized from a native soluble starch synthase gene isolated from grape or cottonwood and cloned into said construct, said exogenous nucleic acid comprising a nucleotide sequence of SEQ ID NO:3 or 5, or a nucleotide sequence encoding the amino acid sequence of SEQ ID NO: 4 or 6.

16. A codon optimized cDNA sequence for transforming plants for increased heat tolerance selected from the group consisting of SEQ ID NO:3 and 5.

* * * * *